(12) United States Patent
Blauwkamp et al.

(10) Patent No.: US 10,697,008 B2
(45) Date of Patent: Jun. 30, 2020

(54) SAMPLE PREPARATION METHODS, SYSTEMS AND COMPOSITIONS

(71) Applicant: Karius, Inc., Redwood City, CA (US)

(72) Inventors: Timothy A. Blauwkamp, Palo Alto, CA (US); Rene Sit, Sunnyvale, CA (US); Igor D. Vilfan, East Palo Alto, CA (US)

(73) Assignee: KARIUS, INC., Redwood City, CA (US)

( * ) Notice: Subject to any disclaimer, the term of this patent is extended or adjusted under 35 U.S.C. 154(b) by 61 days.

(21) Appl. No.: 15/952,203

(22) Filed: Apr. 12, 2018

(65) Prior Publication Data

US 2018/0371538 A1 Dec. 27, 2018

Related U.S. Application Data

(60) Provisional application No. 62/484,856, filed on Apr. 12, 2017.

(51) Int. Cl.

| | |
|---|---|
| *C12Q 1/6869* | (2018.01) |
| *C12Q 1/6806* | (2018.01) |
| *C12N 9/12* | (2006.01) |
| *C12N 9/00* | (2006.01) |
| *C12Q 1/6855* | (2018.01) |
| *C12Q 1/686* | (2018.01) |
| *C12Q 1/6876* | (2018.01) |
| *C12N 1/00* | (2006.01) |

(52) U.S. Cl.
CPC ......... *C12Q 1/6869* (2013.01); *C12N 9/1247* (2013.01); *C12N 9/93* (2013.01); *C12Q 1/6806* (2013.01); *C12Q 1/686* (2013.01); *C12Q 1/6855* (2013.01); *C12Q 1/6876* (2013.01); *C12Q 2521/107* (2013.01); *C12Q 2533/101* (2013.01); *C12Y 207/07006* (2013.01); *C12Y 207/07049* (2013.01); *C12Y 605/01001* (2013.01); *C12Y 605/01003* (2013.01)

(58) Field of Classification Search
CPC ............ C12Q 1/6806; C12Q 2525/191; C12Q 1/6855
See application file for complete search history.

(56) References Cited

U.S. PATENT DOCUMENTS

| | | | |
|---|---|---|---|
| 6,753,137 | B2 | 6/2004 | Lo et al. |
| 6,787,308 | B2 | 9/2004 | Balasubramanian et al. |
| 6,833,246 | B2 | 12/2004 | Balasubramanian |
| 6,897,023 | B2 | 5/2005 | Fu et al. |

(Continued)

FOREIGN PATENT DOCUMENTS

| | | |
|---|---|---|
| EP | 1856295 A2 | 11/2007 |
| EP | 1885877 A2 | 2/2008 |

(Continued)

OTHER PUBLICATIONS

Constans, A. Beyond Sanger: Toward the $1,000 Genome.The Scientist. Jun. 30, 2003; 17(13): 36.

(Continued)

*Primary Examiner* — Teresa E Strzelecka
(74) *Attorney, Agent, or Firm* — Wilson, Sonsini, Goodrich & Rosati, P.C.

(57) ABSTRACT

The disclosure provides methods, compositions, systems, and kits for the concurrent detection and analysis of different structural and chemical forms of nucleic acids in a sample.

22 Claims, 20 Drawing Sheets

Specification includes a Sequence Listing.

(56) References Cited

U.S. PATENT DOCUMENTS

| | | |
|---|---|---|
| 6,969,488 B2 | 11/2005 | Bridgham et al. |
| RE39,920 E | 11/2007 | Umansky et al. |
| 7,803,929 B2 | 9/2010 | Melkonyan et al. |
| 7,914,982 B2 | 3/2011 | Melkonyan et al. |
| 7,973,154 B2 | 7/2011 | Melkonyan et al. |
| 8,682,592 B2 | 3/2014 | Rabinowitz et al. |
| 8,703,652 B2 | 4/2014 | Quake et al. |
| 8,877,442 B2 | 11/2014 | Quake et al. |
| 9,353,414 B2 | 5/2016 | Fan et al. |
| 9,580,755 B2 | 2/2017 | Thierry et al. |
| 2002/0012930 A1 | 1/2002 | Rothberg et al. |
| 2003/0022207 A1 | 1/2003 | Balasubramanian et al. |
| 2003/0058629 A1 | 3/2003 | Hirai et al. |
| 2003/0064398 A1 | 4/2003 | Barnes |
| 2003/0100102 A1 | 5/2003 | Rothberg et al. |
| 2003/0148344 A1 | 8/2003 | Rothberg et al. |
| 2004/0106110 A1 | 6/2004 | Balasubramanian et al. |
| 2004/0209299 A1 | 10/2004 | Pinter et al. |
| 2004/0248161 A1 | 12/2004 | Rothberg et al. |
| 2005/0079510 A1 | 4/2005 | Berka et al. |
| 2005/0100932 A1 | 5/2005 | Lapidus et al. |
| 2005/0124022 A1 | 6/2005 | Srinivasan et al. |
| 2005/0202414 A1 | 9/2005 | Jia et al. |
| 2006/0012784 A1 | 1/2006 | Ulmer |
| 2006/0012793 A1 | 1/2006 | Harris |
| 2006/0024678 A1 | 2/2006 | Buzby |
| 2006/0024711 A1 | 2/2006 | Lapidus et al. |
| 2006/0078909 A1 | 4/2006 | Srinivasan et al. |
| 2010/0068711 A1 | 3/2010 | Umansky et al. |
| 2012/0021412 A1 | 1/2012 | Melkonyan et al. |
| 2012/0077185 A1 | 3/2012 | Oliphant et al. |
| 2012/0190663 A1 | 7/2012 | Gornik et al. |
| 2012/0295810 A1 | 11/2012 | Quake et al. |
| 2013/0024127 A1 | 1/2013 | Stuelpnagel et al. |
| 2013/0178544 A1 | 7/2013 | Melkonyan et al. |
| 2013/0237431 A1 | 9/2013 | Lo et al. |
| 2013/0245961 A1 | 9/2013 | Lo et al. |
| 2013/0252835 A1 | 9/2013 | Koh et al. |
| 2014/0066317 A1 | 3/2014 | Talasaz |
| 2014/0147851 A1 | 5/2014 | Qian |
| 2014/0242582 A1 | 8/2014 | Oliphant et al. |
| 2014/0274740 A1 | 9/2014 | Srinivasan et al. |
| 2015/0133391 A1 | 5/2015 | De et al. |
| 2016/0017420 A1 | 1/2016 | Koh et al. |
| 2016/0304953 A1 | 10/2016 | Chen et al. |
| 2017/0016048 A1 | 1/2017 | Blauwkamp et al. |
| 2017/0145507 A1 | 5/2017 | Koh et al. |
| 2017/0145508 A1 | 5/2017 | Koh et al. |
| 2017/0145509 A1 | 5/2017 | Koh et al. |
| 2017/0166982 A1 | 6/2017 | Thierry et al. |

FOREIGN PATENT DOCUMENTS

| | | |
|---|---|---|
| EP | 2351857 A1 | 8/2011 |
| WO | WO-2012159023 A2 | 11/2012 |
| WO | WO-2012168815 A2 | 12/2012 |
| WO | WO-2013052907 A2 | 4/2013 |
| WO | WO-2013132305 A1 | 9/2013 |
| WO | WO-2013138536 A1 | 9/2013 |
| WO | WO-2013156627 A1 | 10/2013 |
| WO | WO-2013159035 A2 | 10/2013 |
| WO | WO-2013188846 A1 | 12/2013 |
| WO | WO-2014039556 A1 | 3/2014 |
| WO | WO-2014068075 A1 | 5/2014 |
| WO | WO-2014149134 A2 | 9/2014 |
| WO | WO-2015173402 A1 | 11/2015 |
| WO | WO-2018057820 A1 | 3/2018 |
| WO | WO-2018119452 A2 | 6/2018 |

OTHER PUBLICATIONS

Drmanac, R. et al. Human genome sequencing using unchained base reads on self-assembling DNA nanoarrays. Science 327, 78-81 (2010).

Gansauge, et al. Single-stranded DNA library preparation for the sequencing of ancient or damaged DNA. Nat Protoc. Apr. 2013;8(4):737-48. doi: 10.1038/nprot.2013.038. Epub Mar. 14, 2013.

Garaj, et al. Graphene as a sub-nanometer trans-electrode membrane. Nature. Sep. 9, 2010, 467.7312: 190-193. doi: 10.1038/nature09379.

Highlander, Sarah K., High throughput sequencing methods for microbiome profiling: application to food animal systems, Animal Health Research Reviews, Jun. 2012, vol. 13(1); pp. 40-53.

Huber et al. High-resolution liquid chromatography of DNA fragments on non-porous poly(styrene-divinylbenzene) particles. Nucleic Acids Res. Mar. 11, 1993;21(5):1061-6.

Karlsson et al. Amplification-free sequencing of cell-free DNA for prenatal non-invasive diagnosis of chromosomal aberrations. Genomics. Mar. 2015;105(3):150-8.

Kato et al. A new packing for separation of DNA restriction fragments by high performance liquid chromatography. J Biochem. Jan. 1984;95(1):83-6.

Reuter et al. Simul-seq: combined DNA and RNA sequencing for whole-genome and transcriptome profiling. Nat Methods. Nov. 2016; 13(11): 953-958. Manuscript; available Dec. 18, 2017.

Saukkonen, et al. Cell-free plasma DNA as a predictor of outcome in severe sepsis and septic shock. Clin Chem. Jun. 2008;54(6):1000-7. doi: 10.1373/clinchem.2007.101030. Epub Apr. 17, 2008.

Soni, et al. Progress toward ultrafast DNA sequencing using solid-state nanopores. Clin Chem. Nov. 2007;53(11):1996-2001. Epub Sep. 21, 2007.

Dey, S. et al., Integrated genome and transcriptome sequencing from the same cell, Nat. Biotechnol. 2015, 33(3), p. 285-289.

PCT/US2018/027393 International Search Report and Written Opinion dated Jul. 16, 2018.

SAMPLE PREPARATION METHODS, SYSTEMS AND COMPOSITIONS

CROSS-REFERENCE

This application claims the benefit of U.S. Provisional Application No. 62/484,856, filed Apr. 12, 2017 which is incorporated herein by reference in its entirety.

SEQUENCE LISTING

The instant application contains a Sequence Listing which has been filed electronically in ASCII format and is hereby incorporated by reference in its entirety. Said ASCII copy, created on Jul. 10, 2018, is named 47697_709_201_SL.txt and is 2,751 bytes in size.

BACKGROUND

The analysis of genetic material in a sample has numerous potential uses and applications, including the identification of genetic indicators of disease (e.g., cancer), infection, disease progression, and fetal health. Advances in high-throughput sequencing technologies and PCR-based approaches have permitted more accurate identification of such genetic material. Before these approaches can be used, usually a starting sample is processed in some manner. For example, nucleic acids may be extracted or purified from the sample. The nucleic acids may then be tagged in some manner. Tagging may aid the detection of the sequence of the nucleic acids in a downstream application, such as by making the nucleic acid compatible for use in a particular type of sequencer.

SUMMARY

The application of current technologies for genetic analysis is often impeded by inefficient sample processing techniques. Also, most nucleic acid sample preparation methods have limited uses in that they only can detect one nucleic acid form at a time. For example, most sample preparation methods require that a sample be divided so that RNA and DNA can be processed in parallel. Samples containing low quantities of nucleic acids, or low quality nucleic acids, may thus not have sufficient material to permit detection of both RNA and DNA, resulting in the possible loss of valuable information about the sample.

The present disclosure overcomes these challenges and others. Many of the methods, compositions, systems, and kits provided herein enables the concurrent processing and detection of multiple different types of nucleic acids, generally without the need of physically separating or dividing a sample. Such concurrent analysis of different nucleic acid forms in a sample permits more efficient detection of genetic material, and for more accurate and useful genetic analyses.

Provided herein are methods, systems, processes, kits, and reagent compositions useful for carrying out sample preparation processes for the analysis of different forms of nucleic acids in a sample. The methods include methods of processing nucleic acids of multiple forms (e.g., single-stranded DNA, double-stranded DNA, single-stranded RNA, and/or double-stranded RNA) within samples to identify the nucleic acids present within the sample. The methods, systems, processes, kits, and reagent compositions provided herein can often be practiced or used in a single reaction mixture, without the need to separate or divide a sample into different portions.

In some embodiments, the methods can be applied to samples that comprise both DNA and RNA fragments of interest, and result in the analysis of both of those nucleic acid forms from a single reaction mixture. Further, these methods may identify fragments in accordance with their originating form in the sample, e.g., as DNA or RNA and/or as single-stranded or double-stranded, such that downstream analysis may yield both sequence identification and identification of the chemical and/or structural form of the original nucleic acid in the sample.

In one aspect, provided herein is a method of performing a primer extension reaction on RNA and DNA, comprising: (a) providing a sample comprising a mixture of single-stranded DNA and single-stranded RNA, (b) attaching a first adapter to the single-stranded DNA, (c) attaching a second adapter to the single-stranded RNA, (d) annealing a first primer to the first adapter and annealing a second primer to the second adapter, (e) extending the annealed first primer on the single-stranded DNA to form double-stranded DNA, and/or (f) extending the annealed second primer on the single-stranded RNA to form a double-stranded DNA-RNA hybrid. In some cases, the attaching the first adapter to the single-stranded DNA comprises ligating the first adapter to the single-stranded DNA. In some cases, the attaching of the first adapter to the single-stranded DNA comprises performing a primer extension reaction. In some cases, the attaching the first adapter to the single-stranded rNA comprises ligating the first adapter to the single-stranded rNA. In some cases, the attaching of the first adapter to the single-stranded RNA comprises performing a primer extension reaction.

In some cases, the first adapter is ligated or attached to the 3' end of the single-stranded DNA. In some cases, the second adapter is ligated or attached to the 3' end of the single-stranded RNA. In some cases, the ligating or attaching of said first adapter and said second adapter occurs concurrently or within a single reaction mixture. In some cases, extending the first primer on the single-stranded DNA to form double-stranded DNA occurs prior to the annealing of the second primer to the second adapter ligated to the end (e.g., 3' end) of the single-stranded RNA. In some cases, the extending the first primer on the single-stranded DNA to form double-stranded DNA occurs at the same time as the extending the second primer on the single-stranded RNA to form a double-stranded DNA-RNA hybrid. In some cases, the first adapter and the second adapter have different sequences. In some cases, the first adapter and the second adapter have the same sequence. In some cases, the first primer and the second primer have different sequences. In some cases, the first primer and the second primer have the same sequence. In some cases, the extending of the first primer can be performed using a first polymerase that adds at least one first non-templated nucleotide to an end (e.g., 3' end) of a first primer extension strand, thereby generating a first overhang. In some cases, the extending of the second primer is performed using a second polymerase that adds at least one second non-templated nucleotide to an end (e.g, 3' end) of a second primer extension strand, wherein the at least one second non-templated nucleotide is different from the at least one first non-templated nucleotide, thereby generating a second overhang.

In some cases, the methods further comprise hybridizing a third adapter to the first overhang and a fourth adapter to the second overhang. In some cases, the method further comprises sequencing the third and fourth adapters and sequences attached to the third and fourth adapters. In some cases, the method further comprises (i) identifying sequences associated with the third adapter as originating from the DNA in the initial mixture of single-stranded DNA and single-stranded RNA and (ii) identifying sequences associated with the fourth adapter as originating from the RNA in the initial mixture of single-stranded DNA and single-stranded RNA.

In one aspect, provide herein is a method of performing an amplification reaction on a first RNA and a first DNA, comprising: (a) providing a sample comprising a mixture of a first DNA and a first RNA, wherein the first DNA does not comprise a sequence complementary to the first RNA, (b) tagging an end (e.g, 3' end) of the first DNA with a first tag without using a transposase, (c) tagging a an end (e.g., a 3' end) of the first RNA such that the first RNA comprises a tag that is identical to the first tag or is not identical to the first tag, (d) performing an amplification or primer extension reaction on the first DNA with a polymerase that is selective for DNA templates, and (e) synthesizing a complementary cDNA strand from the first RNA with a reverse transcriptase. In some cases, the first DNA is derived from a bacterium and the first RNA is derived from a virus. In some cases, the method further comprises sequencing the first DNA and the first RNA.

In one aspect, provide herein is a method of sequencing nucleic acids, comprising: (a) providing a sample comprising a mixture of double-stranded nucleic acids and single-stranded nucleic acids, (b) attaching (e.g., by ligation or primer extension reaction) the first adapter to the double-stranded nucleic acids (e.g, at the 3' end of the double-stranded nucleic acids), (c) denaturing the double-stranded nucleic acids into single-stranded nucleic acids, (d) ligating a second adapter to the denatured nucleic acids of step c, wherein the second adapter has a different sequence than the first adapter or has a sequence that is identical to that of the first adapter, and/or (e) sequencing the nucleic acids ligated to the first and second adapters and/or identifying sequences associated with the first adapter as being double-stranded and/or sequences associated with the second adapter as being single-stranded.

In some cases, the double-stranded nucleic acids are DNA. In some cases, the double-stranded nucleic acids are RNA. In some cases, the single-stranded nucleic acids are RNA. In some cases, the single-stranded nucleic acids are DNA. In some cases, the method further comprises reducing concatemerization of short sequences. In some cases, the DNA is single-stranded DNA, double-stranded DNA, triple-stranded DNA, or a Holliday junction. In some cases, the RNA is single-stranded RNA, double-stranded RNA, or a ribozyme. In some cases, the DNA is cell-free DNA. In some cases, the RNA is cell-free RNA. In some cases, the sample is selected from the group consisting of blood, plasma, serum, cerebrospinal fluid, synovial fluid, bronchio-alveolar lavage, urine, stool, saliva, nasal swab, and any combination thereof.

In some cases, extending the primer on the single-stranded DNA can be performed by a DNA polymerase. In some cases, the extending the primer on the single-stranded DNA is performed by Bst 2.0 DNA polymerase. In some cases, the extending the primer on the single-stranded RNA can be performed by a polymerase selected from Moloney Murine Leukemia Virus (M-MLV) reverse transcriptase, and a SMARTer reverse transcriptase.

In some cases, a method described herein further comprises sequencing the amplified products.

In some cases, the ligating the first adapter is performed by a ligase selected from CircLigase II, Thermostable App-DNA/RNA ligase, T4 RNA ligase 1, T4 RNA Ligase 2 truncated, and any combination thereof. In some cases, the ligating the second adapter is performed using a double-stranded RNA ligase. In some cases, the ligating the second adapter is performed using T4 RNA ligase 2 or T4 DNA ligase.

In some cases, a method described herein further comprises adding at least one non-templated nucleotide to a primer extension strand. In some cases, the at least one non-templated nucleotide is a deoxyadenosine. In some cases, the at least one non-templated nucleotide is one non-templated nucleotide. In some cases, the third adapter ligated comprises an overhang containing at least one deoxythymidine. In some cases, the method further comprises adding at least one non-templated nucleotide to a primer extension strand of the double-stranded DNA-RNA hybrid. In some cases, the at least one non-templated nucleotide is a deoxycytidine. In some cases, the at least one non-templated nucleotide is added to a 3' end. In some cases, the at least one non-templated nucleotide is up to eight nucleotides. In some cases, the at least one non-templated nucleotide is three, four, or five non-templated nucleotides. In some cases, the fourth adapter contains an overhang comprising at least one deoxyguanosine residue. In some cases, the overhang comprises at least three deoxyguanosine residues.

In one aspect, provide herein is a method of performing an amplification reaction on a first RNA and a first DNA, comprising: (a) providing a sample comprising a mixture of a first DNA and a first RNA, wherein the first DNA is derived from a bacterium and the first RNA is derived from a virus, (b) amplifying the first RNA with a reverse transcriptase that selectively amplifies RNA, and (c) amplifying the first DNA with a polymerase that selectively amplifies DNA.

In one aspect, provided herein is a method of performing an amplification reaction on a first RNA and a first DNA, comprising: (a) providing a sample comprising a mixture of a first DNA and a first RNA, wherein the first DNA is genomic DNA derived from a first organism and the first RNA is genomic RNA derived from a second organism, (b) amplifying the first RNA with a reverse transcriptase that selectively amplifies RNA, and (c) amplifying the first DNA with a polymerase that selectively amplifies DNA. In some cases, the first organism can be a bacterium and the second organism can be a virus.

Provided herein are methods for concurrent processing of different nucleic acid forms in a sample. The method can comprise (a) denaturing the nucleic acid forms in a sample; (b) ligating a first adapter to one end a first nucleic acid form using a ligase that has a preference for a first nucleic acid form and ligating a second adapter to one end of a second nucleic acid form using a ligase that has preference for a second nucleic acid form; (c) primer extending a first and second ligated nucleic acid forms; (d) ligating a third adapter comprising a priming element; and (e) amplifying. In some cases, the ligating of the first adapter to the first nucleic acidf form occurs concurrently with the ligating of the second adapter to the second nucleic acid form, or in the same reaction mixture. In a method disclosed herein, a first nucleic acid form can be a DNA molecule and a second nucleic acid form can be RNA a molecule. In other cases, a first nucleic acid form can be ssDNA and a second nucleic acid form can be ssRNA. A polymerase can comprise a DNA-dependent polymerase and a RT polymerase. The polymerase can be selected from a Bst DNA Polymerase, a Full Length, a Bst DNA Polymerase, a Large Fragment, a Bsu DNA Polymerase, a Crimson Taq DNA Polymerase, a Large Fragment, Deep VentR™, a DNA Polymerase, a Deep VentR™ (exo-), a DNA Polymerase, a *E. coli* DNA Polymerase I, a Klenow Fragment (3'→5' exo-), a DNA Polymerase I, a Large (Klenow) Fragment, a LongAmp® Taq DNA Polymerase or Hot Start, a M-MuLV Reverse Transcriptase, a OneTaq® DNA Polymerase or Hot Start, a phi29 DNA Polymerase, a Phusion® Hot Start Flex DNA Polymerase, a Phusion® High-Fidelity DNA Polymerase, a Q5®+Q5® Hot Start DNA Polymerase, a Sulfolobus DNA Polymerase IV, a T4 DNA Polymerase, a T7 DNA Polymerase, a Taq DNA Polymerase, a Therminator™ DNA Polymerase, a VentR® DNA Polymerase, a VentR® (exo-) DNA Polymerase, and any combination thereof. In some cases, a RT polymerase can be selected from a WarmStart RTx Reverse Transcriptase, a AMV Reverse Transcriptase, a Superscript IV RT, a M-MLV Rnase H(−), a SMARTer reverse transcriptase, a RevertAid RnaseH(−) RT, a ProtoScript® II Reverse Transcriptase, and any combination thereof. Whereas a ligase can be selected from a T4 DNA Ligase, a T3 DNA Ligase, a T7 DNA Ligase, a *E. coli* DNA Ligase, a HiFi Taq DNA Ligase, a 9° N™ DNA Ligase, a Taq DNA Ligase, a SplintR® Ligase, a Thermostable 5' AppDNA/RNA Ligase, a T4 RNA Ligase, a T4 RNA Ligase 2, a T4 RNA Ligase 2 Truncated, a T4 RNA Ligase 2 Truncated K227Q, a T4 RNA Ligase 2, a Truncated KQ, a RtcB Ligase, a CircLigase II, a CircLigase ssDNA Ligase, a CircLigase RNA Ligase, a Ampligase® Thermostable DNA Ligase, and any combination thereof. The method described herein can further comprise a detecting step, wherein the detecting can be performed by a real-time PCR, sequencing, a digital droplet PCR, or a microarray detection assay. Sequencing can comprise a next generation sequencing, a massively-parallel sequencing, a pyrosequencing, a sequencing-by-synthesis, a single molecule real-time sequencing, a polony sequencing, a DNA nanoball sequencing, a heliscope single molecule sequencing, a nanopore sequencing, a Sanger sequencing, a shotgun sequencing, or a Gilbert's sequencing assay.

Provided herein are methods for concurrent processing of different nucleic acid forms in a sample. In some cases, the method can comprise: (a) denaturing a nucleic acid forms in a sample; (b) ligating a first adaptor to one end of a first nucleic acid form using a first ligase that has a preference for the first nucleic acid form and ligating a second adapter to one end of a second nucleic acid form using a second ligase that has a preference for the second nucleic acid form, wherein the first adapter and the second adapter comprise an identifying sequence that is different from each other; and (c) detecting the ligated nucleic acid forms.

Further provided are reaction mixtures comprising: an adapter; a first ligase that has a preference for a first nucleic acid form; a second ligase that has a preference for a second nucleic acid form; and a buffer. The reaction mixture can further comprise a polymerase and/or a RT polymerase described herein. In some cases, components of the reaction mixtures can be liquid, dry, or a combination thereof.

In other reaction mixtures provided herein, the reaction mixture can comprise: a ligase; a DNA-dependent polymerase that has non-templated activity, wherein the non-templated base can be N1; and a RT polymerase that has non-templated activity, wherein the non-templated base can be N2, wherein N1 and N2 can be different nucleic acid bases. In one instance, the DNA-dependent polymerase can be selected from an A- and B-family DNA polymerases, a KOD XL, KOD (exo-), a Bst 2.0, a Therminator, a Deep Vent (exo-), a Pfu DNA polymerase, and aTaq. In some cases, a reverse transcriptase used in the mixture can be selected from HIV reverse transcriptase, Moloney murine leukemia virus, SuperScript II™ (ThermoFisher), and SuperScript III™.

Provided herein are kits comprising: an adapter; a first ligase that has a preference for a first nucleic acid form; a second ligase that has a preference for a second nucleic acid form; and a buffer. In some cases, a kit can further comprise instructions for use. A kit provided herein can comprise: a ligase; a DNA-dependent polymerase that has non-templated activity, wherein the non-templated base is N1; and a RT polymerase that has non-templated activity, wherein the non-templated base can be N2, wherein N1 and N2 can be different nucleic acid bases. Kits provided herein can further comprise instructions for use. The DNA-dependent polymerase of a kit described herein can be selected from a A- and B-family DNA polymerases, a KOD XL, KOD (exo-), a Bst 2.0, a Therminator, a Deep Vent (exo-), a Pfu DNA polymerase, and aTaq. Whereas a reverse transcriptase can be selected from HIV reverse transcriptase, Moloney murine leukemia virus, SuperScript II™, and SuperScript III™. A kit provided herein may further comprise a control.

Provide herein are methods of sequencing for different nucleic acids forms. A method of sequencing can comprise: providing a sample comprising different nucleic acid forms; denaturing the nucleic acid forms in a sample; ligating a first adapter to one end of a first nucleic acid form using a ligase that has a preference of the first nucleic acid form; and ligating a second adapter to one end of a second nucleic acid form using a ligase that has preference of the second nucleic acid form, wherein the first and the second adapter comprise different identifying sequences; and sequencing the ligated nucleic acids, thereby identifying the different nucleic acid forms in the sample. The method can further comprise amplification by a polymerase, wherein the polymerase can be a DNA-dependent polymerase and/or an RT polymerase. In some cases, the sequencing described herein can be by a next generation sequencing, a massively-parallel sequencing, a pyrosequencing, a sequencing-by-synthesis, a single molecule real-time sequencing, a polony sequencing, a DNA nanoball sequencing, a heliscope single molecule sequencing, an nanopore sequencing, a Sanger sequencing, a shotgun sequencing, or a Gilbert's sequencing assay.

Also provided herein are methods for concurrent processing different nucleic acid forms in a sample. These methods can comprise: denaturing the nucleic acid forms in a sample; ligating a first adapter to one end a first nucleic acid form and a second nucleic acid form using a ligase; amplifying using a DNA-dependent polymerase that has non-templated activity, wherein the non-templated base can be N1; and amplifying using a RT polymerase that has non-templated activity, wherein the non-templated base can be N2, wherein N1 and N2 can be different nucleic acid bases. In some cases, a first nucleic acid form or a second nucleic acid form can be DNA, ssDNA, RNA or ssRNA. In some cases the DNA-dependent polymerase can be selected from A- and B-family DNA polymerases, KOD XL, KOD (exo-), Bst 2.0, Therminator, Deep Vent (exo-), Pfu DNA polymerase, and Taq. Whereas, a reverse transcriptase can be selected from HIV reverse transcriptase, Moloney murine leukemia virus, SuperScript II™, and SuperScript III™.

Also provided herein are a method for processing different nucleic acid forms in a sample comprising: (a) denaturing said different nucleic acid forms in a sample, wherein said different nucleic acid forms comprise a first nucleic acid form and a second nucleic acid form; (b) attaching a first adapter to said first nucleic acid form and a second adapter to said second nucleic acid form; (c) amplifying said first nucleic acid form using a DNA-dependent polymerase that has non-templated activity, wherein said non-templated activity comprises adding at least one N1 nucleotide or a first sequence to amplified products of said amplification of said first nucleic acid form; and (d) amplifying said second nucleic acid form using a reverse transcriptase polymerase that has non-templated activity, wherein said non-templated activity comprises adding at least one N2 nucloetide or a second sequence to amplified products of said amplification of said second nucleic acid form, wherein said N1 nucleotide and said N2 nucleotide are different nucleotides or said first sequence is different from said second sequence.

In some cases, said first nucleic acid form is a DNA molecule or said second nucleic acid form is RNA a molecule. In some cases, said first nucleic acid form is ssDNA and said second nucleic acid form is ssRNA. In some cases, said DNA-dependent polymerase is selected from A- and B-family DNA polymerases, KOD XL, KOD (exo-), Bst 2.0, Therminator, Deep Vent (exo-), Pfu DNA polymerase, and Taq. In some cases, said reverse transcriptase, is selected from HIV reverse transcriptase, Moloney murine leukemia virus, SuperScript II, and SuperScript III. In some cases, the method further comprises distinguishing said first nucleic acid form from said second nucleic acid form based on said non-templated activity of said reverse transcriptase or based on said non-templated activity of said DNA-dependent polymerase. In some cases, the method further comprises distinguishing said first nucleic acid form from said second nucleic acid form based on said N1 or N2 nucleotides or said first or second sequences. In some cases, said attaching of said first adapter or of said second adapter comprises performing a ligation reaction or primer extenstion reaction. In some cases, the attaching occurs at the 3' end of the first nucleic acid form or of the 3' end of the second nucleic acid form.

INCORPORATION BY REFERENCE

All publications, patents, and patent applications mentioned in this specification are herein incorporated by reference in their entireties to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
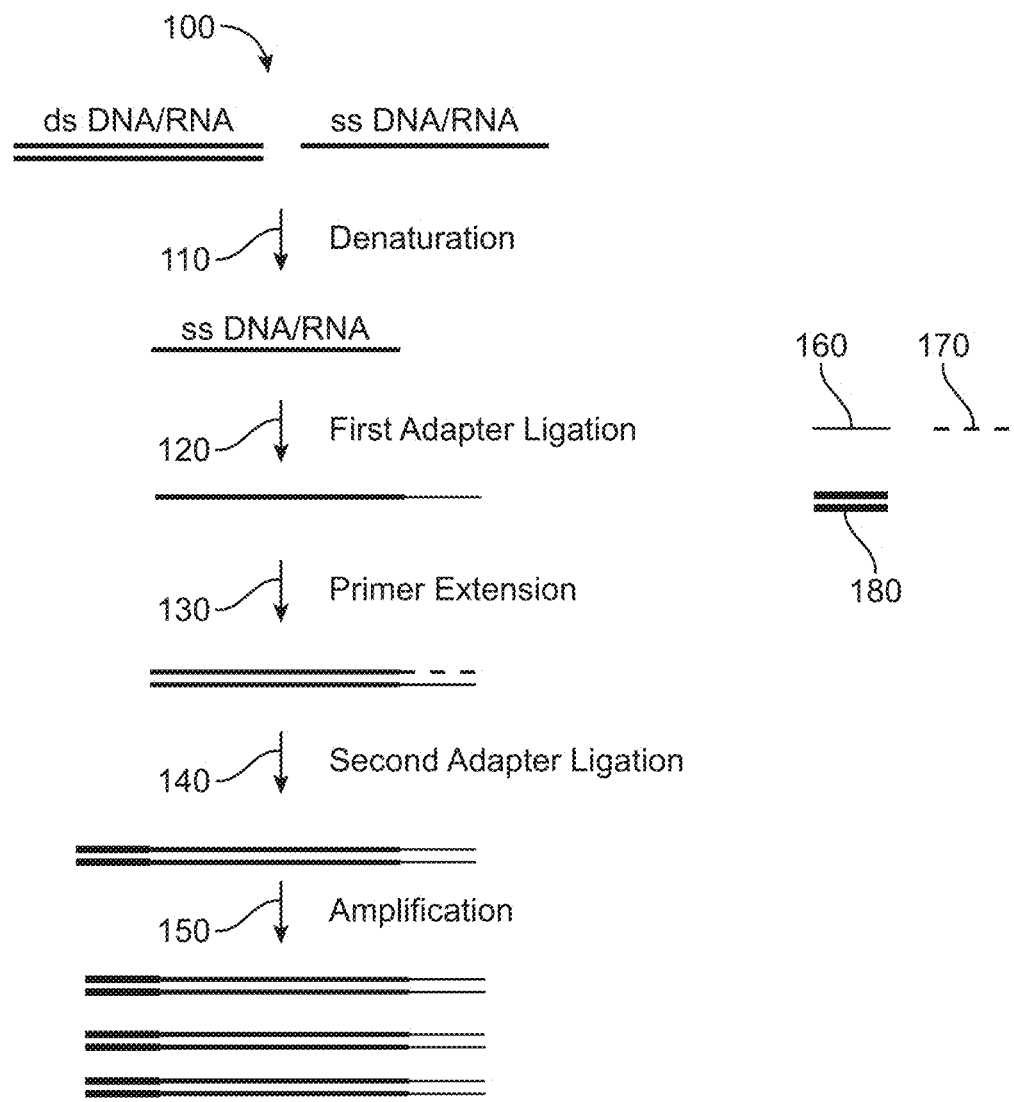
FIG. 1 shows exemplary approaches for processing DNA and RNA in a sample by adding adapters to single-stranded nucleic acids.

The following passages describe different aspects of the invention in greater detail. Each aspect, embodiment, or feature of the invention may be combined with any other aspect, embodiment, or feature the invention unless clearly indicated to the contrary.

I. Definitions

Unless defined otherwise, all technical and scientific terms used herein have the meaning commonly understood by a person skilled in the art to which this invention belongs.

"Detect," as used herein can refer to quantitative or qualitative detection, including, without limitation, detection by identifying the presence, absence, quantity, frequency, concentration, sequence, form, structure, origin, or amount of an analyte.

"Nucleic acid" as used herein, can refer to a polymer of nucleotides and is generally synonymous with the term "polynucleotide." The nucleotides may comprise a deoxyribonucleotide, a ribonucleotide, a deoxyribonucleotide analog, ribonucleotide analog, or any combination thereof. The term "nucleic acid" may also include nucleic acids with modified backbones. Nucleic acid can be of any length. Nucleic acid may perform any function, known or unknown. The following are non-limiting examples of nucleic acids: coding or non-coding regions of a gene or gene fragment, loci (locus) defined from linkage analysis, exons, introns, messenger RNA (mRNA), transfer RNA (tRNA), ribosomal RNA (rRNA), short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, primers, mitochondrial DNA, cell-free nucleic acids, viral nucleic acid, bacterial nucleic acid, and genomic DNA. A nucleic acid may comprise one or more modified nucleotides, such as methylated nucleotides or methylated nucleotide analogs. If present, modifications to the nucleotide structure may be imparted before or after assembly of the polymer. The sequence of nucleotides may be interrupted by non-nucleotide components. A nucleic acid may be further modified after polymerization, such as by conjugation with a labeling component. A nucleic acid may be single-stranded, double-stranded or have higher numbers strands (e.g., triple-stranded).

"A", "an", and "the", as used herein, can include plural referents unless expressly and unequivocally limited to one referent.

As used herein, the term "or" is used to refer to a nonexclusive "or"; as such, "A or B" includes "A but not B," "B but not A," and "A and B," unless otherwise indicated.

"Identifying sequence element" can refer to an index, a code, a barcode, a random sequence, an adaptor, an overhang of non-templated nucleic acids, a tag comprising one or more non-templated nucleotides, a priming sequence, or any combination thereof.

As used throughout the specification herein, the term "about" when referring to a number or a numerical range means that the number or numerical range referred to is an approximation within experimental variability (or within statistical experimental error), and the number or numerical range may vary from, for example, from 1% to 15% of the stated number or numerical range. In examples, the term "about" refers to ±10% of a stated number or value.

The term "denaturing", as used herein, can refer to a process in which biomolecules, such as proteins or nucleic acids, lose their structure relative to their native state. For example, a double-stranded nucleic acid molecule can be denatured into two single-stranded molecules. Denaturing of a protein molecule can lead to loss of its native 3D structure to a different structure.

II. General Overview

The present disclosure is directed to methods, compositions, systems, and kits for use in processing biological samples comprising nucleic acids for analysis. The present disclosure provides advantages for nucleic acid analysis of a sample by providing efficient detection, amplification, or quantification of different chemical or structural forms within a single reaction mixture. For example, the methods can be used for discriminating between RNA and DNA within a sample or discriminating between single-stranded and double stranded DNA or RNA within a sample. The methods can also be used for quantification of RNA or DNA. In some cases, the products generated by the methods provided herein are analyzed in a downstream assay such as qPCR, ddPCR, microarray, Sanger sequencing, or high-throughput sequencing.

A particular utility of the disclosed methods is that DNA pathogens (e.g., DNA viruses) can be analyzed at the same time as RNA pathogens (e.g., RNA pathogens) in a single reaction mixture, in addition, molecules with different structural forms (e.g., double-stranded, single-stranded) and folding properties (e.g., secondary structures) can be analyzed at the same time.

A general overview of some embodiments of the methods provided herein is schematically illustrated in FIG. 1. Generally, the method may begin with obtaining a sample from a subject, such as a human patient, who has or is suspected of having or is at risk of having a disease, pathogenic infection, cancer, fetal abnormality or other disorder. The sample may contain a mixture 100 of double-stranded (ds) DNA, single-stranded (ss) DNA, dsRNA, and ssRNA, or any combination thereof. As shown in FIG. 1, the nucleic acids in the sample may be subjected to denaturation 110, e.g., through application of heat (e.g., 95° C.), for a sufficient time period to ensure that all or most of the nucleic acids within a sample are present in single-stranded form. In some cases, the sample undergoes a denaturation process in order to remove secondary or tertiary structure from nucleic acids in the sample (e.g., ssDNA, ssRNA).

The single-stranded nucleic acids (DNA or RNA) may then be subjected to a first adapter ligation step 120 to append a first adapter 160 to the 3' end of the nucleic acid strand. The ligase may be a ligase capable of ligating to both ssRNA and ssDNA (e.g., CircLigase II) or may be a dual ligase system that includes a RNA-specific ligase and a DNA-specific ligase. In general, the adapters used in the methods provided herein are DNA molecules with a specific or random sequence. The first adapter may contain additional functional sequences (e.g., one or more of amplification and sequencing primers, as well as attachment sequences). The first adapter may be modified (e.g., biotinylated or modified with a different capture moiety). Streptavidin beads can be used to capture sample nucleic acids ligated to the first adapter as well as unligated first adapter. An excess amount of beads can be used to ensure the biotinylated first adapters and the ligated sample nucleic acids are captured to the beads. As depicted in FIG. 1, the first adapter may be single-stranded 160. In some cases, identical first adapters are added at this step, while in other cases, a mixture of first adapters with different sequences is added at this step. Generally, the adapter is appended by a ligation reaction using one or more ligase enzymes, as described further herein, however, other mechanisms may be used as well to append the first adapter (e.g., random priming), as described further herein.

The appended adapter may be used in a primer extension reaction in order to create a duplex nucleic acid. Generally, the primer 170 used in such primer extension reaction may be a DNA or RNA primer that is complementary to the sequence of the first adapter or complementary to one sequence of a mixture of first adapters. In some cases, identical primers can be added at this step, while in other cases, a mixture of primers with different sequences can be added at this step. The primer extension reaction may be performed by a polymerase 130. In some cases, the polymerase may be able to polymerize both DNA and RNA templates. Such polymerase may be used singly or in combination with a DNA-specific or DNA-selective polymerase and/or a RNA-specific or RNA-selective polymerase (e.g., reverse transcriptase or RNA-dependent RNA polymerase (e.g., Phi6 RNA polymerase)). In some cases, a polymerase specific for or selective for RNA can be used in combination with a DNA-specific or DNA-selective polymerase. Combinations of polymerases may be used sequentially or concurrently. In certain embodiments, polymerases capable of adding one or more non-templated nucleic acid residues to the end of a nascent strand of the duplex may be used, as described in more detail in FIG. 2 and FIG. 5. By appending such one or more non-templated nucleic acids residues, such polymerases may mark nucleic acids as originating from RNA or DNA in the sample and/or from single- or double-stranded nucleic acids in the sample, as described further herein. In some cases, a reverse transcriptase (e.g., SMARTer RT) and a DNA polymerase (e.g., Bst 2.0 DNA polymerase) are used together to mark nucleic acids with one or more non-templated nucleic acid residues (e.g., one or more A's, one or more C's, one or more G's, or one or more T's). The RT (e.g., SMARTer RT) may mark nucleic acids as originating from RNA by adding terminal one or more residues (e.g., one or more deoxycytidine residues) to the nascent strand. The DNA polymerase (e.g., Bst 2.0 DNA polymerase) may mark the nucleic acids as originating from DNA by adding one or more terminal residues that differ from the one or more residues used to mark the nucleic acids as originating from RNA (e.g., one or more deoxyadenine residues) to the nascent strand.

After formation of the duplex, a second adapter sequence 180 may be appended to the duplex 140, e.g., added as a double-stranded adapter to the end opposite to the end to which the first adapter is appended. The second adapter can be a double-stranded adapter with blunt ends or with at least one overhang nucleic acid residue. In some cases, the second adapter can comprise up to 10 overhang nucleic acid residues. In some other cases, the overhang residues are uniform (e.g., all C's or all A's). In some cases, the overhang residues may be specific for overhangs deposited by either the Reverse Transcription (RT) or DNA polymerase used in the primer extension reaction. Adapters with RT-specific overhangs may further contain an identifying sequence to mark the DNA as resulting from RNA in the starting sample. Likewise, adapters with DNA-polymerase specific overhangs may further contain an identifying sequence to mark DNA as originating from DNA in the starting sample.

The second adapter is generally composed of double-stranded DNA, but, in some cases, it may contain both DNA and RNA or be entirely made up of RNA. The second adapter sequence may be ligated to the double-stranded DNA in the reaction mixture using a DNA ligase such as, T4 DNA ligase and may be ligated to the RNA/DNA hybrid nucleic acids using a ligase such as T4 RNA Ligase 2. The second adapter may include additional functional sequences (e.g., one or more of amplification and sequencing primers, as well as attachment sequences). In some cases, the second adapter sequence can differentiate or identify the origin of the nucleic acid (e.g., RNA origin vs DNA origin).

A sequential or concurrent process can be used to ligate second adapter sequences to DNA-RNA hybrids or dsDNA using one or more ligases. For example, T4 DNA ligase can ligate to dsDNA and to DNA-RNA hybrids. To selectively ligate a second adapter sequence to one of dsDNA and DNA-RNA hybrids, sequential addition of the ligases (e.g., performing the ligation to DNA-RNA hybrids using a RNA ligase first) can be used or concurrent addition if the RNA ligase ligation rate on DNA-RNA hybrids is sufficiently higher that DNA ligase is not competitive for ligating to DNA-RNA hybrids.

In some cases, a sequential or successive process is used. In some cases, two or more types of second adapters (e.g., 2a adapter and 2b adapter) are used. The 2a adapter type may include a first code indicating a first nucleic acid (e.g., RNA) origin. The 2b adapter type may include a second code indicating a second nucleic acid (e.g., DNA) origin. The 2a type of second adapters can be mixed with the sample, and an RNA ligase such as T4 RNA Ligase 2 (truncated) can be added. The ligation reaction to ligate the 2a adapters to DNA:RNA hybrids can be performed. The sample can be washed to remove excess unligated 2a adapters to prevent 2a adapters from being ligated to dsDNA templates. If the 2a adapter ligation has ligation runs to completion, the wash step can be skipped if unligated 2a adapters are not present. The 2b adapters and a DNA ligase such as T4 DNA ligase can be added to ligate the 2b adapters to dsDNA. Alternatively, the ligation of the 2b adapters to the dsDNA can be performed first, followed by a wash step to remove excess unligated 2b adapters, and the ligation of the 2a adapters to the DNA:RNA hybrids can be performed. In general, the more selective or specific adapter ligation occurs first. The ligated sequences can be amplified and sequenced. The second adapter codes can be used to distinguish between RNA and DNA origins.

In some cases, a concurrent process can be used. For example, if the RNA ligase ligation rate on DNA-RNA hybrids is much higher than the ligation rate of the DNA ligase on DNA-RNA hybrids, the DNA ligase may not be competitive for the DNA-RNA hybrid template. In this case, the RNA ligase may selectively ligate the DNA-RNA hybrid and the DNA ligase may selectively ligate the dsDNA. In some cases, the 2a and 2b adapters may contain one or more residues in order to selectively hybridize to one or more overhang residues deposited by a DNA polymerase (e.g., Bst 2.0 DNA polymerase) on dsDNA or a RT (e.g., SMARTer RT) on DNA-RNA hybrids. In cases where the two or more types of second adapters selectively hybridize to their templates, ligases may be added concurrently.

The added second adapter sequences can be recognized by a primer in order to prime primer extension and amplification of the nucleic acid fragments 150. Generally, the primer used in such amplification reaction is a DNA or RNA primer that is complementary to the sequence of the second adapter.

In some cases, ligation of a second adapter is not used in the method. Instead, the second adapter may be introduced during the amplification stage (e.g., 150, the first PCR cycle). For example, the second adapter itself may behave as a primer that recognizes one or more non-templated nucleic acids residues added to the end of a strand by a polymerase such as SMARTer RT or Bst 2.0. As such, the second adapter may contain an adapter sequence domain as well as a domain that recognizes the one or more non-templated nucleic acid residues such as one or more C's (e.g., C, CC, CCC, CCCC, CCCCC, or CCCCCC) or one or more A's (e.g., A) added by the polymerase. The adapter then primes replication during amplification 150, resulting in incorporation of the adapter sequence into the resulting amplified DNA molecules.

The nucleic acid products of the methods provided by the present disclosure may be detected and/or analyzed by any method known in the art. In some cases, a sequencing assay is performed. In some cases, a real-time PCR reaction is performed. In some cases, a microarray-based assay is performed. In some cases, a digital PCR assay is performed. A person skilled in the art will also recognize when new tools developed can be applied for the analysis of amplified DNA or RNA molecules.

Analysis of the sequencing results may enable detection of RNA and DNA in the originating sample, without necessarily distinguishing between the two types of nucleic acids. In some cases, however, the analysis is used to trace the identity of the originating nucleic acid (e.g., double-stranded vs. single-stranded, RNA vs. DNA).

In some cases, the second adapter sequence can comprise a sequencing adapter. In some cases, the second adapter sequence can comprise a primer binding site recognized by a PCR primer, and the PCR primer can also contain a sequencing primer (e.g., Illumina P5 amplification primer sequence or Illumina P7 amplification primer sequence). In some cases, the primer binding site on the second adapter is near or at the 5' end.

In general, each enzymatic step (e.g., first ligation, primer extension, second ligation, pre-denaturation ligation, etc.) can be performed using one of three approaches: a single enzyme, successive enzyme addition, or concurrent enzyme addition. In some cases, a single enzyme is used in one or more enzymatic steps. In some cases, the single enzyme is not selective between RNA and DNA templates. In some cases, successive enzyme addition of two or more enzymes is used in one or more enzymatic steps. In some cases, the first enzyme that is added is selective for a first nucleic acid (e.g., DNA vs. RNA and/or single-stranded vs. double-stranded). In some cases, the second enzyme that is added is either selective for a second nucleic acid or not selective. In some cases, concurrent enzyme addition of two or more enzymes is used in one or more enzymatic steps. In some cases, the two or more enzymes are selective for different nucleic acid forms. In some cases, one enzyme has higher selectivity and also has higher activity, and the second enzyme is not selective or weakly selective. In some cases, the two or more enzymes are weakly selective or not selective.

The approaches provided herein are generally superior to nucleic acid analyses that typically focus on a single chemically and structurally uniform nucleic acid, e.g., only ssDNA, dsDNA, ssRNA, dsRNA, or mRNA, etc. Analysis of a single form may be easier because the different forms generally may have different processing needs (reagents, enzymes, cofactors, etc.). However, the results in any given analysis provide only a partial readout of the nucleic acids present in a given sample.

III. Samples and Analytes

A. Samples

The disclosed methods, systems, compositions, and kits can be used for the analysis of a wide range of different sample types. The disclosure may be particularly useful in the evaluation of samples in which the level of nucleic acids are of low quality or quantity, by allowing analysis of a larger fraction of the nucleic acids present in that sample, regardless of chemical type or structure.

In some cases, a sample can contain cells, tissue, or a bodily fluid. In some embodiments, a sample can be a liquid or fluid sample. In some cases, a sample can contain a body fluid such as whole blood, plasma, serum, urine, stool, saliva, lymph, spinal fluid, synovial fluid, bronchoalveolar lavage, nasal swab, respiratory secretions, vaginal fluid, amniotic fluid, semen or menses. In some cases, a sample can be made up of, in whole or in part, cells and/or tissue. In some cases, a sample can be made up of a cell-free sample. In some cases, a sample may comprise nucleic acids (e.g., DNA, RNA, etc.) extracted or purified from a sample (e.g., a clinical sample).

In analyzing genetic composition of a sample (e.g., tissue, blood, serum, etc.) the sample lysis, processing, and extraction of nucleic acid fraction can require different processing steps, buffer solutions, and enzyme systems for the lysis and isolation of the nucleic acid product. The methods for processing such different samples types (e.g., tissue, blood, serum, etc.) are own in the art.

In some embodiments, the obtained sample is a cell-free sample taken from a body fluid such as blood, serum, plasma, lymph, urine, or saliva. The cell-free sample may comprise nucleic acids that originated from a different site in the body, such as a site of pathogenic infection. In the case of blood, serum, lymph, or plasma, the cell-free sample may contain "circulating" cell-free nucleic acids that originated at a different location. In the case of urine, the cell-free nucleic acids may be "traveling" cell-free nucleic acids that traveled to the urine from a different site in the body. The cell-free samples can be obtained by removing cells, cell fragments, or exosomes by a known technique such as by centrifugation or filtration. Samples herein may be biological samples.

In some cases, a sample can be circulating tumor or fetal nucleic acids. Analysis of serum or blood borne nucleic acids, such as circulating tumor or fetal nucleic acids, e.g., as described in U.S. Pat. Nos. 8,877,442 and 9,353,414, or in pathogen identification through, e.g., analysis of circulating microbial or viral nucleic acids, e.g., as described in Published U.S. Patent Application No. 2015-0133391 and Published U.S. Patent Application No. 2017-0016048, the full disclosures of each is incorporated herein by reference in its entirety for all purposes.

B. Subjects

A sample can be obtained from any subject (e.g., a human subject, a non-human subject, etc.). The subject can be healthy. In some cases, the subject is a human patient having, suspected of having, or at risk of having, a disease or infection.

A human subject can be a male or female. In some embodiments, the sample can be from a human embryo or a human fetus. In some embodiments, the human can be an infant, child, teenager, adult, or elderly person. In some cases, the subject is a female subject who is pregnant, suspected of being pregnant, or planning to become pregnant.

In some embodiments, the subject is a farm animal, a lab animal, or a domestic pet. In some embodiments, the animal can be an insect, dog, a cat, a horse, a cow, a mouse, a rat, a pig, a fish, bird, a chicken, or a monkey.

The subject can be an organism, such as a single-celled or multi-cellular organism. In some embodiments, the sample may be obtained from a plant, fungi, eubacteria, archeabacteria, protest, or any multicellular organism. The subject may be cultured cells, which may be primary cells or cells from an established cell line.

In some embodiments, the subject has a genetic disease or disorder, is affected by a genetic disease or disorder, or is at risk of having a genetic disease or disorder. A genetic disease or disorder can be linked to a genetic variation such as mutations, insertions, additions, deletions, translocation, point mutation, trinucleotide repeat disorders, single nucleotide polymorphisms (SNPs), or a combination of genetic variations.

The sample can be from a subject who has a specific disease, condition, or infection, or is suspected of having (or at risk of having) a specific disease, condition, or infection. For example, the sample can be from a cancer patient, a patient suspected of having cancer, or a patient at risk of having cancer. In other cases, the sample can be from a patient with an infection, a patient suspected of an infection, or a patient at risk of having an infection.

C. Analytes

The disclosure provides for the concurrent detection and genetic analysis of various chemical and structural analytes found in a biological sample. Analytes can include various chemical forms of a DNA molecule as well as various forms of a RNA molecule. Analytes can also include various forms different structural forms of DNA and RNA found in a sample. In some embodiments, the analytes can be particle free (e.g., such as cell-free). In some embodiments, the analytes can be intact (e.g., exsomes or encapsulated).

Analytes may be any type of nucleic acid including but not limited to: double-stranded (ds) nucleic acids, single stranded (ss) nucleic acids, DNA, RNA, cDNA, mRNA, cRNA, tRNA, ribosomal RNA, dsDNA, ssDNA, miRNA, siRNA, circulating nucleic acids, circulating cell-free nucleic acids, circulating DNA, circulating RNA, cell-free nucleic acids, cell-free DNA, cell-free RNA, circulating cell-free DNA, cell-free dsDNA, cell-free ssDNA, circulating cell-free RNA, genomic DNA, exosomes, cell-free pathogen nucleic acids, circulating pathogen nucleic acids, mitochondrial nucleic acids, non-mitochondrial nucleic acids, nuclear DNA, nuclear RNA, chromosomal DNA, circulating tumor DNA, circulating tumor RNA, circular nucleic acids, circular DNA, circular RNA, circular single-stranded DNA, circular double-stranded DNA, plasmids, bacterial nucleic acids, fungal nucleic acids, parasite nucleic acids, viral nucleic acids, cell-free bacterial nucleic acids, cell-free fungal nucleic acids, cell-free parasite nucleic acids, viral particle-associated nucleic acids, viral-particle free nucleic acids or any combination thereof. Analyte nucleic acids may be nucleic acids derived from pathogens including but not limited to viruses, bacteria, fungi, parasites and any other microbe, particularly an infectious microbe. In some cases, nucleic acids may be derived directly from the subject, as opposed to a pathogen.

In some instances, the present disclosure provides for analysis of single-stranded nucleic acids. The single-stranded methods provided by the present disclosure can be applied for more efficient processing of shorter nucleic acid fragments. In some cases, the single-stranded nucleic acids methods, composition, systems, and kits can be applied for pathogen identification in samples that contain circulating or cell-free nucleic acids or highly degraded or low-quality samples such as ancient, formalin-fixed paraffin-embedded (FFPE) samples, or samples which have undergone many freeze-thaw cycles.

In some instances, the present disclosure provides for analysis of both double-stranded and single-stranded nucleic acids in a sample. In some cases, the subject may have, or be suspected of having, a pathogenic infection. In this case, the sample from the host subject comprises the host DNA and RNA, as well as DNA and RNA from a pathogen which can be in the chemical or structural form of ssRNA, ssDNA, dsRNA, or dsDNA. The present disclosure provides, in some cases, concurrent detection and quantitative analysis of all the nucleic acid forms in an original sample regardless of their form at the detection stage.

D. Extraction of Analytes

In the methods provided herein, nucleic acids can be isolated from a sample using any methods or approaches known in the art. For example, nucleic acids can be extracted using liquid extraction (e.g., Trizol, DNAzol) techniques. Nucleic acids can also be extracted using commercially available kits (e.g., QIAamp Circulating Nucleic Acid Kit, Qiagen DNeasy kit, QIAamp kit, Qiagen Midi kit, QIAprep spin kit).

Nucleic acids can be concentrated or precipitated by known methods, including, by way of example only, centrifugation. Nucleic acids can be bound to a selective membrane (e.g., silica) for the purposes of purification. Nucleic acids can also be enriched for fragments of a desired length, e.g., fragments which are less than 1000, 500, 400, 300, 200 or 100 base pairs in length. Such an enrichment based on size can be performed using, e.g., PEG-induced precipitation, an electrophoretic gel or chromatography material (Huber et al. (1993) Nucleic Acids Res. 21:1061-6), gel filtration chromatography, or TSKgel (Kato et al. (1984) J. Biochem, 95:83-86), which publications are hereby incorporated by reference in their entireties for all purposes.

A nucleic acid sample can be enriched for target polynucleotides (e.g. target nucleic acids), particularly target nucleic acids associated with condition, disease, or infection and/or a target tissue type. Target enrichment can be by any means known in the art. For example, the nucleic acid sample may be enriched by amplifying target sequences using target-specific primers (e.g., primers specific for pathogen nucleic acids). The target amplification can occur in a digital PCR format, using any methods or systems known in the art. The nucleic acid sample may be enriched by capture of target sequences onto an array immobilized thereon target-selective oligonucleotides. The nucleic acid sample may be enriched by hybridizing to target-selective oligonucleotides free in solution or on a solid support. The oligonucleotides may comprise a capture moiety which enables capture by a capture reagent. In some embodiments, the nucleic acid sample is not enriched for target polynucleotides, e.g., represents a whole genome.

In some embodiments, nucleic acids can be enriched by a pull-down method. In some cases, nucleic acids can be hybridized to complementary oligonucleotides conjugated to a label such as a biotin tag and using, for example, avidin or streptavidin attached to a solid support), targeted PCR, or other methods. Examples of enrichment techniques that can be used include but are not limited to: (a) self-hybridization techniques in which the major population in a sample of nucleic acids self-hybridizes more rapidly than the minor population in the sample; (b) depletion of nucleosome-associated DNA from free DNA; (c) removing and/or isolating DNA of specific length intervals; (d) exosome depletion or enrichment; and (e) strategic capture of regions of interest.

Fragmentation & End Modification

The methods can include fragmenting the nucleic acids. In some applications, the methods do not include fragmenting the nucleic acids, such as, in application with low quality samples or samples containing short fragments such as certain samples containing cell-free nucleic acids.

Fragmenting of the nucleic acids may be performed by e.g., mechanical shearing, passing the sample through a syringe, sonication, heat treatment, or a combination thereof. In some cases, shearing may be performed by mechanical shearing (e.g. ultrasound, hydrodynamic shearing forces), enzymatic shearing (e.g. endonuclease), thermal fragmentation (e.g. incubation at high temperatures), chemical fragmentation (e.g. alkaline solutions, divalent ions). In some cases, fragmenting can be performed by using an enzyme, including a nuclease, or a transposase. Nucleases used for fragmenting may comprise restriction endonucleases, homing endonucleases, nicking endonucleases, high fidelity restriction enzymes, or any enzyme disclosed herein. The methods may comprise fragmenting the target nucleic acids into fragments of certain length, e.g., 10, 25, 50, 60, 80, 100, 120, 140, 160, 200, 500, or 1000 bp or greater in length.

The lengths of the nucleic acids may vary. The nucleic acids or nucleic acid fragments (e.g., dsDNA fragments, RNA, or randomly sized cDNA) can be less than 1000 bp, less than 500 bp, less than 200 bp, or less than 100 bp. The DNA fragments can be about 40 to about 100 bp, about 50 to about 125 bp, about 100 to about 200 bp, about 150 to about 400 bp, about 300 to about 500 bp, about 100 to about 500, about 400 to about 700 bp, about 500 to about 800 bp, about 700 to about 900 bp, about 800 to about 1000 bp, or about 100 to about 1000 bp or more. In some cases, the nucleic acids or nucleic acid fragments (e.g., dsDNA fragments, RNA, or randomly sized cDNA) can be within the range from about 20 to about 200 bp, such as within the range from about 40 to about 100 bp.

The ends of dsDNA fragments can be polished (e.g., blunt-ended). The ends of DNA fragments can be polished by treatment with a polymerase. Polishing can involve removal of 3' overhangs, fill-in of 5' overhangs, or a combination thereof. The polymerase can be a proofreading polymerase (e.g., comprising 3' to 5' exonuclease activity). The proofreading polymerase can be, e.g., a T4 DNA polymerase, Pol 1 Klenow fragment, or Pfu polymerase. Polishing can comprise removal of damaged nucleotides (e.g., abasic sites), using any means known in the art.

IV. Denaturation

The methods of the disclosure can include the denaturing of nucleic acids from a sample. The denaturation may cause all or most of the double-stranded nucleic acids within the sample to become single-stranded. In some cases, the denaturation removes secondary or tertiary structure from double-stranded or single-stranded nucleic acids. As such, any type of sample may be subjected to the denaturation step, including samples that contain only double-stranded nucleic acids, only single-stranded nucleic acids, or a mixture of double-stranded and single-stranded nucleic acids. In some cases, the single-stranded nucleic acids in the sample are there as a result of being subjected to denaturation. In some cases, however, the nucleic acids in the sample are single-stranded because they were originally single-stranded when they were obtained from the subject, e.g., single-stranded viral genomic RNA or single-stranded DNA.

A. Heat

The nucleic acids may be denatured using any method known in the art. In some cases, the denaturation is accomplished by applying heat to the sample for an amount of time sufficient to denature double-stranded nucleic acids or to denature secondary and tertiary structures of double-stranded or single-stranded nucleic acids. In general, the sample may be denatured by heating at 95° C., or within a range from about 65 to about 110° C., such as from about 85 to about 100° C. Similarly, the sample may be heated for any length of time sufficient to effectuate the denaturation, e.g., from about 10 seconds to about 60 minutes. In some cases, long nucleic acids such as intact dsRNA viruses may require longer denaturation times. In general, the denaturation is performed in order to ensure that all or most of the nucleic acids within a sample are present in single-stranded form.

In some cases, the denaturation may remove secondary and tertiary structures in single-stranded DNA and/or RNA molecules. Non-limiting examples of domains of secondary structure that may be removed during the denaturation step in include hairpin loops, bulges, and internal loops and any element contributing to folding of the molecule. In some cases, denaturation may not need to be performed, for example when the sample is known to contain only single-stranded nucleic acids or when there is a desire to restrict the ultimate analysis to only the single-stranded and not the double-stranded nucleic acids in the sample.

B. Chemical and Mechanical

Depending on the application, chemical or mechanical denaturing can be used (e.g., sonication or the like) with the methods.

Chemical denaturation agents that can be used with the methods of the disclosure include but are not limited to, alkaline agents (e.g. NaOH), formamide, guanidine, sodium salicylate, dimethyl sulfoxide (DMSO), propylene glycol, or urea.

V. Adapter Attachment

The adapters may be attached to the nucleic acids in a sample at one or more points during the sample preparation process. In some cases, the adapters may be attached by a ligation reaction or by a primer extension reaction or a combination of both of these reaction types.

In some cases, the adapters may be attached by the ligation reaction method using a ligase enzyme that recognizes a particular nucleic acid form or by a primer extension reaction method using a PCR reaction, where the adapter also acts as a primer for a polymerase which acts on a particular nucleic acid form.

Depending on the contents of the sample and the goal of the genetic assay, the first and second adapters, or iterations using more than two adapters, can be attached using various different schemes. In some applications, the first and second adapters, or successive iterations of adapters, may be attached to ssDNA, dsDNA, ssRNA, dsRNA, DNA, RNA, or DNA/RNA hybrid molecules, or in any combination. Depending on the type of nucleic molecule in the sample the adapter attached can be either double-stranded or single-stranded such that the adapter is compatible with the nucleic molecules in the sample. For example, in some cases a double-stranded adapter is attached to a double-stranded nucleic acid. In some applications, it is desirable to protect the adapter ends, for example by providing an adapter that is duplexed on one end (or double-strande) and single-stranded on the other end.

In some adaptor attachment schemes, the first and second adapters can be both attached using a ligation reaction. In another case, the first and second adapters are both attached using a primer extension reactions. In some cases, the first adapter can be attached by ligation reaction and the second adapter is attached by primer extension reaction. In some cases, the first adapter can be attached by primer extension and the second adapter can be attached by a ligation reaction.

The primer extension reactions can be carried out by a DNA-dependent polymerase or a RNA dependent polymerase or a combination thereof. In some cases, the primer extension reaction can be carried out by a DNA or RNA polymerase having strand displacing activity. In some cases, the primer extension reaction is carried out by a DNA or RNA polymerase that has non-templated activity. In some other cases, the primer extension reaction can be carried out by a DNA or RNA polymerase having strand displacing activity and a DNA or RNA polymerase that has non-templated activity.

A. Adapter Compositions

The present disclosure also provides adapter compositions. In general, the adapter compositions allow for the detection of different nucleic acid forms in a sample. Depending on the starting sample type, what nucleic acid(s) are being analyzed, the method, and what detection system is being used, an appropriate adapter can be employed (e.g., particular functional elements or modifications).

In general, an adapter can comprise a polymerase priming sequence, a sequence priming sequence, and one or more identifying sequences (e.g., such as an index, a barcode, a non-templated overhang, a random sequence, or a combination thereof). For other applications, an adapter can comprise a polymerase priming sequence, a sequence priming sequence, and one or more identifying sequences, and a label (e.g., radioactive phosphates, biotin, fluorophores, or enzymes). Labels can be added to an adapter if a purification step or particular detection system is desired (e.g., digital PCR, ddPCR, quantitative PCR, microfluidic device, microarray).

In some applications, the adapter can comprise a polymerase priming sequence, one or more identifying sequences, or a label. In other applications, as adapter can comprise a polymerase priming sequence, a sequence priming sequence, one or more identifying sequences, or a label (e.g., radioactive phosphates, biotin, fluorophores, or enzymes). In some applications, the first or second adapter does not comprise a label.

The adapter may be single-stranded or double-stranded. In some cases, the adapter may be a RNA molecule, a DNA molecule, or contain both DNA and RNA (e.g., DNA/RNA hybrid). In some cases, a double-stranded adapter may be blunt-ended. In other cases, a double-stranded adapter may contain nucleic acid residue overhang. Such nucleic acid residue overhangs (or tails) may be used to mark a molecule as originating from DNA or RNA in the starting sample (e.g. FIG. 1, 100), particularly when the overhangs are complementary to an overhang sequence deposited by a RT (e.g., SMARTer RT) and/or a DNA polymerase (e.g., Bst 2.0 DNA polymerase). For example, the adapter overhang may contain one or more T residues in order to hybridize to one or more overhang residues deposited by a DNA polymerase (e.g., Bst 2.0 DNA polymerase or the like). Similarly, the adapter overhang may contain one or more G residues in order to hybridize to one or more overhang residues deposited by a RT (e.g., SMARTer RT or the like).

In some applications, the first adapter can be single-stranded or second adapter can be double-stranded. In some applications, the first adapter can be double stranded, or second adapter can be double stranded. In some applications, the first and second adapter may contain additional functional sequences (e.g., one or more of amplification and sequencing primers, as well as attachment sequences). In some cases, the adapter sequence contains a barcode or index to indicate whether a nucleic acid derives from a RNA or DNA in the starting sample.

The disclosure also provides for various modifications at the ends of the adapters of the present disclosure for better functionality or compatibility with a particular method and/or assay.

Adapters with Amino Modification

The disclosure provides adapters with amino modifiers (e.g., 3AmMO, /5AmMC6/ or /5AmMC12/). A primary amino group can be attached to an oligonucleotide. Amino modifiers can be positioned at the 5'-end with either a standard (C6) or longer (C12) spacer arm. Amino modifications can be positioned at the 3'-end. An example of such as adapter is SEQ ID NO:14, a splinted ligation adapter: /5Sp9/AA/iSp9/CTTCCGATCTNNNNNN/3AmMO/ combined with SEQ ID NO 15.

Adapters with an Adenylated Oligo Modification

The disclosure provides for adapters with 3' end blocking by dideoxycytosine (ddC). ddC is a dideoxyribonucleoside, a synthetic analog of deoxycytosine. In ddC, both the 2'- and 3'-positions of the ribose have a hydrogen (—H) group substituted for the —OH group, whereas in dC, only the 2'-position is so substituted.

The ddC modification can be used to block the 3'-end of 5'-adenylated oligos. This type of adapter is useful for to prevent unwanted extension by a polymerase in a PCR reaction or PCR-based assay. In some embodiments, the adapter can be a 3'-Spacer C3 /3SpC3/. In some embodiments, the adapter can be a dideoxycytosine /3ddC/ is used.

An example of a 3' end blocking adapter is SEQ ID NO: 2 CGACGCTCTTC/3ddC/ SEQ ID NO:1 GTGACTGGAGTTCAGACGTGTGCTCTTCCGATCT Adapters with Phosphate Group Modification The disclosure provides adapters that are modified by one or more phosphate groups (e.g., /5Phos/). An adapter having 5' phosphorylation can be used where the oligo is used as a substrate for DNA ligase. An adapter having 3' phosphorylation can be used to inhibit degradation by some 3'-exonucleases and can to block extension by DNA polymerases.

An example of such as adapter is SEQ ID NO: 4 /5Phos/AGATCGGAAG/iSpC3/iSpC3/iSpC3/iSpC3/iSpC3/iSpC3/iSpC3/iSpC3/iSpC3/iSpC3/3Bio TEG/.

Adapters with *GA*TC*T Modification

The disclosure provides for adapters modified with a *GA*TC*T sequence at the ends. An example of such as adapter is SEQ ID NO: 5 GTGACTGGAGTTCAGACGTGTGCTCTTCC*GA*TC*T. where * indicate the location of phosphothiodiester bond between the neighboring nucleotides in the sequence.

Adapters with *T*G*T*A Modification

The disclosure provides for adapters modified with a *T*G*T*A sequence at the ends. An example of such as adapter is SEQ ID NO: 3 5Phos/GGAAGAGCGTCGTGTAGGGAAAGAG*T*G*T*A. where * indicate the location of phosphothiodiester bond between the neighboring nucleotides in the sequence.

Non-limiting examples of adapters that can be used with the disclosure are provided herein. In some embodiments, an extension primer can be composed of a sequence reverse complementary to the entire or part of the 3'-end adapter. In some cases, the sequence can have a 3'-end and 5'-end hydroxyls, and may be protected against 3'-end exonuclease activity of some DNA-dependent polymerases (e.g. Large Klenow Fragment) by chemical modifications (e.g. phosphothiodiester bond). An example of the sequence is e.g. SEQ ID NO: 1 GTGACTGGAGTTCAGACGTGTGCTCT-TCCGATCT. An equivalent sequence protected against 3'-exonuclease activity by Large Klenow Fragment may be SEQ ID NO: 5 GTGACTGGAGTTCAGACGTGTGCTCTTCC*GA*TC*T, where * indicate the location of phosphothiodiester bond between the neighboring nucleotides in the sequence.

In some embodiments, a second adapter (i.e. 5'-end adapter) may be composed of two oligos that are full or partial reverse complements of each other. The oligos that is actively ligated to the nucleic acid template has 5'-end phosphate, and is protected against degradation by phosphothiodiester bonds at its 3'-end (e.g. SEQ ID NO: 3 5Phos/GGAAGAGCGTCGTGTAGGGAAAGAG*T*G*T*A). Its hybridizing partner may be partial or full-length reverse complement with 3'-end deactivated against ligation (e.g. SEQ ID NO: 2 CGACGCTCTTC/3ddC/).

In some embodiments, a single-stranded 3'-end adapter contains a phosphorylated 5'-end with its 3'-end deactivated against ligation. The oligo can contain a moiety that can be used for immobilization purposes (e.g. biotin, digoxigenin, antigen). An example of such a sequence is SEQ ID NO: 4 /5 Phos/AGATCGGAAG/iSpC3/iSpC3/iSpC3/iSpC3/iSpC3/iSpC3/iSpC3/iSpC3/iSpC3/3Bio TEG/.

In some embodiments, an amplification forward primer for indexing PCR can contain a 3'-end region that binds the second adapter attached at the 5'-end side of the original template. The sequence may also contain an index region. For example, SEQ ID NO: 6 AATGATACGGCGACCAC-CGAGATCTACACcctgcgaACACTCTTTCCCTACAC-GACGCTCT T/ where index region is indicated with a lower case font.

In some embodiments, an amplification reverse primer for indexing PCR can contain a 3'-end region that binds the first adapter attached at the 3'-end side of the original template. The sequence may also contain an index region. For example, SEQ ID NO: 10 CAAGCAGAAGACGGCATAC-GAGATatcttgcGTGACTGGAGTTCAGACGTGT where index region is indicated with a lower case font.

In some embodiments, the first adapter (i.e. the adapter that attaches to the 3'-end of the original template) may be attached by splint ligation where a splint oligo is hybridized to e.g. SEQ ID NO: 4. The necessary properties of the splint oligos are deactivated 3'- and 5'-ends disabling ligation to the splint oligo. In addition, the 3'-end sequence is randomized containing at least 3 random positions. Finally, the 5'-end is fully or partially reverse complementary to the very 5'-end of the 3'-end adapter sequence. An example of such sequence may be ID NO:14 /5 Sp9/AA/iSp9/CTTC-CGATCTNNNNNN/3AmMO/. Notation of the modifications adopted from IDT website.

B. Amplification Element

An adapter can comprise an amplification primer that is a primer used to carry out a polymerase chain reaction (PCR). In some cases, the amplification primer may be a random primer. In some cases, the amplification primer can be a template-specific primer. In other cases, the amplification primer can be complementary to a known non-templated overhang known to be added by the polymerase. In some cases, the amplification primer is a P5 primer. In some cases, the amplification primer is a P7 primer. In some cases, the amplification primer only part of a P5 or P7 primer. In some cases, depending on the method of detection the amplification primer can comprises or more additional functional elements.

C. Identifying Sequence Element

Generally, the identifying sequence elements (e.g., barcode, index, or a combination thereof) comprise a unique sequence. The identifying sequence element can be added to a particular nucleic acid form by the methods provided herein (e.g., ligation, primer extension or a combination thereof) allowing the identification of each nucleic acid form in a sample. In some embodiments, the identifying sequence element may also contain additional functional elements such as primer amplification sites, sequencing priming sites, or sample indexes.

The identifying sequence element or barcodes can be completely scrambled (e.g., randomers of A, C, G, and T for DNA or A, C, G, and U for RNA) or they can have some regions of shared sequence. For example, a shared region on each end may reduce sequence biases in ligation events. In some cases, a shared region can be about or at least about 1, 2, 3, 4, 5, 6, 7, 8, 9, 10, 15, or 20 common base pairs. Combinations of barcodes can be added to increase diversity. For example, barcodes can be used as identifiers for well position in a microtiter plate, array, or the like (e.g., 96 different barcodes for a 96-well plate), and another barcode can be used as an identifier for a plate number (e.g., 24 different barcodes for 24 different plates), giving 96×24=2,304 combinations using 96+24=120 sequences. Using three or more barcodes per sample can further increase the achievable diversity. In some cases, barcodes may be about or at least about 2, 3, 4, 5, 6, 7, 8, 9, 10, 15, 16, 17, 18, 19, 20, 30, 40, 50, 60, 70, 80, 90, 100, 110, 120, 130, 140, 150, 160, 170, 200, 250, 300, 350, or 400, 500, or 1000 nucleotides (or base pairs) in length.

Non-Templated Primer Extension to Mark Originating Nucleic Acids

In some embodiments, the identifying sequence elements can be non-templated nucleotides that have been added during a primer extension reaction using a polymerase that has non-templated activity. The non-templated nucleotides can be any nucleotide such as one or more A, G, C, T, or U in any number and in any sequence.

Figure 7:
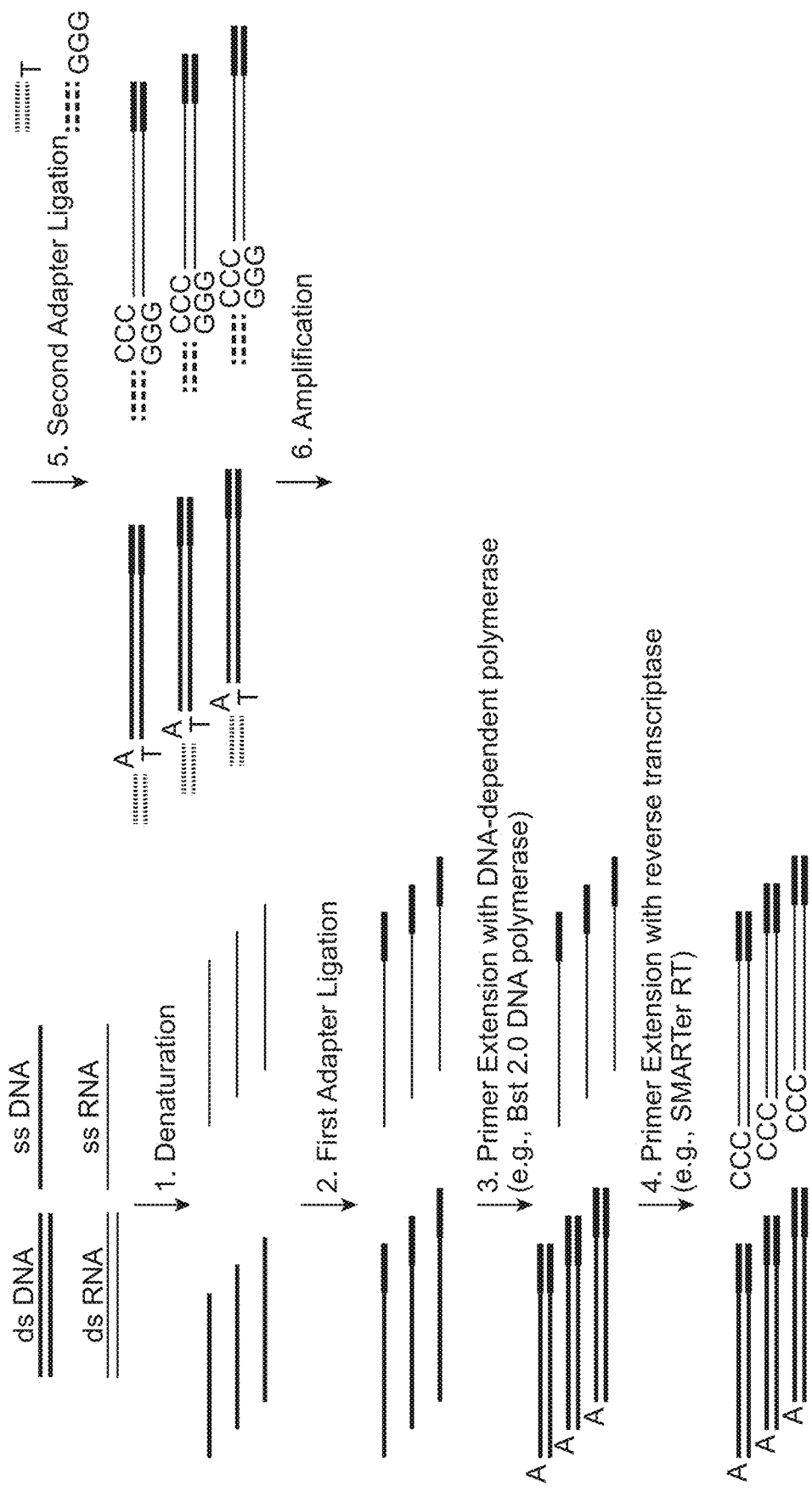
FIG. 7 depicts exemplary primer extension-non-templated approaches using a successive mode.
Figure 17:
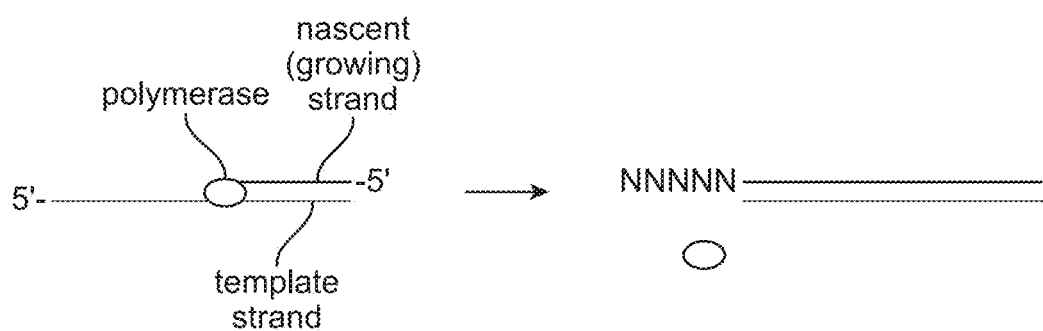
FIG. 17 illustrates the activity of polymerases having non-template activity. The non-templated nucleotides are indicated by "NNNNN", where N could be any nucleotide and any number of Ns can be used. In this illustration, the non-templated nucleotides are added to the 3' end of the nascent growing strand.

The methods provided herein may include tagging nucleic acids methods (e.g. identification sequences) that allow for subsequent identification of those sequences deriving or originating from DNA and/or RNA fragment templates in the sample. This is helpful when one wants to determine where the nucleic acid originally came from DNA or RNA. In some cases, such tagging occurs during the primer extension step by using a reverse transcriptase (RT) or DNA polymerase that append one or more unique non-templated nucleic acid residues to the end, or tail, of the extended nucleic acid strand (FIG. 17). The RT can be any RT that adds one or more non-templated nucleic acids to the extended nucleic acid strand (e.g., "nascent" strand, cDNA strand). In some cases, the RT is a Moloney Murine Leukemia Virus (MMLV) RT. In some embodiments, the RT is a SMARTer RT enzyme. In particular, a SMARTer RT enzyme typically appends anywhere from 1 to 6 non-templated deoxycytidine residues at the terminus of the replicated strand, as shown in FIG. 7 (step 4) and FIG. 18, which can serve as a tag or marker of replicated RNA. In some cases, the RT (e.g., SMARTer enzyme) is used together with a DNA polymerase that adds a different set of non-templated nucleic acid residues to the end of the primer extension product. The DNA polymerase can be any DNA polymerase known to add one or more non-templated nucleic acid residues to the nascent strand including *Bacillus stearothermophilus* DNA polymerase I, which owing to a lack of 3'-5' exonuclease activity, leave 3' overhangs. As shown in FIG. 7 (step 3), the polymerase may be Bst 2.0 DNA polymerase, which adds one or more non-templated adenine (A) residues to the nascent strand. However, in some cases, the RT is used on its own to mark sequences originating from a RNA fragment in the absence of a marking DNA polymerase.

Similar to the SMARTer RT enzyme, the Bst-polymerase likewise has been shown to add one or more non-templated adenosine residues to the terminus of the replicated fragment (or nascent strand), again, providing a basis for identifying that which originates from an RNA or DNA template, either by direct detection or by priming with an appropriate tagging sequence. Use of the SMARTer RT enzyme or Bst polymerase in combination may thus enable differentiation of starting DNA from starting RNA. In some cases, only one polymerase capable of adding one or more non-templated nucleotides is used in the reaction. For example, SMARTer RT may be used with a DNA polymerase that does not add non-templated nucleic acids. Adapters recognizing the dC residues added by the SMARTer RT may be used in combination with blunt adapters that recognize the DNA originally derived from the starting DNA in the reaction mixture. Conversely, adapters recognizing the dA residues added by the Bst polymerase may be used in combination with blunt adapters that recognize the DNA originally derived from the starting RNA in the reaction mixture.

FIG. 7 provides an exemplary scheme for differentiation of starting RNA from starting DNA using successive primer extension with DNA polymerase and reverse transcriptase. As shown, the nucleic acids in the sample may be subjected to denaturation, e.g., through application of heat, (step 1) to ensure that all nucleic acids are present in single-stranded form. In some cases, denaturation may not need to be performed, for example when the sample is known to contain only single-stranded nucleic acids or when there is a desire to restrict the ultimate analysis to only the single-stranded and not the double-stranded nucleic acids in the sample.

The single-stranded nucleic acids (DNA and/or RNA) may be then subjected to a first adapter ligation step (step 2), to append a first single-stranded adapters to the 3' end of the nucleic acid strand. The first adapter may contain additional functional sequences (e.g., one or more of amplification and sequencing primers, as well as attachment sequences).

Primers specific for the appended adapters may be used to prime replication of the DNA, using a DNA polymerase (e.g., Bst 2.0 DNA polymerase), to create DNA duplexes (step 3) tagged with one or more non-templated nucleic acid residues (e.g., one or more dA) at the 3' end of the extended strand. Primers specific for the appended adapters may also be used to prime reverse transcription of the RNA, using a reverse transcriptase (e.g., SMARTer RT), to create cDNA duplexes (step 4) tagged with one or more non-templated nucleic acid residues (e.g., 1-6 dC residues).

The DNA polymerase-catalyzed primer extension and the reverse transcriptase-catalyzed primer extension may be performed in any order. For example, the DNA polymerase-catalyzed primer extension may be performed (e.g., using Bst 2.0 DNA polymerase) before the reverse transcriptase-catalyzed primer extension (e.g., using SMARTer RT). Alternatively, the DNA polymerase-catalyzed primer extension may be performed after the reverse transcriptase-catalyzed primer extension.

Figure 8:
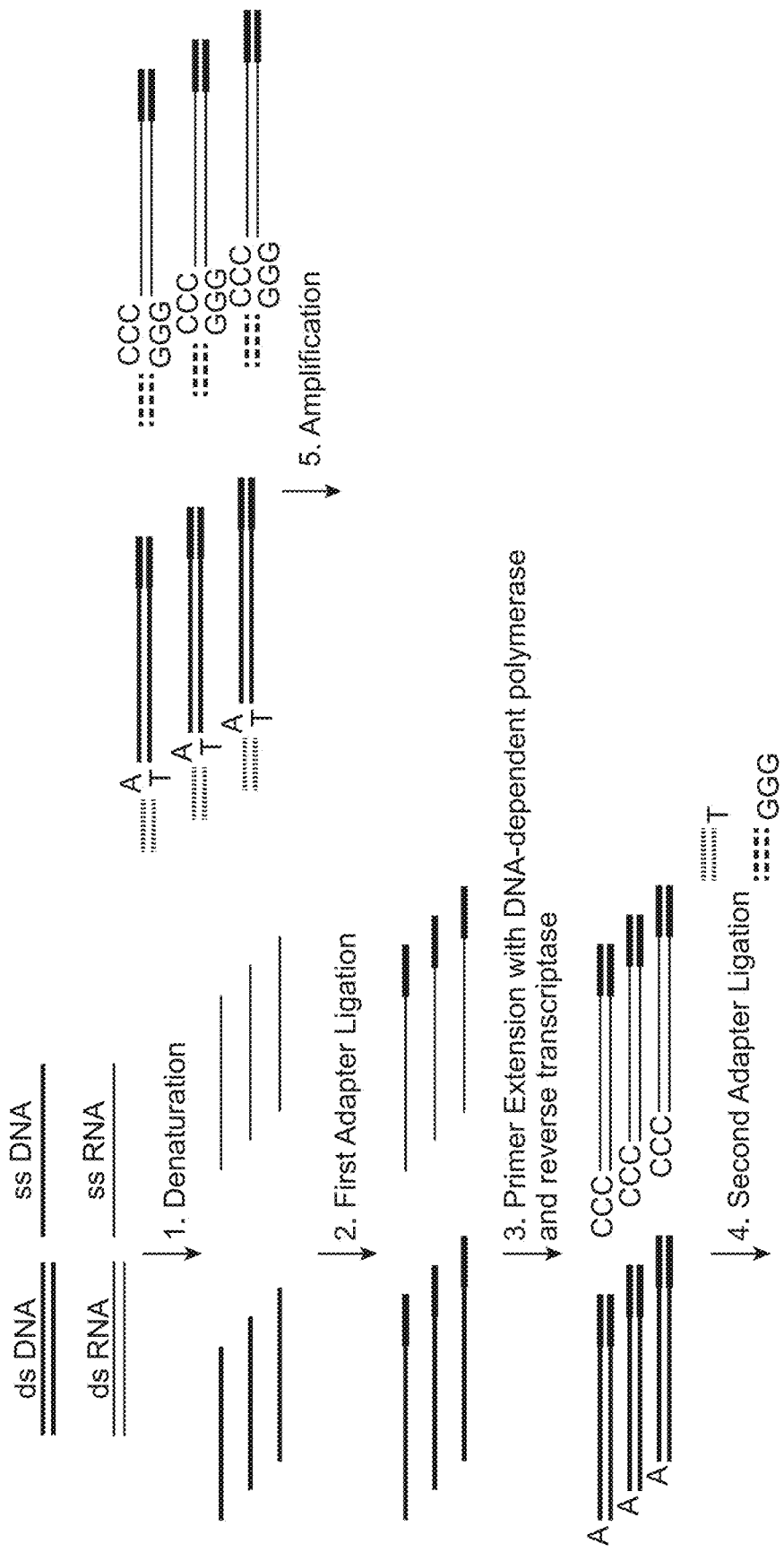
FIG. 8 shows exemplary primer extension-non-templated approaches using a concurrent mode.

In some embodiments, the primer extension (step 3 above) may be performed using a DNA polymerase and a reverse transcriptase concurrently, as shown in FIG. 8. This approach may be performed by concurrently using a pair of DNA polymerase (e.g., Bst 2.0 DNA polymerase) and reverse transcriptase (e.g., SMARTer RT) that show specificity for DNA and RNA templates, respectively (FIG. 8, step 3).

The resulting DNA duplexes and/or the cDNA duplexes from both the above successive and concurrent methods may comprise non-templated sequences, particularly reflected in one or more overhang non-templated residues that were added by the polymerase or reverse transcriptase. The non-templated sequences of the DNA duplexes may be different from the tag sequences of the cDNA duplexes. For example, the non-templated sequences of the DNA duplex may be one or more hanging A's (e.g., A), and the non-templated sequences of the cDNA duplexes may be one or more hanging C's (e.g., C, CC, CCC, CCCC, CCCCC, or CCCCCC).

To the DNA duplexes and the cDNA duplexes from step 3 may be then added second adapters (FIG. 7, step 5), e.g., to the end opposite of the first appended adapters. In some cases, the second adapters added to the DNA duplexes may be different from the second adapters added to the cDNA duplexes. The second adapters to the DNA duplexes may comprise a sequence hybridizing to a sequence of the DNA duplexes (e.g., the tag sequences of the DNA duplexes). The second adapters to the cDNA duplexes may comprise a sequence hybridizing to a sequence of the cDNA duplexes (e.g., the tag sequences of the cDNA duplexes). For example, the second adapters to the DNA duplexes may be double-stranded DNA and comprise one or more hanging T's that hybridize to the one or more hanging A's of the tag sequence of the DNA duplexes. The sequence of such second adapters may then be used to identify originating DNA during the later sequencing analysis. Likewise, the second adapters to the cDNA duplexes may be double-stranded DNA and comprise one or more hanging G's (e.g., G, GG, GGG, GGGG, GGGGG, or GGGGGG) that hybridizes to the one or more hanging C's (e.g., C, CC, CCC, CCCC, CCCCC, or CCCCCC) of the tag sequence of the cDNA duplexes (or DNA/RNA hybrid nucleic acids). The sequence of such second adapters may be used to identify originating RNA during the sequencing analysis.

The double-stranded adapters may include additional functional sequences (e.g., one or more of amplification and sequencing primers, as well as attachment sequences). The added adapter sequences may then be used to prime amplification of the nucleic acid fragments (step 6).

The amplicons may then be sequenced. The sequence differences between the second adapters designed to be ligated to the DNA duplexes through hybridization to the one or more non-templated residues in the DNA duplexes and the second adapters designed to be ligated to the cDNA duplexes by hybridization to the one or more non-templated residues in the RNA/DNA duplexes may be used to distinguish the amplified products derived from the RNA and DNA in the original sample.

Alternatively, the additional dC residues appended by the SMARTer RT may be used to prime amplification with a primer that may include, in addition to optional sequencing primer and attachment sequences, an index or marker sequence that specifically identifies the cDNA product from RNA reverse transcription. With reference to FIG. 7 or 8, the template switch oligonucleotide, may be provided to include this additional tagging sequence along with the poly dG primer and optional additional sequencing primer (e.g., R1 and R2) and/or attachment sequences (e.g., p5 and p'7). Likewise, the additional dA residue or residues appended by the Bst 2.0 DNA polymerase may be used to prime amplification with a primer that may include, in addition to optional sequencing primer and attachment sequences, an index or marker sequence that specifically identifies the DNA product from the DNA polymerase extension reaction. With reference to FIG. 7 or 8, the template switch oligonucleotide, may be provided to include this additional tagging sequence along with the poly dT primer and optional additional sequencing primer (e.g., R1 and R2) and/or attachment sequences (e.g., P5 and P7).

D. Label Element

The present disclosure also provides for the adapter with one or more labels. Labels can be added to an adapter when purification is desired or for using particular detection.

In some embodiments, purification can be achieved be using oligonucleotides conjugated to a label such as a biotin tag and using, for example, avidin or streptavidin attached to a solid support for purification or buffer exchange.

Examples of labels that can be used with the disclosure include but are not limited to any of those known in the art, such as enzymes, fluorophores, radioisotopes, stable free radicals, lummescers, such as chemilummescers, biolummescers and the like, dyes, pigments, enzyme substrates and other labels. One skilled in the art will choose a label that is compatible with the chosen detection method.

E. Ligation & Ligase Enzymes

In some cases, a first or second adapter may be appended to nucleic acids in a sample using a single ligase enzyme or multiple different ligases. In some cases, the single ligase enzyme has the ability to ligate an adapter to both DNA and RNA target molecules. As used herein, the term "pan-ligase" is used to refer to a single ligase with the ability to ligate an adapter to both DNA and RNA targets. When multiple different ligases are used (e.g., a dual ligase system), the ligases may each be specific for a target (e.g., DNA-specific or RNA-specific). In some cases, a dual ligase system may include DNA-specific, RNA-specific, and/or pan-ligases, in any combination. In some cases, the ligase is specific for double-stranded nucleic acids (e.g., dsDNA, dsRNA, RNA/DNA duplex). An example of a ligase specific for double-stranded DNA and DNA/RNA hybrids is T4 DNA ligase. In some cases, the ligase is specific for single-stranded nucleic acids (e.g., ssDNA, ssRNA). An example of such ligase is CircLigase II. In some cases, the ligase is specific for RNA/DNA duplexes. In some cases, the ligase is able to work on single-stranded, double-stranded, and/or RNA/DNA nucleic acids in any combination.

Both DNA or/and RNA ligases that may be used with the disclosure. Examples of ligases that can be used with the disclosure include but are not limited to, T4 DNA Ligase, T3 DNA Ligase, T7 DNA Ligase, *E. coli* DNA Ligase, HiFi Taq DNA Ligase, 9° N™ DNA Ligase, Taq DNA Ligase, SplintR® Ligase (also known as. PBCV-1 DNA Ligase or *Chlorella* virus DNA Ligase), Thermostable 5' AppDNA/RNA Ligase, T4 RNA Ligase, T4 RNA Ligase 2, T4 RNA Ligase 2 Truncated, T4 RNA Ligase 2 Truncated K227Q, T4 RNA Ligase 2, Truncated KQ, RtcB Ligase (joins single stranded RNA with a 3"-phosphate or 2',3'-cyclic phosphate to another RNA), CircLigase II, CircLigase ssDNA Ligase, CircLigase RNA Ligase, aor Ampligase® Thermostable DNA Ligase or a combination thereof.

The reaction mixture may include a dual ligase system that uses each of a DNA ligase and an RNA ligase for carrying out the first ligation step (FIG. 1, 120), to append the first adapter to the nucleic acids in the sample, whether they are DNA or RNA. The DNA ligase in the dual-ligase system may preferentially work on DNA over RNA, even in samples that contain both RNA and DNA in the same container or tube. Similarly, the RNA ligase may preferentially work on RNA over DNA, even in samples that contain RNA and DNA in the same container or tube. In some cases, the ligase added at the first ligation step has pan-ligation capabilities and is able to ligate the adapter to both the RNA and the DNA strands in the sample (e.g., CircLigase II). In some cases, a pan-ligase is used in combination with a RNA-specific ligase, a DNA-specific ligase, or with a second ligase that is also capable of ligating to both RNA and DNA. In cases where more than one ligase is used, the ligases can be added simultaneously to the sample. In other cases, the ligases are added sequentially. In some cases, a single or a dual ligase system may be employed in order to carry out the second adapter ligation step (FIG. 1, 140). In certain embodiments, T4 DNA ligase is used to ligate the second adapter to the duplex. The enzymes and reaction conditions may be selected to provide sufficient levels of ligation activity of the first and second adapters to both the DNA and RNA fragments in the sample.

As noted above, a single ligase enzyme may be selected for the reaction system that has sufficient ligation activity for each of DNA and RNA substrates. In such cases, a ligase may generally be selected that does not show any overwhelming preference for either of DNA or RNA substrates. Ligases applicable to this system may include, for example, CircLigase II, T4 RNA ligase 1 and 2, including truncated forms, T4 DNA ligase, and Thermostable App-DNA/RNA ligases. Of these ligases, CircLigase II may provide less discrimination between DNA or RNA substrates, and thus provides an example of a ligase for the first ligation reaction (e.g., FIG. 1, 120). A ligase that can ligate dsDNA and/or DNA-RNA hybrids (e.g., T4 DNA ligase) can be used for the second ligation reaction (e.g., FIG. 1, 140).

Ligases that may be used in the methods provided herein may include, but are not limited to, T4 DNA Ligase, T3 DNA Ligase, T7 DNA Ligase, *E. coli* DNA Ligase, HiFi Taq DNA Ligase, 9° N™ DNA Ligase, Taq DNA Ligase, SplintR® Ligase, Thermostable 5' AppDNA/RNA Ligase, T4 RNA Ligase, T4 RNA Ligase 2, T4 RNA Ligase 2 Truncated, T4 RNA Ligase 2 Truncated K227Q, T4 RNA Ligase 2, Truncated KQ, RtcB Ligase, CircLigase II, CircLigase ssDNA Ligase, CircLigase RNA Ligase, Ampligase® Thermostable DNA Ligase, or a combination thereof.

In some cases, the adapters ligated to single-stranded RNA may contain a 5'-end modification such as App (e.g., pre-adenylation). The presence of the 5' App modification can enable oligonucleotides to act as direct substrates for certain ligases and remove the need for ATP. Adapters to single-stranded RNA can contain a 5' adenylation (5' App) modification and/or an RNA-identifying code.

Alternatively or additionally, DNA and RNA in a sample can be specifically marked during the first adapter ligation step and/or during the second ligation step. In some cases, a ligase specific for one type of the nucleic acids is used. For example, a DNA-specific ligase may be used so that adapters are only ligated to the DNA molecules in the sample. In another example, an RNA-specific ligase may be used so that adapters are only ligated to the RNA molecules in the sample. In certain cases, successive ligation with a first ligase specific to one type of nucleic acid and a second ligase not discriminating nucleic acids types are used. For example, successive ligation first with a DNA-specific ligase (e.g., CircLigase ssDNA ligase) followed by a ligase that can act on a DNA or RNA template (e.g., CircLigase II) may be used. Sequential or concurrent first adapter ligation and/or sequential or concurrent second adapter ligation may provide the ability to distinguish between chemical forms of nucleic acids (e.g., DNA and RNA). The choice of ligation method may depend on the ligase specificities and reaction conditions for each ligase used.

F. Successive Mode of Attachment

The methods provided by the present disclosure can be applied in a successive mode, that is more than one enzymatic steps can be applied at separate steps in the process. In some cases when successive ligation is used, a wash step can be performed between the two ligation reactions to remove the first ligase and excess adapters. For example, successive ligation can be used in the first adapter ligation step (e.g., FIG. 1, 120). Biotinylated first adapters with a code for DNA (1a adapters) can be added to the sample nucleic acids and ligated to ssDNA using a DNA ligase. Ligation produces can be immobilized on streptavidin beads. Excess 1a adapters can be washed off. First adapters with a code for RNA (1b adapters) can be added and ligated to ssRNA using an RNA ligase.

In general, for each ligation step (e.g., first ligation, second ligation, pre-denaturation ligation), a single general adapter or specific adapters can be used. In some cases, a single adapter is added to all nucleic acids in a ligation step. In some cases, a single adapter is added to a specific group of nucleic acids (e.g., only single-stranded or only double-stranded for a pre-denaturation ligation) in a ligation step. In some cases, different adapters can be added to specific groups of nucleic acids (e.g., ssDNA, ssRNA, dsDNA, or dsRNA) in a ligation step. In some cases, selectivity can be achieved through enzymatic selectivity with a wash step in between sequential enzymatic steps to remove excess unligated adapters. In some cases, selectivity can be achieved through sequence-specific hybridization to different overhangs added by polymerases in the primer extension step.

G. Primer Extension

Adapter Attachment Without Using a Ligase

The first and/or second adapters may be added to the nucleic acids in the sample with an approach not requiring a ligase-catalyzed reaction. In some cases, the adapters may be added by a primer extension reaction. Such reaction may be performed using random priming with partially hybridized oligonucleotides. The oligonucleotide may comprise a priming sequence that hybridizes to the nucleic acids in the sample and an adapter sequence (e.g., a single stranded adapter sequence or a double-stranded adapter sequence). In some cases, the oligonucleotides used for random priming contain random sequences. The random sequences can be optimized to hybridize to a particular genome, such as a human genome or a pathogen genome. For example, in order to promote priming of pathogen genomes, the collection of random oligonucleotides (e.g., 13mers) may be partially or entirely depleted of known human sequences.

In some cases, the second adapter may be introduced during the amplification stage (e.g., the first PCR cycle, FIG. 1, 150) without use of a ligase enzyme. For example, the second adapter itself may behave as a primer that recognizes one or more non-templated nucleic acids residues added to the end of a nascent strand by a polymerase such as SMARTer RT or Bst 2.0. Such adapter may comprise a domain that hybridizes to the one or more non-templated nucleic acid residues such as one or more C's (e.g., C, CC, CCC, CCCC, CCCCC, or CCCCCC) or one or more A's (e.g., A) added by the polymerase. Thus, the second adapter may comprise one or more G residues in order to hybridize to the one or more C residues deposited by SMARTer RT. Similarly, the second adapters may include, or may also include, one or more T residues to recognize the one or more A residues added by Bst 2.0 DNA polymerase. The adapter may be used to prime replication during amplification 150, resulting in incorporation of the adapter sequence into the resulting amplified DNA molecules. In some cases, the second adapters contain one or more identifying sequences to indicate that the original nucleic acid is DNA or RNA. For example, an adapter with one or more T overhang residues may also contain a sequence that "marks" the nucleic acid as originating from DNA. An adapter with one or more G overhang residues may also contain a sequence that "marks" the nucleic acid as originating from RNA. Such adapters may also be used in ligation reactions described above.

In the first replication or primer extension step (e.g., FIG. 1, 130), the enzymes used in a single reaction mixture may be able to perform the primer extension reaction against both of a DNA or RNA template with a sufficient level of replication of each. Generally, the primer extension portion of the reaction involves the addition of one or more primers (FIG. 1, 170) that recognize (e.g., hybridize to) the first adapters attached to the single-stranded DNA and/or RNA. Primer extension also involves use of a polymerase (e.g., RT, DNA polymerase), dNTPs, and appropriate buffer conditions for the reactions. Following annealing of the primer, the polymerases extend the nucleic acid sequence along the length of the template, thereby forming a nascent nucleic acid (e.g., DNA) strand. In some cases, the polymerization ends when the end of the template is reached. In other cases, one or more of the polymerases adds one or more non-templated nucleic acids to the end of the nascent strand, as described further herein. Such non-templated nucleic acids are at times referred to as "overhangs", "hanging" nucleotides, or "tails" herein.

Preferably, the primer used in the primer extension reaction is DNA, but in some cases, the primer contains RNA or both RNA and DNA. In some cases, the primer may contain additional sequences in addition to the domain that is complementary to the adapter sequence. In some cases, the primer may contain one or more base and/or ribose ring modifications.

In some cases, the polymerase may be able to polymerize both DNA and RNA templates. Such polymerase may be used singly or in combination with a DNA-specific polymerase and/or a RNA-specific polymerase. In some cases, a polymerase specific for RNA (e.g., reverse transcriptase) is used in combination with a DNA-specific polymerase. In certain embodiments, polymerases capable of adding one or more non-templated nucleic acid residues to the end of a nascent strand of the duplex may be used, as described in more detail in FIGS. 7 and 8. Such polymerases may be used to mark nucleic acids as originating from RNA or DNA in the sample and/or from single- or double-stranded nucleic acids in the sample, as described further herein.

In some cases, the hybridizing portion of the primer can be 1, 2, 3, 4, 5, 6, 7, 8, 9, 10, 11, 12, 13, 14, 15, 16, 17, 18, 19, 20, 25, 26, 27, 28, 29, 30, 31, 32, 33, 34, 35, 36, 37, 38, 39, 40, 41, 42, 43, 44, 45, or 50 base pairs in length. In some cases, the primer is attached to a multifunctional adapter.

The multifunctional adapter can be single-stranded, double-stranded or both such that the ends are protected during the reaction.

The enzymes used may include multiple enzymes with different specificities or selectivities for DNA or RNA templates in order to achieve sufficient levels of replication of both forms of nucleic acids in the same reaction mixture, and preferably under the same reaction conditions. By way of example, the reaction mixture may include both DNA polymerases, as well as reverse transcriptases, in order to replicate using either DNA or RNA as a template with a similar level of efficiency/replication.

Non-limiting examples of DNA polymerases that can be used in the primer extension step are Bst DNA Polymerase, Full Length, Bst DNA Polymerase, Large Fragment, Bsu DNA Polymerase, Crimson Taq DNA Polymerase, Large Fragment, Deep VentR™ (NEB) DNA Polymerase, Deep VentR™ (exo-) (NEB) DNA Polymerase, E. coli DNA Polymerase I, Klenow Fragment (3'→5' exo-), DNA Polymerase I, Large (Klenow) Fragment, LongAmp® Taq DNA Polymerase or Hot Start (NEB), M-MuLV Reverse Transcriptase, OneTaq® DNA Polymerase or Hot Start (NEB), phi29 DNA Polymerase, Phusion® Hot Start Flex DNA Polymerase (NEB), Phusion® High-Fidelity DNA Polymerase (NEB), Q5®+Q5® Hot Start DNA Polymerase (NEB), Sulfolobus DNA Polymerase IV, T4 DNA Polymerase, T7 DNA Polymerase (unmodified), Taq DNA Polymerase, or Therminator™ DNA Polymerase (NEB), VentR® DNA Polymerase (NEB), or VentR® (exo-) DNA Polymerase (NEB), or a combination thereof.

Non-limiting examples of RT polymerases that can be used in the primer extension step are WarmStart RTx Reverse Transcriptase(NEB), AMV Reverse Transcriptase (NEB), Superscript IV RT (Invitrogen), M-MLV Rnase H(-) (Promega), SMARTer reverse transcriptase (Clontech), and RevertAid RnaseH(-) RT (Thermo Scientific), or ProtoScript® II Reverse Transcriptase (NEB), or a combination thereof.

In some applications the primer extension reaction can use a polymerase having strand displacing activity. Examples of displacing polymerase that can be used with the disclosure include but are not limited to, Klenow polymerase, exo-Klenow polymerase, 5'-3' exo-Klenow polymerase, Bst polymerase, Bst large fragment polymerase, Vent polymerase, Vent polymerase, Deep Vent (exo-) polymerase, 9° Nm polymerase, Therminator polymerase, Therminator II polymerase, MMulV Reverse Transcriptase, phi29 polymerase, or DyNAzyme EXT polymerase, or a combination thereof.

In some cases, a method described herein can comprise successive addition of a DNA polymerase followed by a reverse transcriptase or concurrent addition of a DNA polymerase and a reverse transcriptase. In some cases, the same primer can be used, or different primers can be used to mark RNA vs. DNA origins. For example, if different primers are used, a first primer that recognizes the adapter ligated in the first ligation and that also contains a DNA code can be added. A DNA polymerase can be used to extend the first primer to form dsDNA. A wash step can remove excess first primer. In some cases, a denaturation step is added prior to the wash step to selectively denature unextended primers that are hybridized to the adapter but to not denature primer extension products (e.g., full length dsDNA). A second primer that recognizes the adapter and that contains an RNA code can then be added. A reverse transcriptase can be added to conduct reverse transcription.

Figure 11B:
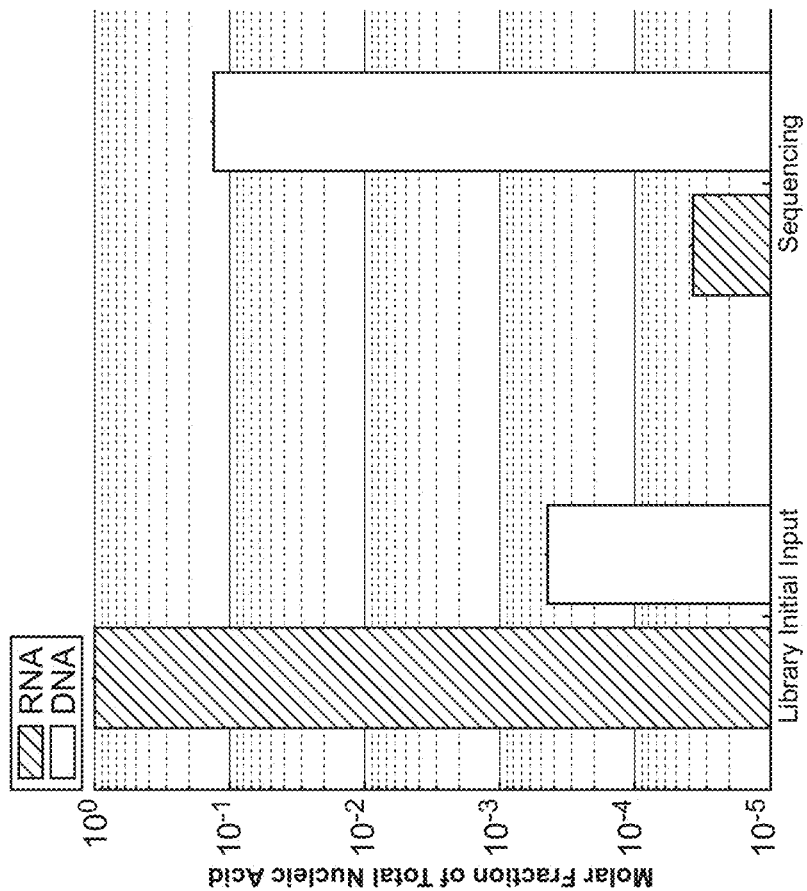
FIG. 11A and FIG. 11B show bar graphs comparing the recovery of the input DNA and RNA of the starting sample with the final output DNA and RNA detected after conducting the methods of the disclosure. 11A shows recovery of DNA and RNA product with a SMARTer Reverse Transcriptase. 11B shows recovery of the DNA and RNA product with a Bst 2.0 Polymerase.
Figure 11A:
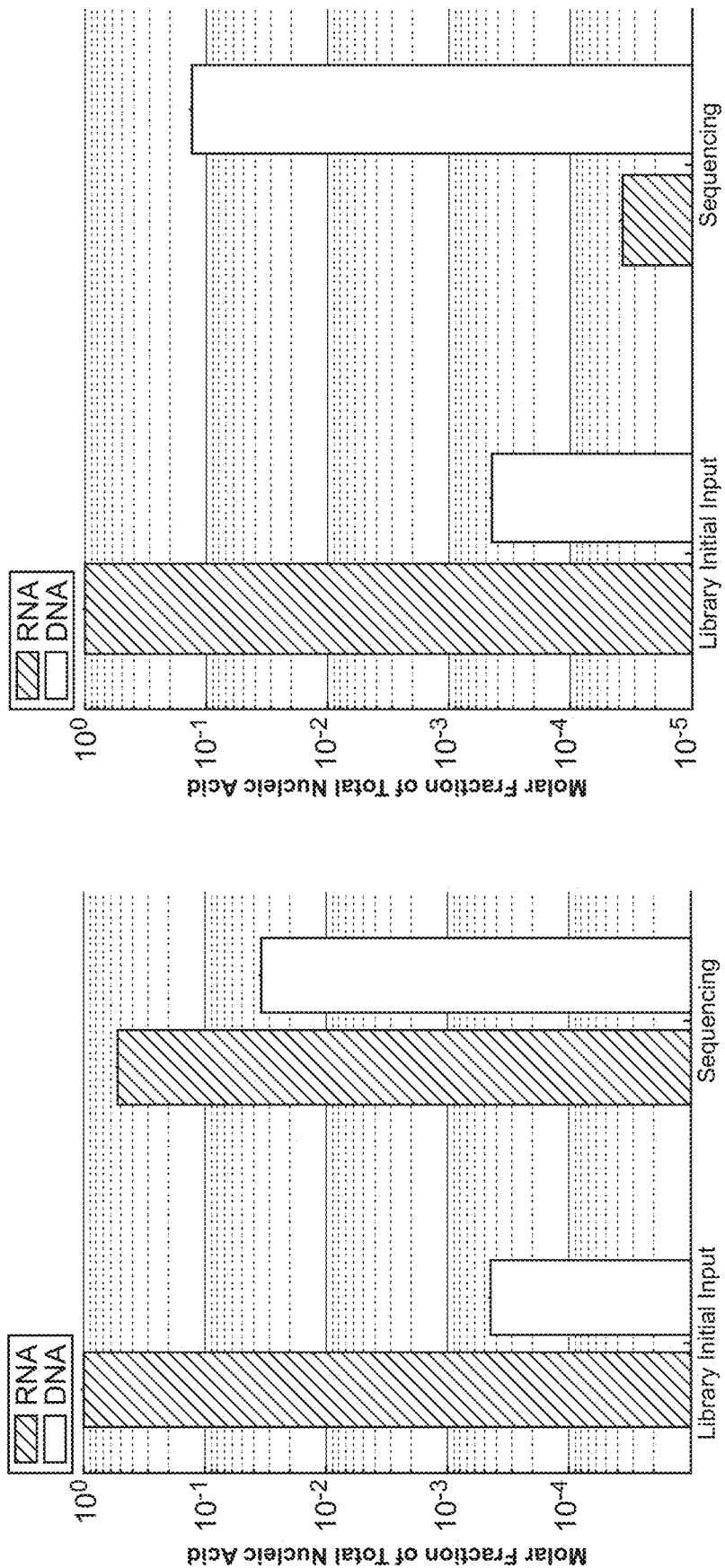

Alternatively, a single enzyme system may be employed that has sufficient activity to both template types (e.g., with both DNA-dependent DNA polymerase activity and RNA-dependent DNA polymerase activity) in the single reaction mixture, and preferably under the same reaction conditions. In particular, certain reverse transcriptase enzymes show lower levels of discrimination between DNA or RNA templates in replication. For example, as shown in FIGS. 11A and 11B, SMARTer reverse transcriptase polymerases (Clontech) demonstrate the ability to carry out primer extension/replication against both DNA and RNA templates without an excessive preference for single-stranded DNA templates (set of 52 bp DNA oligonucleotides) as compared to single-stranded RNA templates (50 nt RNA oligonucleotides). As such, in certain cases, the replication step is carried out by incorporating the SMARTer reverse transcriptase in the single reaction mixture to carry out replication/primer extension against both DNA and RNA sample fragment templates in the reaction mixture.

VI. Amplification

The methods of the disclosure can comprise an amplification step using a polymerase chain reaction (PCR). In some applications, there is enough starting material in the sample such that no amplification step is necessarily required.

In some applications, the amplification step of the method performs a forward transcription amplification reaction. In some applications, the amplification step of the method, performs a reverse transcription amplification reaction. In some applications the polymerase acts on a single-stranded nucleic acid molecule. In some applications the polymerase acts on double-stranded nucleic acid molecule.

In most of the methods that include an amplification step, the amplification step generally serves to amplify the double-stranded DNA resulting from the primer extension reaction. Such dsDNA may contain a first or second adapter, as described herein. When first and second adapters are appended to the dsDNA, the amplification may be conducted using a polymerase chain reaction (PCR) using forward and reverse primers that, together, recognize the first and second adapter. The PCR reaction maybe conducted with a DNA polymerase. In some cases, the DNA polymerase is identical to the DNA polymerase used during the primer extension step (e.g., Bst 2.0 DNA polymerase). In some cases, DNA polymerase is different from the DNA polymerase used in the primer extension step. Any DNA polymerase known in the art may be used for amplification.

VII. Methods

The methods provided by the disclosure allow for the concurrent detection of different nucleic acid forms in a sample without the requirement of physical separation or parallel processing. The methods can be used to distinguishing between DNA and RNA molecules or between single-stranded nucleic acids and double-stranded nucleic acids or a combination thereof. In some embodiments, a method can provide for the concurrent analysis of 2, 3, 4, 5, 6, 7, 8, 9, 10 or more different nucleic acid forms in a sample A. Ligation Methods The present disclosure provides ligation methods for the concurrent detection of different nucleic acid forms within a sample. In some applications, the method can comprise denaturation, ligation of a first adapter, primer extension, ligation of a second adapter, and amplification, FIG. 1. In some cases, the ligation method can be conducted concurrently with two different ligation reactions in the same reaction, each with a preference for a different nucleic acid form within a sample (e.g., DNA, RNA, dsDNA, dsRNA, ssDNA, ssRNA, etc.). However, in some applications the ligation method can be conducted using two different ligation reactions in successive steps.

In some cases, a ligation method provided herein may involve the use of one or more ligases that preferentially recognize a particular nucleic acid form (e.g., RNA, DNA, ds nucleic acids, ss nucleic acids, etc.). In some cases, a ligase that is specific for a certain nucleic acid form (e.g, RNA) may be used with an adapter that is configured to be preferentially recognized by that ligase. The adapter may contain a known sequence. For example, a ligase may preferentially ligate the adapter to RNA, thereby "marking" the RNA as RNA. In another example, a ligase may preferentially ligate a different adapter with a different identifying sequence to DNA, thereby "marking" the DNA as DNA.

Use of ligases that preferentially ligate to a certain form of nucleic acids can generally be used in any of the methods provided herein, particularly during any ligation step. In some cases, two ligases with different nucleic acid preferences are used during the ligation step. In some cases, one ligaste is used, or more than two ligases. In some cases, the ligases are used in addition to the polymerases with non-template activity described herein in order to provide additional, or confirmatory information about the identify of a nucleic acid form.

B. Primer-Extension Method

The present disclosure provides primer-extension methods for the concurrent detection or successive detection of different nucleic acid forms within a sample. In some applications, the method can comprise denaturing the nucleic acids to be analyzed (e.g., dsDNA, dsRNA, ssDNA, and/or ssRNA), primer extension to add a first adapter, primer extension to add a second adapter, and/or amplification of the resulting product with a primer that recognizes the first and/or second adapter. In general, the primer extension reaction can be carried out with a polymerase and a primer. In some applications, the polymerase can be a DNA-dependent polymerase. In some applications, the polymerase can be a RNA-dependent polymerase.

Figure 2:
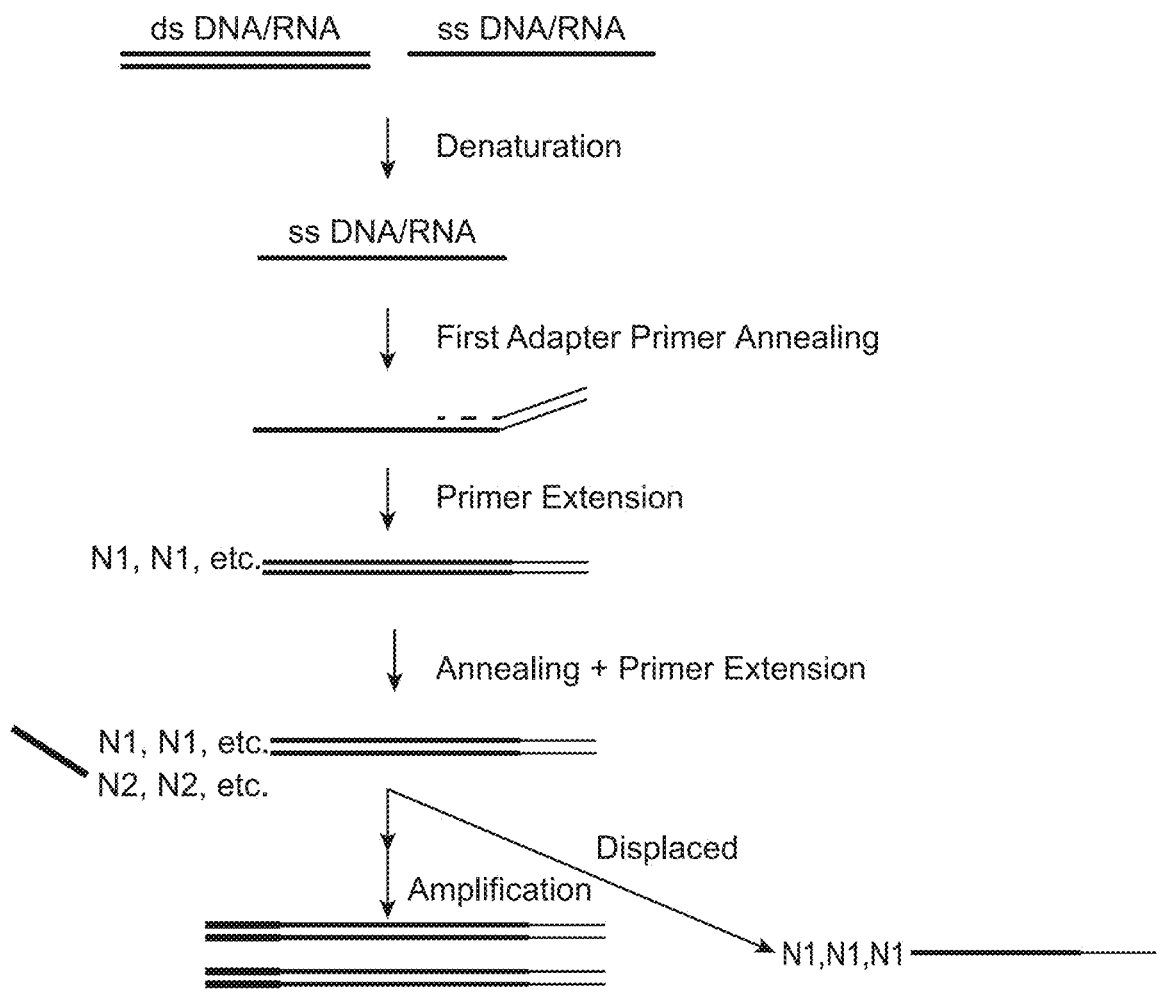
FIG. 2 depicts exemplary techniques to detect various nucleic acid forms in a sample using polymerases with non-template activity.

In some applications, a primer extension method can be conducted using a polymerase that has non-template activity, FIG. 2. In some cases, the polymerase has a preference for a certain form of template (e.g., preference for a DNA template over an RNA template, or preference for an RNA template over a DNA template). In some cases, a primer complementary to the non-templated bases can be used. Such a primer can be used, for example, to add a second adapter to a developing sequence. In some applications, the primer extension can be carried out using a polymerase with strand displacement activity.

C. Ligation-Primer Extension Method

The present disclosure provides a ligation-primer extension method. The primer extension method can be particularly useful in applications where targeting is desired.

Figure 3:
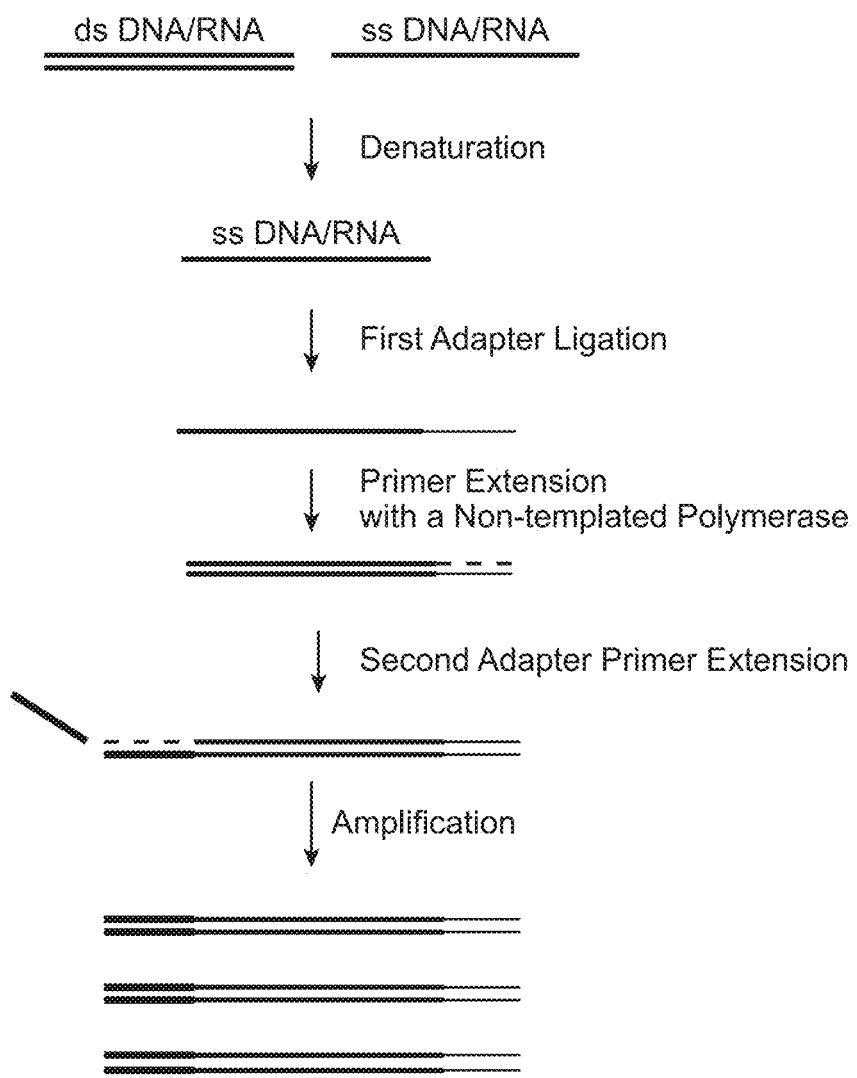
FIG. 3 depicts ligation/primer extension approaches using polymerases having non-templated activity to detect various nucleic acid forms in a sample.

In some embodiments, a ligation-primer extension method can comprise a ligation method using a polymerase having non-templated activity to detect various nucleic acid forms in a sample. Such a method can comprise: attaching a first adapter by ligation, carrying out a primer extension with a polymerase that has non-templated activity to make an overhang, attaching a second adapter by primer extension, and amplification, FIG. 3. In some embodiments, the second adapter primer extension is performed using an adapter (or primer) that comprises both a sequence of a second adapter and a sequence (e.g., N2N2, as described herein) that is the reverse complement of the sequence in the overhang.

Figure 4:
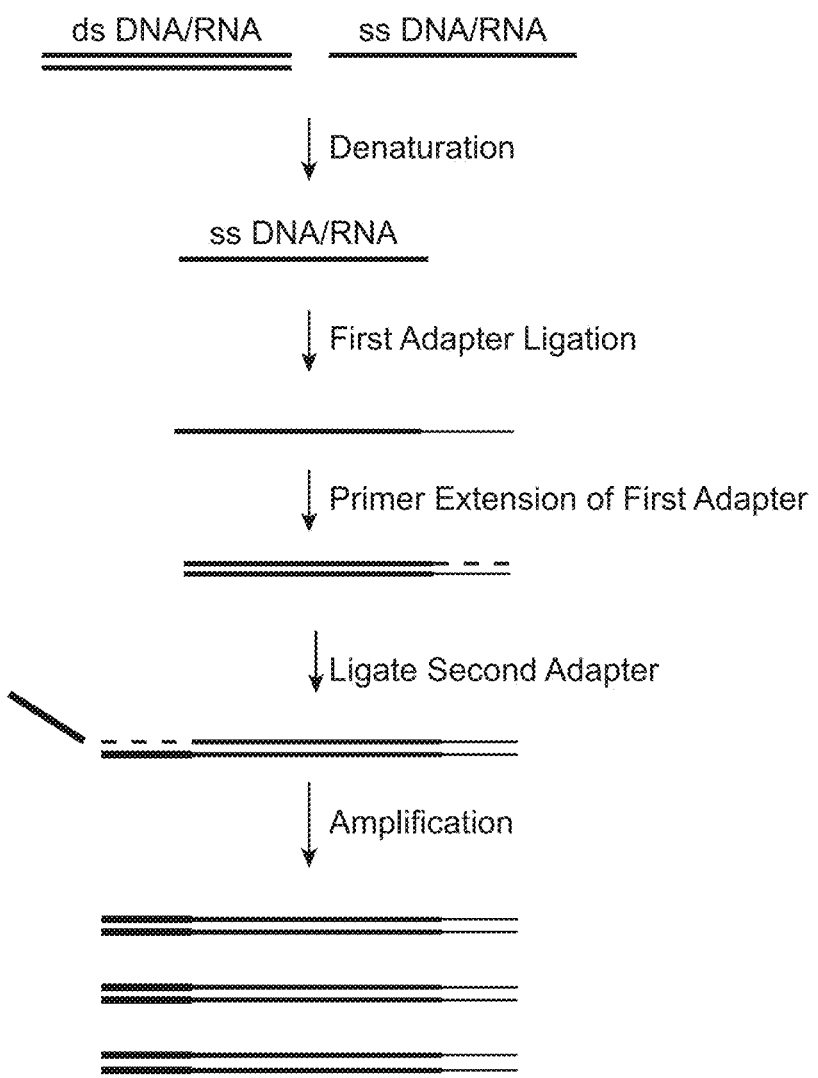
FIG. 4 depicts exemplary approaches to detect various nucleic acid forms in a sample, including approaches using a second adapter that contains both double-stranded and single-stranded regions.

In some embodiments, a ligation-primer extension method can comprise a ligation method using an adapter having both dsDNA and ssDNA regions in order to detect various nucleic acid forms in a sample. As shown in FIG. 4, in some cases, the adapter may have a double-stranded region that can be ligated to the double-stranded product of a primer extension reaction (e.g., a primer extension reaction that contains the sequence of the first adapter). Such adapter may also contain a sequence of a second adapter, as indicated by the bolded diagonal line in FIG. 4. Such a method can comprise the following steps: attaching a first adapter by ligation, performing a primer extension reaction of the first adapter followed by amplification with primers, ligating a second adapter having both dsDNA and ssDNA regions, and PCR amplification, FIG. 4. As in many of the other methods and approaches described herein, the first adapter may be attached to the nucleic acids by any method, including by a primer extention reaction using a random primer that recognizes DNA and/or RNA attached to the first adapter or by ligating the first adapter to a single-stranded nucleic acid, and using a primer that recognizes the first adapter to extend the strand.

D. Non-Templated Methods

The present disclosure provides methods involving the use of polymerases capable of adding non-templated nucleotides to a nucleic acid strand. In general, a non-templated method provided herein can use one or more polymerases having non-templated activity. In some cases, the method may involve the use of two polymerases, each with a preference for a different template and each that appends a different set of non-templated nucleotides to the end of the developing strand. The non-templated nucleotides can then be used, downstream, to identify the original form of the nucleic acids. For example, two polymerases, one with a preference for a DNA template, one with a preference for an RNA template, can be used, wherein each polymerase appends a different set of non-templated nucleotides to the developing strand, thereby "marking" each strand as originating from DNA or RNA. The polymerases may each have a preference for any type of nucleic acid form (e.g., DNA, RNA, ssDNA, ssRNA, dsDNA, or dsRNA). In some cases, three or more polymerases are used, each with a preference for a different nucleic acid form.

Figure 5:
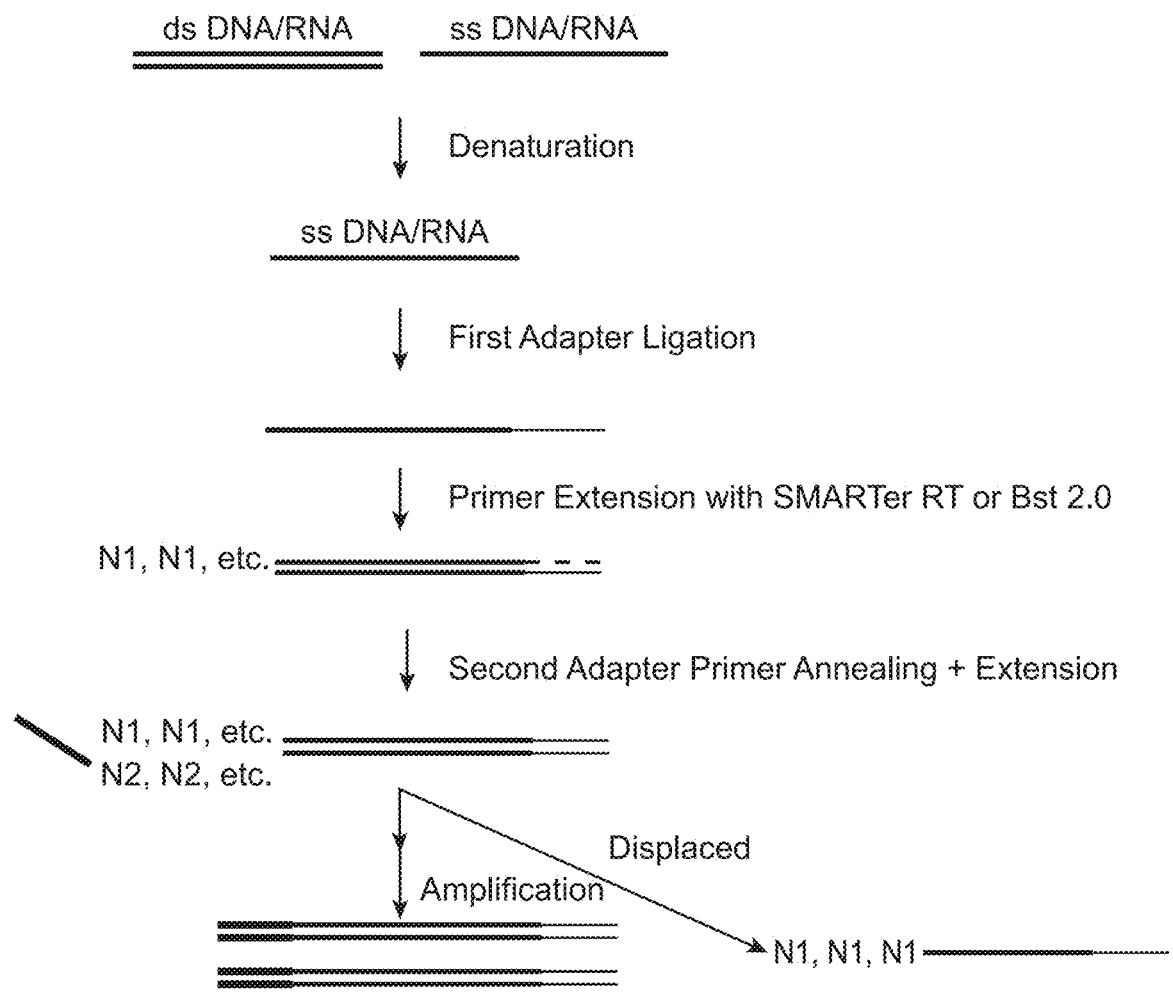
FIG. 5 depicts exemplary non-templated approaches to detect various nucleic acid forms in a sample, including an approach using a strand-displacing polymerase.

In applications where the detection of the different nucleic acids forms in a sample is desired, two polymerases having non-templated activity, should have a different preference in nucleic acid bases for the formation of an overhang, FIGS. 2 and 5. For example, one polymerase with a preference of a form of nucleic acid (e.g., DNA) can have non-templated activity for making a "A" overhang, while a second polymerase with a preference for a different form of nucleic acid (e.g., RNA) can have non-templated activity for making a "C" overhang.

In some embodiments, a method using a polymerase with non-template activity can be used to distinguish RNA and DNA forms in a sample comprising dsDNA, ssDNA, dsRNA, ssRNA, in any combination. In some cases, the method may comprise denaturing the nucleic acids in a sample to produce a sample that contains single-stranded nucleic acids and adding a first adapter to the single-stranded nucleic acids using a primer extension reaction, where the extension primer contains both the first adapter and a 3'-end randomized region that binds to denatured DNA and RNA molecules in the sample. In some cases, the extension primer also contains a 5'-end region that carries one or more functionalities of a first adapter primer as shown in FIG. 1, or as otherwise described herein. The non-randomized region of the extension primer can be protected by hybridizing its reverse complement. Once the extension primer is hybridized, the primer extension reaction is carried out by a polymerase that can utilize DNA and RNA templates with a known nucleic acid preference for its non-templated activity, such that it introduces an overhang sequence at the 3'-end of the newly synthesized strand is (e.g., "N1,N1" of FIG. 2).

Next, an annealing and amplification step can be carried. The amplification may be carried out using two amplification primers. The first of these amplification primers may comprise: (1) a primer that is reverse complementary to the known overhang N1 N1 sequence located at the 3'-end (here, "N2N2") and (2) a second adapter element positioned at its 5'-end. Generally, the N2N2 primer is attached to the 3' end of the second adapter element in these embodiments. The second of these amplification primers may recognize the first adapter (that was initially added during the first adapter primer extension). This amplification step is carried out such that strands that contain both first adapter and second adapter elements may get amplified.

In some cases, the amplification involves use of a polymerase with strand-displacing activity. As shown in FIG. 2, use of the strand displacing polymerase may result in the N1N1N1 . . . strand being displaced with the final product containing the N2N2 . . . sequence and the sequence of the first adapter. Any strands lacking either a first adapter or a second adapter elements or both elements will not get amplified (e.g. the original sample DNA and RNA strands) or will get amplified only linearly (e.g. the First Adapter Primer Extension), FIG. 2.

In some embodiments, a method using a polymerase with non-template activity can comprise: a denaturation step involving denaturing nucleic acids in a sample, a first adapter primer extension step: where the first adapter is introduced by primer extension, where the extension primer contains a 3'-end randomized region that binds to denatured DNA and RNA molecules. The extension primer may also contain a 5'-end region that carries all the functionalities of a first adapter primer as shown in FIG. 1. The non-randomized region of the extension primer can be protected by hybridizing its reverse complement. Once the extension primer is hybridized, the primer extension reaction can, in some cases, be carried out by a SMARTer RT or Bst 2.0 DNA polymerase with a known nucleic acid preference for its non-templated activity (FIG. 5), such that the introduced overhang sequence at the 3'-end of the newly synthesized strand is known (e.g., for example C,C,C and A,A,A, respectively). Next, an annealing and amplification step can be carried: this step can be carried out using two amplification primers one that has a primer reverse complementary to the known overhang N1, N1, sequence located at its 3'-end with second adapter elements at its 5'-end; (2) a primer containing the same or 5'-end of the first adapter. Next, amplification step is carried out such that strands that contain both first adapter and second adapter elements will get amplified. Finally, a strand displacement step can be carried out using a polymerase with strand-displacing activity: Any strands lacking either a first adapter or a second adapter elements or both elements will not get amplified (e.g. the original sample DNA and RNA strands) or will get amplified only linearly (e.g. the First Adapter Primer Extension), FIG. 2

In general, non-templated activity is the ability of an enzyme (e.g., DNA polymerases, reverse transcriptases) to synthesize an overhang of additional nucleic acid bases in spite of the absence of a template to direct the addition of a particular nucleotide base, FIG. 17. In general, this can occur at the ends of the template, such as the 3' or 5' ends of a nucleic acid.

Example DNA polymerases having non-templated activity include but are not limited to, A- and B-family DNA polymerases, such as (KOD XL, KOD (exo-), Bst 2.0, Therminator, Deep Vent (exo-) Pfu DNA polymerase, or Taq.

Examples of reverse transcriptases having non-templated activity include but are not limited to, HIV reverse transcriptase, Moloney murine leukemia virus (e.g., SuperScript II™ (ThermoFisher), or SuperScript III™ (ThermoFisher).

Figure 18:
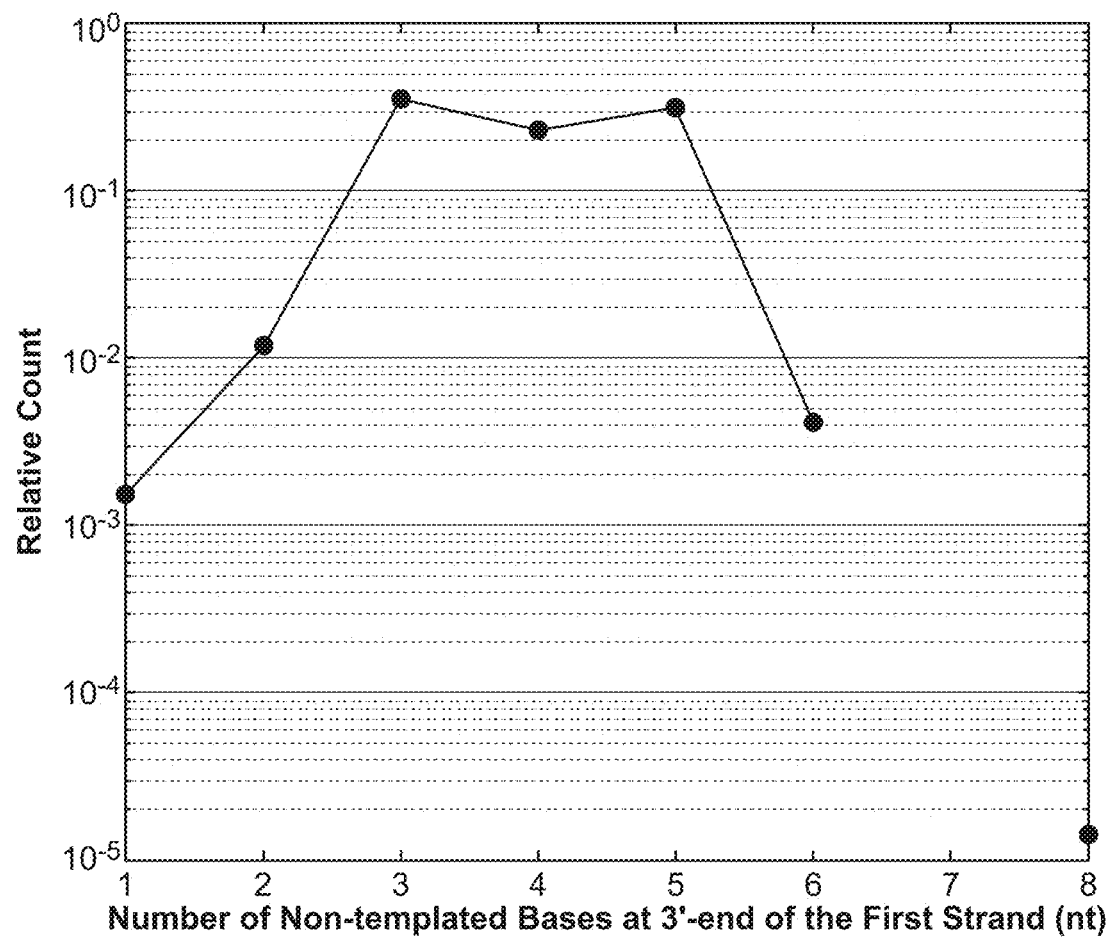
FIG. 18 depicts the non-template activity of a polymerase. The y-axis shows the number of reads detected and the x-axis shows the number of non-templated bases added at the 3' end by the polymerase.

Non-template activity of an enzyme can be detected using amplification and sequencing to determine if an enzyme adds nucleotides at the end of the template that are non-templated (e.g., overhangs), FIG. 18. Using this method, one can determine if the polymerase has non-template activity. FIG. 18 shows one embodiment of a RNA polymerase (SMARTer RT) having non-templated activity which can add about one to six non-templated nucleotides at the '3 end to form an overhang.

In some applications, the non-templated method can comprise the following steps: denaturation of the sample nucleic acids, attaching a first adapter by ligation, performing a primer extension reaction using a primer that recognizes the first adapter using a polymerase that can generate non-template nucleotides at the ends (e.g. SMARTer RT, Bst 2.0 or the like), attaching the second adapter by primer extension, and amplification.

In some applications, the primer extension step can be carried out using a polymerase that has non-template activity. In this case an amplification primer would be complementary to the non-templated bases. In some applications, the primer extension can be carried out using a polymerase with strand-displacement activity. In some applications the polymerase is a DNA-dependent polymerase. In some applications the polymerase is a RNA-dependent polymerase.

In some embodiments, the non-templated method and be combined with a primer extension method, referred to as a non-templated-primer extension method. In some embodiments, a non-templated-primer extension method can be conducted using a successive mode in that the polymerases are used successively rather than at the same time, FIG. 7. In some embodiments, a non-templated-primer extension method can be using a concurrent mode, involving use of multiple polymerases in the same reaction mixture, FIG. 8.

E. Concurrent and Successive Modes

The enzymatic reaction steps of the methods (e.g., ligation, primer extension, and amplification) can be applied successively or concurrently. FIG. 7 shows some embodiments of a method using a successive mode. FIG. 8 shows some embodiments of a method using a concurrent mode.

Depending on the desired number of nucleic acids to be distinguished from one skilled in the art can using the appropriate number of identifying sequences (e.g., such as an index, barcode, non-templated nucleotide overhang, or random sequence).

For example (FIG. 9, step 1) end repair may be performed to generate blunt ends. One can use either the concurrent ligation mode or successive ligation mode to attach an identifying sequence (e.g., an index, a barcode, a random sequence, a non-templated sequence, or combination thereof) to the double-stranded nucleic acids in the sample (e.g. dsDNA, and dsRNA), FIG. 9, step 2. To identify dsDNA and dsRNA in the sample one can use a ligase with preference for double-stranded nucleic acids, such that the single-stranded nucleic acids in the sample are not ligated with an adapter, FIG. 9, step 2. After ligation of the adapter, the double-stranded nucleic acids are "marked" with the adapter. They then can be denatured into single-stranded nucleic acids, that will also contain the tag sequence of the adapter, as shown after step 2 in FIG. 9. In some embodiments, one can use a DNA Ligase and RNA Ligase 2 to attach two different adapters to dsDNA and dsRNA, respectively. Finally, one can proceed with a sample preparation process provided herein, FIG. 9, step 3, for example proceses as shown in FIG. 7 and FIG. 8.

The methods provided by the present disclosure can provide several advantages over approaches that use separate, parallel processing to analyze different nucleic acid forms in a sample. Depending on the application, the method may provide one or more advantages such as, decreasing the amount of starting sample required for an analysis, which in, turn can increase the ability to perform high throughput processes on various types of biological or clinical samples; decrease overall cost, improve the ability to compare the relative abundance or precise amount of nucleic acids, improve the ability to compare various structural forms and chemical structures. In some applications, the methods provided herein can have the advantage of providing more efficient recovery of short nucleic acid fragments. In some applications, the methods can have the advantage of decreasing the formation of adapter-dimer during the process.

As will be appreciated, at each of the first ligation step (step 2), first replication step (step 3), and second ligation step (step 4), enzymes and/or reaction conditions would typically be employed and optimized for the particular form of nucleic acid that is to be analyzed, e.g., DNA, RNA, or DNA/RNA hybrid. These enzymes and/or reaction conditions may not be optimized or even functional for (or may be substantially non-functional or lower functioning) toward the other forms of nucleic acids.

F. Distinguishing Structural Forms Method

Figure 9:
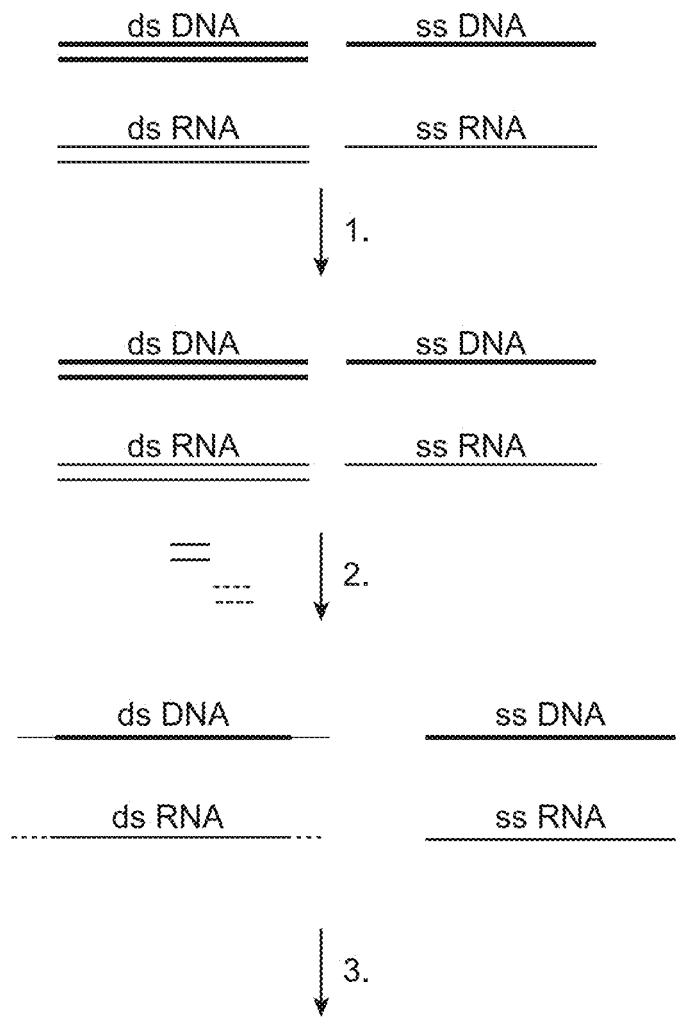
FIG. 9 exemplary approaches for distinguishing different structural forms of the nucleic acids in a sample.

The present disclosure provides a for distinguishing between different structural forms of nucleic acids. In some applications of the method, an additional adapter ligation step may be performed to help distinguish the structural forms of nucleic acids in a sample. An adapter may be selectively ligated prior to a denaturation step to only double-stranded (e.g., using a double-stranded nucleic acid ligase such as T4 DNA ligase and/or T4 RNA ligase 2) or only single-stranded nucleic acids (e.g., using a single-stranded nucleic acid ligase such as a CircLigase enzyme). In some cases, one or more adapters can be used, such as an adapter selective for double-stranded nucleic acids, an adapter selective for dsDNA, an adapter selective for dsRNA, an adapter selective for single-stranded nucleic acids, an adapter selective for ssDNA, or an adapter selective for ssRNA. For example, double-stranded adapters may be ligated to double-stranded DNA and/or double-stranded RNA in the sample before the denaturation step, as shown in FIG. 9. The sample may contain a mixture of dsDNA, dsRNA, ssDNA, ssRNA in any combination.

The sample may undergo an end-repair reaction of the nucleic acids (step 1). Concurrent or successive ligation by DNA ligase and RNA ligase 2 may be conducted in order to attach specific short double-stranded sequences (e.g. adapters) to the double-stranded nucleic acids in the sample, e.g., dsDNA and/or dsRNA (step 2). As a result, the double-stranded nucleic acids, but not the single-stranded nucleic acids in the sample contain the specific short double-stranded sequences (e.g. adapters). In some cases, an adapter sequence contains a code or index to indicate whether a nucleic acid derives from a double-stranded or single-stranded nucleic acid in the starting sample. The adapters to the double-stranded DNA may comprise different sequences than the adapters to the double-stranded RNA. Adapters to double-stranded RNA can contain an RNA-identifying code. A dsRNA ligase can be used to attach the adapters to dsRNA. Adapters to double-stranded DNA can be designed with a DNA-identifying code. The DNA adapter can be attached to dsDNA using a dsDNA ligase.

The adapters may be attached to the double-stranded nucleic acids by successive ligations using DNA ligase and RNA ligase 2, FIG. 9. Alternatively, the adapters may be attached to the double-stranded nucleic acids by concurrent ligation by a DNA ligase and an RNA ligase in the same reaction solution. The short sequences in step 2 can be deactivated to prevent concatemerization. For example, only one 3' end of these sequences may be left active for ligation, while both 5'-ends and the remaining 3'-end are deactivated by chemical means. Following the ligation of the specific short sequences, the sample may be denatured (step 3) such that it contains entirely single-stranded nucleic acids. The steps in FIG. 7 or FIG. 8 may then be conducted in order to process the RNA and DNA in the sample.

G. Splint Ligase Method

The present disclosure provides a splint ligase method. This process enables discrimination between RNA and DNA by ligating a DNA-specific sequence at the 5'-end of DNA using SplintR Ligase in combination with a splint adapter. In some embodiments, the method can be used to distinguish between the DNA and RNA in a sample. In some embodiments, the method can be used distinguish between the single-stranded and double-stranded molecules in a sample.

A splint adapter generally contains a double-stranded region and a single-stranded region, that may also be described as an overhang region. In some cases, the overhan region is at the 3' end of the double-stranded region. In some cases, the overhang region is at the 5' end of the double-stranded region. In some cases, the overhang is typically composed of degenerate sites (e.g., N, NN, NNN, NNNN, NNNNN, etc.), usually with a random sequence. The number of degenerate positions may vary. Generally, a population of splint adapters can be used, wherein the splint adapters have different random N sequences. The diversity of the sequences may enable hybridization with sample molecules with a starting unknown identity. In some cases, the NNNN region has a known sequence, and may be used to hybridize to, for example, a known nucleic acid, or to an adapter that has been attached to sample nucleic acid.

Figure 20:
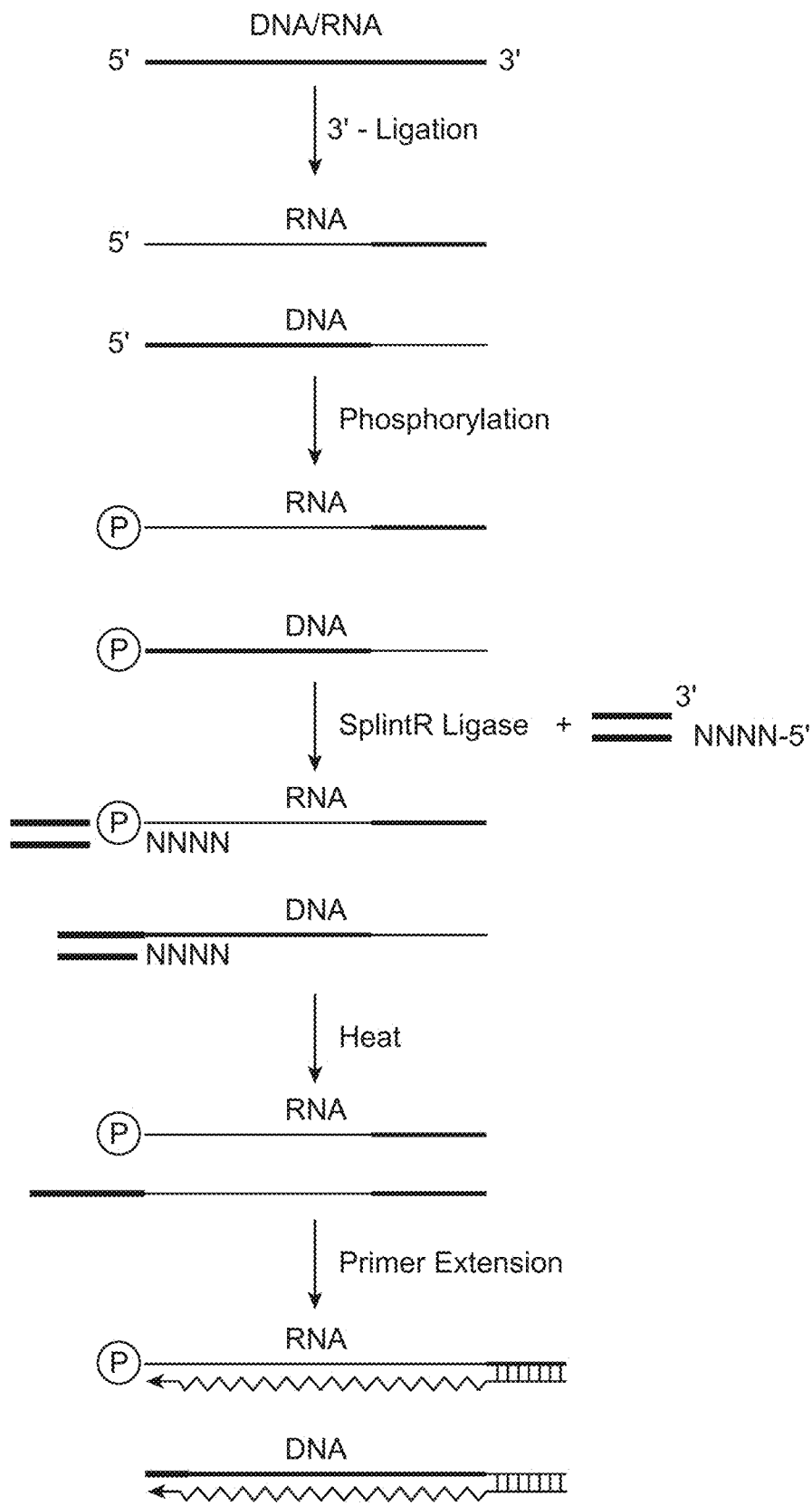
FIG. 20 depicts splint ligase approaches to detect various nucleic acid forms in a sample.

In FIG. 20, the depicted splint adapter has a 5'-end overhang of degenerate bases. All 5'-ends of this adapter are deactivated against ligation. Similarly the 3'-end that is not indicated in the FIG. 20 is also deactivated against ligation. Such a splint adapter can hybridize to 5'-ends of any nucleic acids (i.e. RNA and DNA), but gets successfully ligated by SplintR Ligase only to the nucleic acids that have a 5'-phosphate DNA end.

In general, the method can comprise splint ligation molecule with a SplintR Ligase where the splint ligation molecule is attached to the 5' ends of the DNA and/or RNA within a sample. In some embodiments, the splint ligation molecules are protected so that only the intended ends are ligatable. The SplintR Ligase preference for the 5' DNA over the 5' RNA allows heat treatment to detach the splint ligation molecule on only the 5' RNA. Subsequently, a primer extension method can be conducted on both the DNA ligated to the splint ligation molecule and non-ligated free RNA, thereby allowing one to distinguish between the RNA and DNA molecules in the sample. Non-limiting examples of ligases that can be used are T4 DNA Ligase, T4 RNA Ligase 2, SplintR Ligase, or the like.

In some embodiments, a splint ligase method can comprise the following steps: denaturation of the nucleic acids forms in a sample, followed by a first adapter ligation step as shown in (e.g., FIG. 1, Step 120). Next, the 5'-ends of RNA and DNA may be phosphorylated using kinase (e.g., T4 PNK or the like), so that a DNA-specific sequence can be added to the 5'-end. Next, a splint adapter with 5'-end randomized overhang and SplintR Ligase can be used to ligate DNA-specific sequence to the 5'-end of DNA, leaving 5'-end of RNA lacking the DNA-specific sequence as SplintR Ligase will not process phosphorylated 5'-ends of RNA. After, heat is applied to remove any SplintR Ligase from the RNA. Finally, one can proceed with the steps shown in FIG. 1 starting with 130 to 150, FIG. 20.

H. Efficiency of Sample Recovery

The methods of the disclosure provide more efficient recovery of the input staring sample (e.g., before processing). That is, the nucleic acids of the starting sample are recovered in the final sample (e.g., after processing) at a higher percentage when compared to other nucleic acid sample processing kits, FIG. 14 and FIG. 15.

In some embodiments, the methods of the disclosure provide recovery of the starting sample is about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 percent recovery of the nucleic acids from the sample compared to the final processed sample.

VIII. Single Reaction Mixture Compositions

The present disclosure provides reaction mixtures. In general, a single reaction mixture can generate nucleic acid products directed to different nucleic acid forms in a sample using a single reaction mixture.

In some applications, the single reaction mixture is provided in a single liquid or dry format. In other applications, the single reaction mixture is provided in a multiple liquid or dry formats, or a combination thereof.

In some embodiments, a single reaction mixture can require one or more purification steps. Purification of a single reaction mixture can be accomplished with the use of one or more labels on the adaptors which can be used for purification steps during the single reaction method for optimal buffer environments for a given enzymes. In some embodiments, a single reaction mixture of the present disclosure has no purification steps.

In some embodiments, a single reaction mixture can comprise an adapter, a ligase that has a preference for a nucleic acid form, and a buffer. In some embodiments, a single reaction mixture can comprise an adapter, a ligase that has a preference for a nucleic acid form, a buffer and a DNA-dependent polymerase.

The ligase in a single reaction mixture can have a preference for a particular nucleic acid form. A ligase can have a preference for DNA over RNA. A ligase can have a preference for RNA over DNA. A ligase can have a preference for a single-stranded nucleic acid over a double-stranded nucleic acid. A ligase can have a preference for a double-stranded nucleic acid over a single-stranded nucleic acid.

Examples of ligases that can be used in a single reaction mixture include but are not limited to, T4 DNA Ligase, T3 DNA Ligase, T7 DNA Ligase, E. coli DNA Ligase, HiFi Taq DNA Ligase, 9° N™ DNA Ligase, Taq DNA Ligase, SplintR® Ligase, Thermostable 5' AppDNA/RNA Ligase, T4 RNA Ligase, T4 RNA Ligase 2, T4 RNA Ligase 2 Truncated, T4 RNA Ligase 2 Truncated K227Q, T4 RNA Ligase 2, Truncated KQ, RtcB Ligase, CircLigase II, CircLigase ssDNA Ligase, CircLigase RNA Ligase, Ampligase® Thermostable DNA Ligase or a combination thereof.

The polymerase in the single reaction mixture can have a preference or be dependent on a particular nucleic acid form. For example, polymerase can be a DNA polymerase or a RT polymerase that is DNA-dependent. In some other embodiment the polymerase can be a RNA-dependent.

Examples of DNA polymerase that can be used in a single reaction mixture include but are not limited to Bst DNA Polymerase, Full Length, Bst DNA Polymerase, Large Fragment, Bsu DNA Polymerase, Crimson Taq DNA Polymerase, Large Fragment, Deep VentR™ (NEB) DNA Polymerase, Deep VentR™ (exo-) (NEB) DNA Polymerase, E. coli DNA Polymerase I, Klenow Fragment (3'→5' exo-), DNA Polymerase I, Large (Klenow) Fragment, LongAmp® Taq DNA Polymerase or Hot Start (NEB), M-MuLV Reverse Transcriptase, OneTaq® DNA Polymerase or Hot Start (NEB), phi29 DNA Polymerase, Phusion® Hot Start Flex DNA Polymerase (NEB), Phusion® High-Fidelity DNA Polymerase (NEB), Q5®+Q5® Hot Start DNA Polymerase (NEB), Sulfolobus DNA Polymerase IV, T4 DNA Polymerase, T7 DNA Polymerase (unmodified), Taq DNA Polymerase, or Therminator™ DNA Polymerase (NEB), VentR® DNA Polymerase (NEB), or VentR® (exo-) DNA Polymerase (NEB), or a modified form such that its preference for a nucleic acid form or its strand displacing activity is increased. In some embodiments, the single reaction mixture can include a combination of DNA polymerases.

Non-limiting examples of RT polymerases that can be used in a single reaction mixture include but are not limited to WarmStart RTx Reverse Transcriptase(NEB), AMV Reverse Transcriptase (NEB), Superscript IV RT (Invitrogen), M-MLV Rnase H(-) (Promega), SMARTer reverse transcriptase (Clontech), and RevertAid RnaseH(-) RT (Thermo Scientific), ProtoScript® II Reverse Transcriptase (NEB), or a modified form such that its preference for a nucleic acid form or its strand displacing activity is increased. In some embodiments, the single reaction mixture can include a combination of RT polymerases.

The single desired product regardless of the starting substrate form (e.g., DNA, RNA or DNA/RNA hybrids). While it may be preferred for ease that a single reaction mixture be subject to a single set of reaction conditions to be able to ligate and/or replicate DNA and RNA fragments, it will be appreciated that in some cases, one may alter the buffer conditions applied to the reaction mixture at one or more different steps to achieve a desired level of activity in a reaction. For example, depending on the particular reaction to be optimized one may change, for example, the temperature, divalent co-factors, changing salt concentration, or addition of one or more additional reagents to a given reaction mixture at different stages to improve the ligation and/or replication of one of the forms of nucleic acid in the mixture.

In some embodiments, a reaction mixture can comprise a ligase, a DNA-dependent polymerase that has non-templated activity, wherein the non-templated base is N1, a RT polymerase that has non-templated activity, wherein the non-templated base is N2, wherein N1 and N2 are different nucleic acid bases.

Non-limiting examples of DNA-dependent that can be used in the reaction mixture are: A- and B-family DNA polymerases, KOD XL, KOD (exo-), Bst 2.0, Therminator, Deep Vent (exo-), Pfu DNA polymerase, or Taq.

Non-limiting examples of reverse transcriptase that can be used in the reaction mixture are: HIV reverse transcriptase, Moloney murine leukemia virus, SuperScript II™ (Thermo-Fisher), or SuperScript III™.

IX. Detection

The methods of the disclosure can include detection of the nucleic acids forms attached to the adapters provided by the present disclosure. The disclosure also provides methods of analysis (e.g., bioinformatics) after detection. Detection can be performed by any means known in the art for nucleic acid detection or future means for nucleic acid detection. Non-limiting examples of detection means which can be used are various forms of sequencing, qPCR, ddPCR, microfluidic device, or microarray.

A. Sequencing

The methods of the disclosure include the use of a nucleic acid sequencer system (e.g., DNA sequencer, RNA sequencer). The system may include a computer comprising software that performs bioinformatics analysis on the sequence information. Bioinformatics analysis can include, without limitation, assembling sequence data, detecting and quantifying genetic variants in a sample, including germline variants and somatic cell variants (e.g., a genetic variation associated with cancer or pre-cancerous condition, a genetic variation associated with infection).

This disclosure provides methods of analyzing nucleic acids, particularly different forms of nucleic acids present in the same sample. Such analytical methods including sequencing the nucleic acids as well as bioinformatics analysis of the sequencing results. The nucleic acids produced according the present methods may be analyzed to obtain various types of information including genomic and RNA expression. Generally, the analyses provided herein allow for simultaneous analysis of DNA and RNA in a sample, as well as both single- and double-stranded nucleic acids in a sample. In some cases, the analysis detects both DNA and RNA, yet does not distinguish between the two. In some cases, the analysis detects both DNA and RNA (or double- and single-stranded nucleic acids) and also identifies whether the originating molecules are DNA, RNA, ssDNA, dsDNA, ssRNA, dsRNA, in any combination. Often, the distinguishing is accomplished by detecting markers added to the nucleic acids using adapters described herein.

In some embodiments, the sequencing is performed using a next generation sequencing assay. As used herein, the term "next generation" generally refers to any massive, high-throughput sequencing approach including, but not limited to one or more of the following: massively-parallel signature sequencing, pyrosequencing (e.g., using a Roche 454 sequencing device), Illumina (Solexa) sequencing, sequencing by synthesis (Illumina), Ion torrent sequencing, sequencing by ligation (e.g., SOLiD sequencing), single molecule real-time (SNRT) sequencing (e.g., Pacific Bioscience), polony sequencing, DNA nanoball sequencing, heliscope single molecule sequencing (Helicos Biosciences), and nanopore sequencing (e.g., Oxford Nanopore). In some cases, the sequencing assay uses nanopore sequencing. In some cases, the sequencing assay includes some form of Sanger sequencing. In some cases, the sequencing involves shotgun sequencing, in some cases, the sequencing includes bridge PCR. In some cases, the sequencing is broad spectrum. In some cases, the sequencing is targeted.

In some cases, the sequencing assay comprises a Gilbert's sequencing method. In such approach, nucleic acids (e.g., DNA) are chemically modified and then cleaved at specific bases. In some cases, a sequencing assay comprises dideoxynucleotide chain termination or Sanger-sequencing.

A sequencing-by-synthesis approach may be used in the methods provided herein. In some cases, fluorescently-labeled reversible-terminator nucleotides are introduced to clonally-amplified DNA templates immobilized on the surface of a glass flowcell. During each sequencing cycle, a single labeled deoxynucleoside triphosphate (dNTP) may be added to the nucleic acid chain. The labeled terminator nucleotide may be imaged when added in order to identify the base and may then be enzymatically cleaved to allow incorporation of the next nucleotide. Since all four reversible terminator-bound dNTPs (A, C, T, G) are generally present as single, separate molecules, natural competition may minimize incorporation bias.

In some cases, a method called Single-molecule real-time (SMRT) is used. In such approach, nucleic acids (e.g., DNA) are synthesized in zero-mode wave-guides (ZMWs), which are small well-like containers with capturing tools located at the bottom of the well. The sequencing is performed with use of unmodified polymerase (attached to the ZMW bottom) and fluorescently labelled nucleotides flowing freely in the solution. The fluorescent label is detached from the nucleotide upon its incorporation into the DNA strand, leaving an unmodified DNA strand. A detector such as a camera may then be used to detect the light emissions, and the data may be analyzed bioinformatically to obtain sequence information.

In some cases, a sequencing by ligation approach is used to sequence the nucleic acids in a sample. One example is the next generation sequencing method of SOLiD (Sequencing by Oligonucleotide Ligation and Detection) sequencing (Life Technologies). This next generation technology may generate hundreds of millions to billions of small sequence reads at one time. The sequencing method may comprise preparing a library of DNA fragments from the sample to be sequenced. In some cases, the library is used to prepare clonal bead populations in which only one species of fragment is present on the surface of each bead (e.g., magnetic bead). The fragments attached to the magnetic beads may have a universal P1 adapter sequence attached so that the starting sequence of every fragment is both known and identical. In some cases, the method may further involve PCR or emulsion PCR. For example, the emulsion PCR may involve the use of microreactors containing reagents for PCR. The resulting PCR products attached to the beads may then be covalently bound to a glass slide. A sequencing assay such as a SOLiD sequencing assay or other sequencing by ligation assay may include a step involving the use of primers. Primers may hybridize to the P1 adapter sequence or other sequence within the library template. The method may further involve introducing four fluorescently labelled di-base probes that compete for ligation to the sequencing primer. Specificity of the di-base probe may be achieved by interrogating every first and second base in each ligation reaction. Multiple cycles of ligation, detection and cleavage may be performed with the number of cycles determining the eventual read length. In some cases, following a series of ligation cycles, the extension product is removed and the template is reset with a primer complementary to the n−1 position for a second round of ligation cycles. Multiple rounds (e.g., 5 rounds) of primer reset may be completed for each sequence tag. Through the primer reset process, each base may be interrogated in two independent ligation reactions by two different primers. For example, the base at read position 5 is assayed by primer number 2 in ligation cycle 2 and by primer number 3 in ligation cycle 1.

Sequencing using high-throughput systems may allow detection of a sequenced nucleotide immediately after or upon its incorporation into a growing strand, e.g., detection of sequence in real time or substantially real time. In some cases, high throughput sequencing generates at least 1,000, at least 5,000, at least 10,000, at least 20,000, at least 30,000, at least 40,000, at least 50,000, at least 100,000, or at least 500,000 sequence reads per hour. In some cases, each read is at least 50, at least 60, at least 70, at least 80, at least 90, at least 100, at least 120, or at least 150 bases per read. In some cases, each read is up to 2000, up to 1000, up to 900, up to 800, up to 700, up to 600, up to 500, up to 400, up to 300, up to 200, or up to 100 bases per read. Long read sequencing can include sequencing that provides a contiguous sequence read of for example, longer than 500 bases, longer than 800 bases, longer than 1000 bases, longer than 1500 bases, longer than 2000 bases, longer than 3000 bases, or longer than 4500 bases.

In some cases, high-throughput sequencing involves the use of technology available by Illumina's Genome Analyzer IIX, MiSeq personal sequencer, or HiSeq systems, such as those using HiSeq 2500, HiSeq 1500, HiSeq 2000, or HiSeq 1000. These machines use reversible terminator-based sequencing by synthesis chemistry. These machines can do 200 billion DNA or more reads in eight days. Smaller systems may be utilized for runs within 3, 2, or 1 days or less time. Short synthesis cycles may be used to minimize the time it takes to obtain sequencing results.

In some cases, high-throughput sequencing involves the use of technology available by ABI Solid System. This genetic analysis platform can enable massively parallel sequencing of clonally-amplified DNA fragments linked to beads. The sequencing methodology is based on sequential ligation with dye-labeled oligonucleotides.

The next generation sequencing can comprise ion semiconductor sequencing (e.g., using technology from Life Technologies (Ion Torrent)). Ion semiconductor sequencing can take advantage of the fact that when a nucleotide is incorporated into a strand of DNA, an ion can be released. To perform ion semiconductor sequencing, a high density array of micromachined wells can be formed. Each well can hold a single DNA template. Beneath the well can be an ion sensitive layer, and beneath the ion sensitive layer can be an ion sensor. When a nucleotide is added to a DNA, H+ can be released, which can be measured as a change in pH. The H+ ion can be converted to voltage and recorded by the semiconductor sensor. An array chip can be sequentially flooded with one nucleotide after another. No scanning, light, or cameras can be required. In some cases, an ION-PROTON™ Sequencer is used to sequence nucleic acid. In some cases, an IONPGM™ Sequencer is used. The Ion Torrent Personal Genome Machine (PGM) can do 10 million reads in two hours.

In some cases, high-throughput sequencing involves the use of technology available by Helicos BioSciences Corporation (Cambridge, Mass.) such as the Single Molecule Sequencing by Synthesis (SMSS) method. SMSS can allow for sequencing the entire human genome in up to 24 hours. SMSS, like the MIP technology, may not require a pre-amplification step prior to hybridization. SMSS may not require any amplification. SMSS is described in part in US Publication Application Nos. 20060024711, 20060024678, 20060012793, 20060012784, and 20050100932.

In some cases, high-throughput sequencing involves the use of technology available by 454 Lifesciences, Inc. (Branford, Conn.) such as the Pico Titer Plate device which includes a fiber optic plate that transmits chemiluminescent signal generated by the sequencing reaction to be recorded by a CCD camera in the instrument. This use of fiber optics can allow for the detection of a minimum of 20 million base pairs in 4.5 hours.

Methods for using bead amplification followed by fiber optics detection are described in Marguiles, M., et al. "Genome sequencing in microfabricated high-density picolitre reactors", Nature, doi: 10.1038/nature03959, and well as in US Publication Application Nos. 20020012930, 20030058629, 20030100102, 20030148344, 20040248161, 20050079510, 20050124022, and 20060078909.

In some cases, high-throughput sequencing is performed using Clonal Single Molecule Array (Solexa, Inc.) or sequencing-by-synthesis (SBS) utilizing reversible terminator chemistry. These technologies are described in part in U.S. Pat. Nos. 6,969,488, 6,897,023, 6,833,246, 6,787,308, and US Publication Application Nos. 20040106110, 20030064398, 20030022207, and Constans, A., The Scientist 2003, 17(13):36.

In some cases, the next generation sequencing is nanopore sequencing (See e.g., Soni GV and Meller A. (2007) Clin Chem 53: 1996-2001). A nanopore can be a small hole, e.g., on the order of about one nanometer in diameter. Immersion of a nanopore in a conducting fluid and application of a potential across it can result in a slight electrical current due to conduction of ions through the nanopore. The amount of current which flows can be sensitive to the size of the nanopore. As a DNA molecule passes through a nanopore, each nucleotide on the DNA molecule can obstruct the nanopore to a different degree. Thus, the change in the current passing through the nanopore as the DNA molecule passes through the nanopore can represent a reading of the DNA sequence. The nanopore sequencing technology can be from Oxford Nanopore Technologies, e.g., a GridION system. A single nanopore can be inserted in a polymer membrane across the top of a microwell. Each microwell can have an electrode for individual sensing. The microwells can be fabricated into an array chip, with 100,000 or more microwells (e.g., more than 200,000, 300,000, 400,000, 500,000, 600,000, 700,000, 800,000, 900,000, or 1,000,000) per chip. An instrument (or node) can be used to analyze the chip. Data can be analyzed in real-time. One or more instruments can be operated at a time. The nanopore can be a protein nanopore, e.g., the protein alpha-hemolysin, a heptameric protein pore. The nanopore can be a solid-state nanopore made, e.g., a nanometer sized hole formed in a synthetic membrane (e.g., SiNx, or SiO2). The nanopore can be a hybrid pore (e.g., an integration of a protein pore into a solid-state membrane). The nanopore can be a nanopore with an integrated sensors (e.g., tunneling electrode detectors, capacitive detectors, or graphene based nano-gap or edge state detectors (see e.g., Garaj et al. (2010) Nature vol. 67, doi: 10.1038/nature09379)). A nanopore can be functionalized for analyzing a specific type of molecule (e.g., DNA, RNA, or protein). Nanopore sequencing can comprise "strand sequencing" in which intact DNA polymers can be passed through a protein nanopore with sequencing in real time as the DNA translocates the pore. An enzyme can separate strands of a double stranded DNA and feed a strand through a nanopore. The DNA can have a hairpin at one end, and the system can read both strands. In some cases, nanopore sequencing is "exonuclease sequencing" in which individual nucleotides can be cleaved from a DNA strand by a processive exonuclease, and the nucleotides can be passed through a protein nanopore. The nucleotides can transiently bind to a molecule in the pore (e.g., cyclodextran). A characteristic disruption in current can be used to identify bases.

Nanopore sequencing technology from GENIA can be used. An engineered protein pore can be embedded in a lipid bilayer membrane. "Active Control" technology can be used to enable efficient nanopore-membrane assembly and control of DNA movement through the channel. In some cases, the nanopore sequencing technology is from NABsys. Genomic DNA can be fragmented into strands of average length of about 100 kb. The 100 kb fragments can be made single stranded and subsequently hybridized with a 6-mer probe. The genomic fragments with probes can be driven through a nanopore, which can create a current-versus-time tracing. The current tracing can provide the positions of the probes on each genomic fragment. The genomic fragments can be lined up to create a probe map for the genome. The process can be done in parallel for a library of probes. A genome-length probe map for each probe can be generated. Errors can be fixed with a process termed "moving window Sequencing By Hybridization (mwSBH)." In some cases, the nanopore sequencing technology is from IBM/Roche. An electron beam can be used to make a nanopore sized opening in a microchip. An electrical field can be used to pull or thread DNA through the nanopore. A DNA transistor device in the nanopore can comprise alternating nanometer sized layers of metal and dielectric. Discrete charges in the DNA backbone can get trapped by electrical fields inside the DNA nanopore. Turning off and on gate voltages can allow the DNA sequence to be read.

The next generation sequencing can comprise DNA nanoball sequencing (as performed, e.g., by Complete Genomics, see e.g., Drmanac et al. (2010) Science 327: 78-81). DNA can be isolated, fragmented, and size selected. For example, DNA can be fragmented (e.g., by sonication) to a mean length of about 500 bp. Adaptors (Ad1) can be attached to the ends of the fragments. The adaptors can be used to hybridize to anchors for sequencing reactions. DNA with adaptors bound to each end can be PCR amplified. The adaptor sequences can be modified so that complementary single strand ends bind to each other forming circular DNA. The DNA can be methylated to protect it from cleavage by a type IIS restriction enzyme used in a subsequent step. An adaptor (e.g., the right adaptor) can have a restriction recognition site, and the restriction recognition site can remain non-methylated. The non-methylated restriction recognition site in the adaptor can be recognized by a restriction enzyme (e.g., AcuI), and the DNA can be cleaved by AcuI 13 bp to the right of the right adaptor to form linear double stranded DNA. A second round of right and left adaptors (Ad2) can be ligated onto either end of the linear DNA, and all DNA with both adapters bound can be PCR amplified (e.g., by PCR). Ad2 sequences can be modified to allow them to bind each other and form circular DNA. The DNA can be methylated, but a restriction enzyme recognition site can remain non-methylated on the left Ad1 adapter. A restriction enzyme (e.g., AcuI) can be applied, and the DNA can be cleaved 13 bp to the left of the Ad1 to form a linear DNA fragment. A third round of right and left adaptor (Ad3) can be ligated to the right and left flank of the linear DNA, and the resulting fragment can be PCR amplified. The adaptors can be modified so that they can bind to each other and form circular DNA. A type III restriction enzyme (e.g., EcoP15) can be added, EcoP15 can cleave the DNA 26 bp to the left of Ad3 and 26 bp to the right of Ad2. This cleavage can remove a large segment of DNA and linearize the DNA once again. A fourth round of right and left adaptors (Ad4) can be ligated to the DNA, the DNA can be amplified (e.g., by PCR), and modified so that they bind each other and form the completed circular DNA template.

Rolling circle replication (e.g., using Phi 29 DNA polymerase) can be used to amplify small fragments of DNA. The four adaptor sequences can contain palindromic sequences that can hybridize and a single strand can fold onto itself to form a DNA nanoball (DNB™) which can be approximately 200-300 nanometers in diameter on average. A DNA nanoball can be attached (e.g., by adsorption) to a microarray (sequencing flowcell). The flow cell can be a silicon wafer coated with silicon dioxide, titanium and hexamehtyldisilazane (HMDS) and a photoresist material. Sequencing can be performed by unchained sequencing by ligating fluorescent probes to the DNA. The color of the fluorescence of an interrogated position can be visualized by a high resolution camera. The identity of nucleotide sequences between adaptor sequences can be determined.

B. PCR-Based Detection Methods

Various PCR-based detection methods can be used with the methods provided by the present disclosure. Examples of such methods include but are not limited to, sequencing-by-synthesis, digital PCR, ddPCR, or quantitative PCR. In addition, one or all the steps of the methods provided by the disclosure can be carried out on a microfluidic device.

C. Microarray

The methods of the present disclosure can be detected by microarray. Microarray maybe desirable targeted applications. In this case, the probes of the array can be designed to have sequences complementary to segments the targets of interest and the adapters provided by the present disclosure can be labeled with two different fluorophores so that the microarray apparatus can distinguish between two different nucleic acid forms.

X. Systems

The methods of the disclosure can include a system. A system can include an apparatus for detection and/or computer control systems with machine-executable instructions to implement the methods. In some embodiments, the computer control systems are further programmed for conducting genetic analysis.

Detection systems that can be used with the methods of the present disclosure can include but are not limited to sequencing, digital PCR, ddPCR, quantitative PCR (e.g. real-time PCR) or by a microfluidic device, microarray, or the like.

A. Hardware Systems

Sequencing

A system can include a nucleic acid sequencer (e.g., DNA sequencer, RNA sequencer) for generating DNA or RNA sequence information. The system may further include a computer comprising software that performs bioinformatics analysis on the DNA or RNA sequence information. Bioinformatics analysis can include, without limitation, assembling sequence data, detecting and quantifying genetic variants in a sample, including germline variants and somatic cell variants (e.g., a genetic variation associated with cancer or pre-cancerous condition, a genetic variation associated with infection).

Sequencing data may be used to determine genetic sequence information, ploidy states, the identity of one or more genetic variants, as well as a quantitative measure of the variants, including relative and absolute relative measures. In some cases, sequencing of the genome involves whole genome sequencing or partial genome sequencing. The sequencing may be unbiased and may involve sequencing all or substantially all (e.g., greater than 70%, 80%, 90%) of the nucleic acids in a sample. Sequencing of the genome can be selective, e.g., directed to portions of the genome of interest. For example, many genes (and mutant forms of these genes) are known to be associated with various cancers. Sequencing of select genes, or portions of genes may suffice for the analysis desired. Polynucleotides mapping to specific loci in the genome that are the subject of interest can be isolated for sequencing by, for example, sequence capture or site-specific amplification.

Digital PCR

In some applications, a system can include an apparatus for digital PCR or droplet based digital PCR. A digital PCR assay can be multiplex, such that two or more different analytes or nucleic acid forms are detected within a single partition (e.g. reaction mixture). Amplification of the analytes can be distinguished by utilizing analyte-specific probes labeled with different fluorophores or dyes. A digital PCR machine may comprise a detector the can distinguishably measure the fluorescence of the different labels, and thereby detect different analytes.

Measurements can include the determination of copy number, copy number variation (e.g., to detect trisomy condition), the status of a single nucleotide polymorphisms, deletions, duplications, translocations, and/or inversions, which can be the source of disease, susceptibility to disease and/or responsiveness to particular therapeutic treatment.

Real-Time PCR Methodologies

In some applications a system can include an apparatus for real-time PCR (or quantitative PCR (qPCR). A real-time polymerase chain reaction can be configured for multiplexing by using emission differences of between two or more fluorescent probes or dyes.

Microarray

In some applications, a system can include an apparatus for microarray detection. Microarray maybe desirable in cases where the methods are being applied in a targeted fashion. In some applications, arrays may be subdivided with a gasket into subarrays.

A microarray is device generally contains short single-stranded oligonucleotide probes (e.g., 25- to 70-bp in length) attached to a solid substrate. The probes can be designed to have sequences complementary to the targets of interest. Targeted oligos can be added the microarray by spotting, spraying, or synthesized in situ through a series of photo-catalyzed reactions.

Microfluidic Devices

In some applications, a system can include a microfluidic apparatus for carrying put the methods of the disclosure. A microfluidic device used with the methods of the disclosure can be configured to perform various amplification assays including PCR, qPCR, or RT-PCR. In some applications, the microfluidic device can also can be configured to integrate pre-PCR or post-PCR assays.

B. Computer Control Systems

Figure 19:
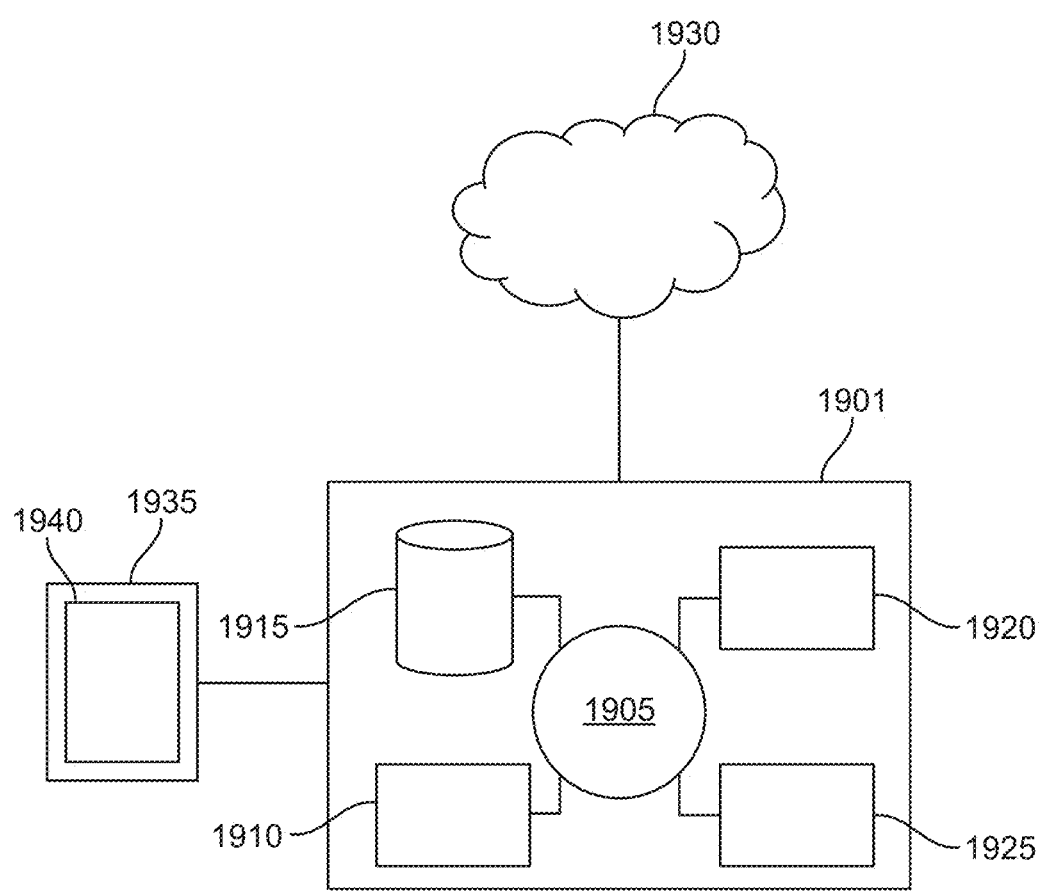
FIG. 19 depicts a computer control system that is programmed or otherwise configured to implement the methods and systems provided herein.

The disclosure also provides computer control systems programmed to implement the methods of the disclosure. FIG. 19 shows a computer system 1901 that is programmed or otherwise configured to implement methods of the present disclosure.

The computer system 1901 includes a central processing unit (CPU, also "processor" and "computer processor" herein) 1905, which can be a single core or multi core processor, or a plurality of processors for parallel processing. The computer system 1901 also includes memory or memory location 1910 (e.g., random-access memory, read-only memory, flash memory), electronic storage unit 1915 (e.g., hard disk), communication interface 1920 (e.g., network adapter) for communicating with one or more other systems, and peripheral devices 1925, such as cache, other memory, data storage and/or electronic display adapters. The memory 1910, storage unit 1915, interface 1920 and peripheral devices 1925 are in communication with the CPU 1905 through a communication bus (solid lines), such as a motherboard. The storage unit 1915 can be a data storage unit (or data repository) for storing data. The computer system 1901 can be operatively coupled to a computer network ("network") 1930 with the aid of the communication interface 1920. The network 1930 can be the Internet, an internet and/or extranet, or an intranet and/or extranet that is in communication with the Internet. The network 1930 in some cases is a telecommunication and/or data network. The network 1930 can include one or more computer servers, which can enable distributed computing, such as cloud computing. The network 1930, in some cases with the aid of the computer system 1901, can implement a peer-to-peer network, which may enable devices coupled to the computer system 1901 to behave as a client or a server.

The CPU 1905 can execute a sequence of machine-readable instructions, which can be embodied in a program or software. The instructions may be stored in a memory location, such as the memory 1910. The instructions can be directed to the CPU 1905, which can subsequently program or otherwise configure the CPU 1905 to implement methods of the present disclosure. Examples of operations performed by the CPU 1905 can include fetch, decode, execute, and writeback.

The CPU 1905 can be part of a circuit, such as an integrated circuit. One or more other components of the system 1901 can be included in the circuit. In some cases, the circuit is an application specific integrated circuit (ASIC).

The storage unit 1915 can store files, such as drivers, libraries and saved programs. The storage unit 1915 can store user data, e.g., user preferences and user programs. The computer system 1901 in some cases can include one or more additional data storage units that are external to the computer system 1901, such as located on a remote server that is in communication with the computer system 1901 through an intranet or the Internet.

The computer system 1901 can communicate with one or more remote computer systems through the network 1930. For instance, the computer system 1901 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 1901 via the network 1930.

Methods as described herein can be implemented by way of machine (e.g., computer processor) executable code stored on an electronic storage location of the computer system 1901, such as, for example, on the memory 1910 or electronic storage unit 1915. The machine executable or machine readable code can be provided in the form of software. During use, the code can be executed by the processor 1905. In some cases, the code can be retrieved from the storage unit 1915 and stored on the memory 1910 for ready access by the processor 1905. In some situations, the electronic storage unit 1915 can be precluded, and machine-executable instructions are stored on memory 1910.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 1901, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1901 can include or be in communication with an electronic display 1935 that comprises a user interface (UI) 1940 for providing, an output of a report, which may include a diagnosis of a subject or a therapeutic intervention for the subject. Examples of UI's include, without limitation, a graphical user interface (GUI) and web-based user interface. The analysis can be provided as a report. The report may be provided to a subject, to a health care professional, a lab-worker, or other individual.

Methods and systems of the present disclosure can be implemented by way of one or more algorithms. An algorithm can be implemented by way of software upon execution by the central processing unit 1905. The algorithm can, for example, facilitate the enrichment, sequencing and/or detection of pathogen or other target nucleic acids.

Information about a patient or subject can be entered into a computer system, for example, patient background, patient medical history, or medical scans. The computer system can be used to analyze results from a method described herein, report results to a patient or doctor, or come up with a treatment plan.

XI. Applications

The methods, composition, systems, and kits of the disclosure can be used for a variety of applications including personalized medicine, treatment, of any disorders that have a genetic component to drive its pathogenesis or progression. Specifically, the methods of the disclosure can be applied to a sample to detect, monitor, diagnose, prognose, guide treatment, or predict the risk of disease.

A. Cancer

The methods of the disclosure can be used for detecting cancer in a subject or for cancer diagnosis. Samples maybe either somatic, germline, or a combination thereof. Samples can be from blood, tissue, or any sample known to harbor the cancer mutation. Cancer cells in the blood can be cell-free nucleic acids or as circulating cancer cells, such as circulating tumor cells (CTCs), cancer stem cells (CSC), hematopoietic stem cells (HSC), and/or endothelial progenitor cells (EPC). The methods can be used to detect any type circulating cancer cell or cell-free nucleic acids (e.g., DNA or RNA) associated with a tumor.

The methods for cancer can be targeted or non-targeted. In some cases, the methods provided herein can be used to detect specific genes or mutations of interest in the tumor that can be used in the diagnosis or tailoring a cancer treatment for a subject. Such mutations, can include but are not limited to a mutation associated with cancer progression, drug response, methylation, or a specific cancer gene of interest.

Examples of cancer genes that can be used with the disclosure include but are not limited to, TP53, CA-125, CEA, PSA, AKT1, ALK, APC, AR, ARAF, ARID1A, ATM, BRAF, BRCA1, BRCA2, CCND1, CCND2, CCNE1, CDH, CDK4, CDK6, CDKN2A, CTNNB1, DDR2, EGFR, ERBB2, ESR1, EZH2, FBXW7, FGFR, FGFR, FGFR3, GATA3, GNA11, GNAQ, GNAS, HNF1A, HRAS, IDH1, IDH2, JAK2, JAK3, KIT, KRAS, MAP2K1, MAP2K2, MAPK1, MAPK3, MET, MLH1, MPL, MTOR, MYC, NF1, NFE2L2, NOTCH1, NPM1, NRAS, NTRK1, NTRK3, PDGFRA, PIK3CA, PTEN, PTPN1, RAF, RB1, RET, RHEB, RHOA, RIT1, ROS1, SMAD4, SMO, STK1, TERT, TSC1, or VHL or any other genes associated with cancer progression.

C. Fetal Health

The methods can be used for detection, diagnosis, or prognosis of fetal health (e.g., a IVF embryo or a fetus) in a subject. In some cases, the methods can be used to determine or assess the risk of infection status of an embryo or fetus. In some cases, the methods can be used for the genetic assessment for chromosomal aberrations, an inherited condition including but not limited to, autosomal-recessive, dominant, X-linked, or SNP-based genetic conditions in a subject.

The methods for fetal health can be targeted or non-targeted. Non-limiting examples of fetal health conditions that can be used with the disclosure include, Rh factor, sex of the fetus, Down syndrome (trisomy 21), Trisomy 18, Trisomy 13, Trisomy 16, Trisomy 22, Sex chromosome aneuploidy, or certain genetic disorders or inherited condition such as, for example, Prader-Willi syndrome and the like.

D. Infection

The methods can be used for detecting a pathogenic infection in a subject. In some applications, the methods may provide a more comprehensive view of the state and diversity of the infection in a subject. For example, the identification of both RNA and DNA in a sample may be useful to detect both RNA and DNA type viruses, as well as bacterial or fungal genomic DNA and transcriptomic RNA. Such process may also be able to differentiate between latent infection (e.g., which might be indicated by the presence of integrated retroviral DNA) versus active infection (e.g., which might be indicated by the presence of viral RNA from intact viral particles). Such analyses may include analysis of cell-free, circulating nucleic acids, or degraded nucleic acids e.g., for microbial or viral infection identification.

In addition, the approaches provided herein may yield information about particle-protected nucleic acids, e.g., in exosomes or intact pathogens.

In an infected sample, nucleic acid forms within a given sample may include a variety of different structural forms and hybrids of those forms, including DNA and RNA, single and double-stranded forms of these, and structured and unstructured forms of these. By way of example, in the case of pathogen identification, it will be appreciated that pathogenic organisms may include a variety of chemical and/or structural forms of nucleic acids that may be used in their identification.

For example, bacterial and fungal pathogens may include both DNA-based genomes and RNA-based transcriptomes, which may be used in their identification. Likewise, viral pathogens may include DNA-based genomes, including, e.g., dsDNA viruses (~24% of viruses) such as human herpes virus 6, ssDNA viruses (~9% of viruses) such as microphages, and dsDNA RT viruses (~3% of viruses) such as the hepatitis B virus, or RNA-based genomes, including ssRNA retroviruses (~6% of viruses) like HIV, dsRNA viruses (~9% of viruses) like Rotavirus, (~) ssRNA viruses (~18% of viruses) such as the Ebola virus, (+) ssRNA viruses (~26% of viruses) like the Hepatitis C virus, and ambisense viruses (~5% of viruses) like the Lassa virus.

The methods for detection of an infection can be targeted or non-targeted. Examples of pathogen infections that can be used with the methods of the disclosure include but are not limited to, *Nocardia* species, *Legionella* species, *Rickettsia* species, *Actinomyces* species, *Mycoplasma* species, HACEK organisms (including *Haemophilus parainfluenzae,* *Aggregatibacter aphrophilus, Aggregatibacter actinomycetemcomitans, Cardiobacterium hominis, Eikenella corrodens,* and *Kingella kingae*), *Streptobacillus moniliformis, Mycobacterium tuberculosis* complex, *Mycobacterium avium* complex including *M. chimaera,* Other nontuberculous mycobacteria, *Candida* species, *Candida auris, Penicillium* species, *Aspergillus* species, *Fusarium* species, *Mucor* species, *Rhizopus* species, *Rhizomucor* species, *Scedosporium* species, *Blastomyces dermatitidis, Coccidioides immitis, Histoplasma capsulatum, Cryptococcus neoformans* and *gattii, Pneumocystis jirovecii,* Protozoa, *Plasmodium* species, *Toxoplasma gondii, Acanthamoeba castellanii, Balamuthia mandrillaris, Naegleria* fowler, CMV, EBV, Adenovirus, BK Polyomavirus, JC Polyomavirus, Torque Teno Viruses, Abiotrophia defective, *Absidia glauca, Acanthamoeba castellanii, Achromobacter denitrificans, Achromobacter xylosoxidans,* Acidaminococcus intestine, *Acidovorax citrulli, Acinetobacter baumannii, Acinetobacter bereziniae, Acinetobacter calcoaceticus, Acinetobacter haemolyticus, Acinetobacter pittii, Acinetobacter radioresistens, Acinetobacter ursingii, Acremonium chrysogenum, Acremonium furcatum, Actinobacillus ureae, Actinomadura Latina, Actinomadura madurae, Actinomucor elegans, Actinomyces cardiffensis, Actinomyces europaeus, Actinomyces georgiae, Actinomyces gerencseriae, Actinomyces graevenitzii, Actinomyces israelii, Actinomyces massiliensis, Actinomyces meyeri, Actinomyces neuii, Actinomyces odontolyticus, Actinomyces oris, Actinomyces timonensis, Actinomyces turicensis, Actinomyces viscosus,* Adeno-associated dependoparvovirus A, Adeno-associated dependoparvovirus B, *Aerococcus sanguinicola, Aerococcus urinae, Aerococcus viridans, Aeromonas caviae, Aeromonas hydrophila, Aeromonas schubertii, Aeromonas veronii, Aggregatibacter actinomycetemcomitans, Aggregatibacter aphrophilus, Aggregatibacter segnis, Agrobacterium tumefaciens, Alcaligenes faecalis, Alloiococcus otitis, Alloscardovia omnicolens,* Alphapapillomavirus 1, Alphapapillomavirus 2, Alphapapillomavirus 3, Alphapapillomavirus 4, Alphapapillomavirus 5, Alphapapillomavirus 6, Alphapapillomavirus 7, Alphapapillomavirus 8, Alphapapillomavirus 9, Alphapapillomavirus 10, Alphapapillomavirus 11, Alphapapillomavirus 14, *Alternaria* alternate, *Alternaria arborescens, Alternaria brassicicola, Anaerobiospirillum succiniciproducens, Anaerococcus hydrogenalis, Anaerococcus lactolyticus, Anaerococcus prevotii, Anaerococcus tetradius, Anaeroglobus geminatus, Anaplasma phagocytophilum, Angiostrongylus cantonensis, Angiostrongylus costaricensis, Anisakis simplex, Anncaliia algerae, Apophysomyces elegans, Apophysomyces trapeziformis, Arcanobacterium bernardiae, Arcanobacterium haemolyticum, Arcanobacterium pyogenes, Arcobacter butzleri, Arcobacter cryaerophilus, Arcobacter skirrowi, Aspergillus awamori, Aspergillus calidoustus, Aspergillus clavatus, Aspergillus fischeri, Aspergillus flavus, Aspergillus fumigatus, Aspergillus kawachii, Aspergillus lentulus, Aspergillus luchuensis, Aspergillus nidulans, Aspergillus niger, Aspergillus nomius, Aspergillus ochraceoroseus, Aspergillus oryzae, Aspergillus parasiticus, Aspergillus rambellii, Aspergillus sclerotiorum, Aspergillus sojae, Aspergillus terreus, Aspergillus udagawae, Aspergillus ustus, Aspergillus westerdijkiae, Atopobium parvulum, Atopobium rimae, Atopobium vaginae, Aureobasidium melanogenum, Aureobasidium namibiae, Aureobasidium pullulans, Aureobasidium subglaciale, Babesia divergens, Babesia microti, Bacillus anthracis, Bacillus cereus, Bacillus circulans, Bacillus coagulans, Bacillus licheniformis, Bacillus megaterium, Bacillus pumilus, Bacillus sphaericus, Bacillus* subtilis, Bacillus thuringiensis, Bacteroides caccae, Bacteroides distasonis, Bacteroides eggerthii, Bacteroides forsythus, Bacteroides fragilis, Bacteroides merdae, Bacteroides ovatus, Bacteroides stercoris, Bacteroides thetaiotaomicron, Bacteroides uniformis, Bacteroides vulgatus, Balamuthia mandrillaris, Bartonella alsatica, Bartonella bacilliformis, Bartonella birtlesii, Bartonella bovis, Bartonella clarridgeiae, Bartonella doshiae, Bartonella elizabethae, Bartonella grahamii, Bartonella henselae, Bartonella koehlerae, Bartonella quintana, Bartonella rattaustraliani, Bartonella rochalimae, Bartonella schoenbuchensis, Bartonella taylorii, Bartonella tribocorum, Bartonella vinsonii, Basidiobolus meristosporus, Beauveria bassiana, Beauveria rudraprayagi, Bergeyella zoohelcum, Betapapillomavirus 1, Betapapillomavirus 2, Betapapillomavirus 3, Betapapillomavirus 4, Betapapillomavirus 5, Bifidobacterium adolescentis, Bifidobacterium breve, Bifidobacterium dentium, Bifidobacterium longum, Bifidobacterium scardovii, Bipolaris papendorfii, BK polyomavirus, Blastocystis hominis, Blastomyces dermatitidis, Bordetella bronchiseptica, Bordetella hinzii, Bordetella holmesii, Bordetella parapertussis, Bordetella pertussis, Bordetella petrii, Borrelia burgdorferi, Borrelia crocidurae, Borrelia duttonii, Borrelia hermsii, Borrelia hispanica, Borrelia miyamotoi, Borrelia parkeri, Borrelia persica, Borrelia recurrentis, Borrelia turicatae, Borreliella afzelii, Borreliella garinii, Brevibacillus brevis, Brevibacillus laterosporus, Brevibacterium casei, Brevundimonas diminuta, Brevundimonas vesicularis, Brucella abortus, Brucella canis, Brucella melitensis, Brucella suis, Brugia malayi, Burkholderia ambifaria, Burkholderia anthina, Burkholderia cenocepacia, Burkholderia cepacia, Burkholderia gladioli, Burkholderia mallei, Burkholderia multivorans, Burkholderia pseudomallei, Burkholderia pyrrocinia, Burkholderia stabilis, Byssochlamys spectabilis, Campylobacter coli, Campylobacter concisus, Campylobacter corcagiensis, Campylobacter cuniculorum, Campylobacter curvus, Campylobacter fetus, Campylobacter gracilis, Campylobacter hominis, Campylobacter hyointestinalis, Campylobacter iguaniorum, Campylobacter jejuni, Campylobacter lari, Campylobacter mucosalis, Campylobacter showae, Campylobacter sp. MIT 97-5078, Campylobacter sputorum, Campylobacter upsaliensis, Campylobacter ureolyticus, Candida albicans, Candida auris, Candida boidinii, Candida bracarensis, Candida carpophila, Candida castellii, Candida dubliniensis, Candida ethanolica, Candida famata, Candida glabrata, Candida intermedia, Candida kefyr, Candida krusei, Candida lusitaniae, Candida nivariensis, Candida orthopsilosis, Candida parapsilosis, Candida sojae, Candida sorboxylosa, Candida succiphila, Candida tenuis, Candida tropicalis, Candida utilis, Candida versatilis, Capnocytophaga canimorsus, Capnocytophaga cynodegmi, Capnocytophaga gingivalis, Capnocytophaga granulosa, Capnocytophaga haemolytica, Capnocytophaga ochracea, Capnocytophaga sputigena, Cardiobacterium hominis, Cardiobacterium valvarum, Catabacter hongkongensis, Cedecea neteri, Ceratocystis adiposa, Ceratocystis albifundus, Ceratocystis eucalypticola, Ceratocystis fimbriata, Ceratocystis manginecans, Ceratocystis platani, Cercospora fijiensis, Chaetomium globosum, Chaetomium thermophilum, Chlamydia psittaci Chlamydophila psittaci>, Chlamydia trachomatis, Chlamydophila pneumoniae, Chromobacterium violaceum, Chryseobacterium gleum, Chryseobacterium indologenes, Chrysosporium queenslandicum, Citrobacter amalonaticus, Citrobacter freundii, Citrobacter koseri, Cladophialophora bantiana, Cladophialophora carrionii, Cladophialophora immunda, Cladophialophora psammophila, Cladophialophora yegresii, Clonorchis sinensis, Clostridium baratii, Clostridium bifermentans, Clostridium clostridioforme, Clostridium difficile, Clostridium innocuum, Clostridium novyi, Clostridium perfringens, Clostridium sordellii, Clostridium tetani, Coccidioides immitis, Coccidioides posadasii, Cokeromyces recurvatus, Colletotrichum acutatum, Colletotrichum falcatum, Colletotrichum fioriniae, Colletotrichum gloeosporioides, Colletotrichum godetiae, Colletotrichum graminicola, Colletotrichum higginsianum, Colletotrichum incanum, Colletotrichum nymphaeae, Colletotrichum orbiculare, Colletotrichum salicis, Colletotrichum simmondsii, Colletotrichum sublineola, Colletotrichum tofieldiae, Comamonas testosteroni, Conidiobolus coronatus, Conidiobolus incongruus, Coniosporium apollinis, Corynebacterium accolens, Corynebacterium afermentans, Corynebacterium amycolatum, Corynebacterium argentoratense, Corynebacterium aurimucosum, Corynebacterium diphtheriae, Corynebacterium falsenii, Corynebacterium freiburgense, Corynebacterium freneyi, Corynebacterium glucuronolyticum, Corynebacterium jeikeium, Corynebacterium kroppenstedtii, Corynebacterium kutscheri, Corynebacterium lipophiloflavum, Corynebacterium lymphophilum, Corynebacterium massiliense, Corynebacterium matruchotii, Corynebacterium minutissimum, Corynebacterium propinquum, Corynebacterium pseudodiphtheriticum, Corynebacterium pseudotuberculosis, Corynebacterium renale, Corynebacterium riegelii, Corynebacterium simulans, Corynebacterium stations, Corynebacterium striatum, Corynebacterium timonense, Corynebacterium tuscaniense, Corynebacterium ulcerans, Corynebacterium urealyticum, Corynebacterium xerosis, Corynespora cassiicola, Cowpox virus, Coxiella burnetii, Cryptococcus bacillisporus, Cryptococcus bestiolae, Cryptococcus dejecticola, Cryptococcus deuterogattii, Cryptococcus fagi, Cryptococcus gattii, Cryptococcus neoformans, Cryptococcus pinus, Cryptococcus skinneri, Cryptococcus tetragattii, Cryptosporidium hominis, Cryptosporidium muris, Cryptosporidium parvum, Cunninghamella bertholletiae, Cupriavidus gilardii, Cupriavidus metallidurans, Curvularia lunata, Cyclospora cayetanensis, Cyphellophora europaea, Cytomegalovirus (CMV), Debaryomyces fabryi, Delftia acidovorans, Dermabacter hominis, Dermacoccus nishinomiyaensis, Diaporthe ampelina, Diaporthe aspalathi, Diaporthe longicolla, Dirofilaria immitis, Dracunculus medinensis, Dysgonomonas capnocytophagoides, Dysgonomonas gadei, Dysgonomonas hofstadii, Dysgonomonas mossii, Echinococcus granulosus, Echinococcus multilocularis, Echinostoma caproni, Edwardsiella hoshinae, Edwardsiella tarda, Eggerthella lenta, Ehrlichia canis, Ehrlichia chaffeensis, Ehrlichia muris, Eikenella corrodens, Elizabethkingia anophelis, Elizabethkingia meningoseptica, Elizabethkingia miricola, Emmonsia crescens, Emmonsia parva, Empedobacter brevis, Encephalitozoon cuniculi, Encephalitozoon hellem, Encephalitozoon intestinalis, Encephalitozoon romaleae, Entamoeba histolytica, Enterobacter aerogenes, Enterobacter amnigenus, Enterobacter cloacae complex, Enterobacter sakazakii, Enterobius vermicularis, Enterococcus asini, Enterococcus avium, Enterococcus casseliflavus, Enterococcus cecorum, Enterococcus columbae, Enterococcus dispar, Enterococcus durans, Enterococcus faecalis, Enterococcus faecium, Enterococcus gallinarum, Enterococcus gilvus, Enterococcus haemoperoxidus, Enterococcus hirae, Enterococcus italicus, Enterococcus malodoratus, Enterococcus mundtii, Enterococcus pallens, Enterococcus phoeniculicola, Enterococcus pseudoavium, Enterococcus raffinosus, Enterococcus saccharolyticus, Enterococcus sulfureus, Enterococcus thailandicus,

*Enterocytozoon bieneusi*, Epstein-Barr virus (EBV), *Erysipelothrix rhusiopathiae*, *Escherichia albertii*, *Escherichia blattae*, *Escherichia coli*, *Escherichia fergusonii*, *Escherichia hermannii*, *Escherichia vulneris*, *Eubacterium limosum*, *Eubacterium nodatum*, *Exophiala alcalophila*, *Exophiala aquamarina*, *Exophiala calicioides*, *Exophiala dermatitidis*, *Exophiala mesophila*, *Exophiala oligosperma*, *Exophiala sideris*, *Exophiala spinifera*, *Exophiala xenobiotica*, *Facklamia hominis*, *Facklamia sourekii*, *Fasciola hepatica*, *Filifactor alocis*, *Filobasidium wieringae*, *Finegoldia magna*, *Fonsecaea erecta*, *Fonsecaea monophora*, *Fonsecaea multimorphosa*, *Fonsecaea nubica*, *Fonsecaea pedrosoi*, *Francisella hispaniensis*, *Francisella noatunensis*, *Francisella philomiragia*, *Francisella tularensis*, *Fusarium avenaceum*, *Fusarium circinatum*, *Fusarium fujikuroi*, *Fusarium graminearum*, *Fusarium langsethiae*, *Fusarium nygamai*, *Fusarium oxysporum*, *Fusarium poae*, *Fusarium pseudograminearum*, *Fusarium sambucinum*, *Fusarium temperatum*, *Fusarium verticillioides*, *Fusarium virguliforme*, *Fusobacterium mortiferum*, *Fusobacterium necrophorum*, *Fusobacterium nucleatum*, *Fusobacterium varium*, Gammapapillomavirus 1, Gammapapillomavirus 2, Gammapapillomavirus 3, Gammapapillomavirus 4, Gammapapillomavirus 5, Gammapapillomavirus 6, Gammapapillomavirus 7, Gammapapillomavirus 8, Gammapapillomavirus 9, Gammapapillomavirus 10, Gammapapillomavirus 11, Gammapapillomavirus 13, Gammapapillomavirus 14, Gammapapillomavirus 15, Gammapapillomavirus 16, Gammapapillomavirus 17, Gammapapillomavirus 19, *Gardnerella vaginalis*, *Gemella bergeri*, *Gemella haemolysans*, *Gemella morbillorum*, *Gemella sanguinis*, *Geotrichum candidum*, *Giardia lamblia*, *Gordonia bronchialis*, *Gordonia rubripertincta*, *Gordonia terrae*, *Gordonibacter pamelaeae*, *Granulicatella adiacens*, *Granulicatella elegans*, *Grimontia hollisae*, *Haemophilus aegyptius*, *Haemophilus ducreyi*, *Haemophilus haemolyticus*, *Haemophilus influenzae*, *Haemophilus parahaemolyticus*, *Haemophilus parainfluenzae*, *Hafnia alvei*, *Hanseniaspora uvarum*, *Hansenula fabianii*, *Helicobacter cinaedi*, *Helicobacter fennelliae*, *Helicobacter pylori*, Herpes B virus, Herpes simplex virus type 1 (HSV-1), Herpes simplex virus type 2 (HSV-2), *Histoplasma capsulatum*, Human adenovirus A, Human adenovirus B, Human adenovirus C, Human adenovirus D, Human adenovirus E, Human adenovirus F, Human bocavirus, Human herpesvirus 6A, Human herpesvirus 6B, Human herpesvirus 7, Human papillomavirus, Human papillomavirus 132-like viruses, Human papillomavirus type 136, Human papillomavirus type 140, Human papillomavirus type 154, Human papillomavirus type 167, Human parvovirus, Human polyomavirus 6, Human polyomavirus 7, *Hymenolepis nana*, JC polyomavirus, Kaposi sarcoma-associated herpesvirus, KI polyomavirus, *Kingella denitrificans*, *Kingella kingae*, *Kingella oralis*, *Klebsiella oxytoca*, *Klebsiella pneumoniae*, *Kluyvera ascorbata*, *Kluyvera cryocrescens*, *Kluyvera intermedia*, *Kluyveromyces lactis*, *Kocuria kristinae*, *Kytococcus sedentarius*, *Lachancea kluyveri*, *Lachancea lanzarotensis*, *Lachancea thermotolerans*, *Lachancea waltii*, *Lactobacillus acidophilus*, *Lactobacillus casei*, *Lactobacillus crispatus*, *Lactobacillus fermentum*, *Lactobacillus gasseri*, *Lactobacillus iners*, *Lactobacillus jensenii*, *Lactobacillus plantarum*, *Lactobacillus rhamnosus*, *Lactobacillus sakei*, *Lactobacillus ultunensis*, *Lactococcus garvieae*, *Leclercia adecarboxylata*, *Legionella anisa*, *Legionella bozemanae*, *Legionella cherrii*, *Legionella drancourtii*, *Legionella dumoffii*, *Legionella fairfieldensis*, *Legionella fallonii*, *Legionella geestiana*, *Legionella hackeliae*, *Legionella jamestowniensis*, *Legionella lansingensis*, *Legionella longbeachae*, *Legionella massiliensis*, *Legionella micdadei*, *Legionella moravica*, *Legionella norrlandica*, *Legionella oakridgensis*, *Legionella pneumophila*, *Legionella shakespearei*, *Legionella wadsworthii*, *Leifsonia aquatica*, *Leishmania aethiopica*, *Leishmania amazonensis*, *Leishmania braziliensis*, *Leishmania donovani*, *Leishmania major*, *Leishmania mexicana*, *Leishmania panamensis*, *Leishmania peruviana*, *Leishmania tropica*, *Leminorella grimontii*, *Leptosphaeria maculans*, *Leptospira alexanderi*, *Leptospira alstonii*, *Leptospira biflexa*, *Leptospira borgpetersenii*, *Leptospira broomii*, *Leptospira fainei*, *Leptospira inadai*, *Leptospira interrogans*, *Leptospira kirschneri*, *Leptospira kmetyi*, *Leptospira licerasiae*, *Leptospira mayottensis*, *Leptospira meyeri*, *Leptospira noguchii*, *Leptospira santarosai*, *Leptospira terpstrae*, *Leptospira vanthielii*, *Leptospira weilii*, *Leptospira wolbachii*, *Leptospira wolffii*, *Leptospira yanagawae*, *Leptotrichia buccalis*, *Leuconostoc citreum*, *Leuconostoc lactis*, *Leuconostoc mesenteroides*, *Leuconostoc pseudomesenteroides*, *Lichtheimia corymbifera*, *Lichtheimia ramosa*, *Listeria grayi*, *Listeria innocua*, *Listeria ivanovii*, *Listeria monocytogenes*, *Listeria seeligeri*, *Listeria welshimeri*, *Loa loa*, *Lodderomyces elongisporus*, *Macrophomina phaseolina*, *Madurella mycetomatis*, *Malassezia caprae*, *Malassezia cuniculi*, *Malassezia dermatis*, *Malassezia equina*, *Malassezia furfur*, *Malassezia globosa*, *Malassezia nana*, *Malassezia obtusa*, *Malassezia pachydermatis*, *Malassezia slooffiae*, *Malassezia sympodialis*, *Malassezia yamatoensis*, *Mannheimia haemolytica*, *Megasphaera micronuciformis*, *Memnoniella echinata*, Merkel cell polyomavirus, *Metarhizium acridum*, *Metarhizium album*, *Metarhizium anisopliae*, *Metarhizium brunneum*, *Metarhizium guizhouense*, *Metarhizium majus*, *Metarhizium rileyi*, *Metarhizium robertsii*, *Methanobrevibacter smithii*, *Metschnikowia bicuspidata*, *Metschnikowia fructicola*, *Microbacterium foliorum*, *Microbacterium oxydans*, *Microbacterium paraoxydans*, *Microbacterium testaceum*, *Micrococcus luteus*, *Micrococcus lylae*, *Microsporum canis*, *Microsporum gypseum*, *Mobiluncus curtisii*, *Mobiluncus mulieris*, *Moellerella wisconsensis*, *Mogibacterium timidum*, Molluscum contagiosum virus, Monkeypox virus, *Moraxella atlantae*, *Moraxella catarrhalis*, *Moraxella lacunata*, *Moraxella nonliquefaciens*, *Moraxella phenylpyruvica*, *Morganella morganii*, *Mortierella alpina*, *Mortierella elongata*, *Mortierella verticillata*, *Mucor ambiguus*, *Mucor circinelloides*, *Mucor indicus*, *Mucor irregularis*, *Mucor velutinosus*, Mupapillomavirus 1, Mupapillomavirus 2, *Myceliophthora thermophila*, *Mycobacterium abscessus*, *Mycobacterium arupense*, *Mycobacterium asiaticum*, *Mycobacterium avium* complex (MAC), *Mycobacterium brisbanense*, *Mycobacterium canariasense*, *Mycobacterium chelonae*, *Mycobacterium chimaera*, *Mycobacterium cosmeticum*, *Mycobacterium fortuitum*, *Mycobacterium genavense*, *Mycobacterium goodii*, *Mycobacterium gordonae*, *Mycobacterium haemophilum*, *Mycobacterium heckeshornense*, *Mycobacterium heraklionense*, *Mycobacterium immunogenum*, *Mycobacterium iranicum*, *Mycobacterium kansasii*, *Mycobacterium kumamotonense*, *Mycobacterium kyorinense*, *Mycobacterium leprae*, *Mycobacterium mageritense*, *Mycobacterium malmoense*, *Mycobacterium marinum*, *Mycobacterium nebraskense*, *Mycobacterium neoaurum*, *Mycobacterium novocastrense*, *Mycobacterium parascrofulaceum*, *Mycobacterium peregrinum*, *Mycobacterium phlei*, *Mycobacterium scrofulaceum*, *Mycobacterium senegalense*, *Mycobacterium septicum*, *Mycobacterium setense*, *Mycobacterium simiae*, *Mycobacterium smegmatis*, *Mycobacterium szulgai*, *Mycobacterium thermoresistibile*, *Mycobacterium triplex*, *Mycobacterium tuberculosis* complex, *Mycobacterium tusciae, Mycobacterium vaccae, Mycobacterium wolinskyi, Mycobacterium xenopi, Mycoplasma fermentans, Mycoplasma genitalium, Mycoplasma hominis, Mycoplasma hyopneumoniae, Mycoplasma penetrans, Mycoplasma pneumoniae, Mycoplasma pulmonis, Myroides odoratimimus, Myroides odoratus, Naegleria fowleri, Nakaseomyces bacillisporus, Nakaseomyces delphensis, Nakazawaea peltata, Necator americanus, Nectria haematococca, Neisseria elongata, Neisseria flavescens, Neisseria gonorrhoeae, Neisseria lactamica, Neisseria meningitidis, Neisseria mucosa, Neisseria polysaccharea, Neisseria sicca, Neisseria weaveri, Neofusicoccum parvum, Neorickettsia helminthoeca, Neorickettsia sennetsu, Nocardia abscessus, Nocardia acidovorans, Nocardia africana, Nocardia alba, Nocardia amamiensis, Nocardia anaemiae, Nocardia aobensis, Nocardia araoensis, Nocardia arthritidis, Nocardia asiatica, Nocardia beijingensis, Nocardia brasiliensis, Nocardia brevicatena, Nocardia caishijiensis, Nocardia carnea, Nocardia cerradoensis, Nocardia concava, Nocardia coubleae, Nocardia crassostreae, Nocardia cummidelens, Nocardia cyriacigeorgica, Nocardia dassonvillei, Nocardia elegans, Nocardia exalbida, Nocardia farcinica, Nocardia flavorosea, Nocardia fusca, Nocardia gamkensis, Nocardia grenadensis, Nocardia harenae, Nocardia higoensis, Nocardia ignorata, Nocardia inohanensis, Nocardia jejuensis, Nocardia jiangxiensis, Nocardia kruczakiae, Nocardia lijiangensis, Nocardia mexicana, Nocardia mikamii, Nocardia miyunensis, Nocardia niigatensis, Nocardia niwae, Nocardia nova, Nocardia otitidiscaviarum, Nocardia paucivorans, Nocardia pneumoniae, Nocardia pseudobrasiliensis, Nocardia pseudovaccinii, Nocardia puris, Nocardia rhamnosiphila, Nocardia salmonicida, Nocardia seriolae, Nocardia shimofusensis, Nocardia sienata, Nocardia soli, Nocardia speluncae, Nocardia takedensis, Nocardia tenerifensis, Nocardia terpenica, Nocardia testacea, Nocardia thailandica, Nocardia transvalensis, Nocardia uniformis, Nocardia vaccinii, Nocardia vermiculata, Nocardia veterana, Nocardia vinacea, Nocardia violaceofusca, Nocardia xishanensis, Nocardia yamanashiensis, Nosema apis, Nosema bombycis, Nosema ceranae,* Nupapillomavirus 1, *Ochrobactrum anthropi, Ochrobactrum intermedium, Ochroconis constricta, Ochroconis gallopava, Odoribacter splanchnicus, Oerskovia turbata, Ogataea methanolica, Ogataea parapolymorpha, Ogataea polymorpha, Oligella ureolytica, Oligella urethralis, Olsenella uli, Onchocerca volvulus, Ophiostoma novo-ulmi, Ophiostoma piceae, Opisthorchis viverrini,* Orf virus, *Oribacterium sinus, Orientia tsutsugamushi, Paecilomyces hepiali, Paenibacillus alvei, Pantoea agglomerans, Paraburkholderia fungorum, Paracoccidioides brasiliensis, Paracoccidioides lutzii, Parvimonas micra, Pasteurella bettyae, Pasteurella multocida, Pasteurella pneumotropica, Pediococcus acidilactici, Pediococcus pentosaceus, Penicillium brasilianum, Penicillium camemberti, Penicillium capsulatum, Penicillium carneum, Penicillium digitatum, Penicillium expansum, Penicillium freii, Penicillium griseofulvum, Penicillium islandicum, Penicillium italicum, Penicillium marneffei, Penicillium nalgiovense, Penicillium nordicum, Penicillium oxalicum, Penicillium paneum, Penicillium paxilli, Penicillium piceum, Penicillium pinophilum, Penicillium purpurogenum, Penicillium roqueforti, Penicillium rubens, Penicillium verruculosum, Peptoniphilus coxii, Peptoniphilus duerdenii, Peptoniphilus harei, Peptoniphilus indolicus, Peptoniphilus lacrimalis, Peptoniphilus rhinitidis, Peptostreptococcus anaerobius, Peptostreptococcus stomatis, Phaeoacremonium minimum, Phanerochaete carnosa, Phanerochaete chrysosporium, Phellinus noxius, Phialophora attae, Phoma herbarum, Photobacterium damselae, Photorhabdus asymbiotica, Photorhabdus luminescens, Phycomyces blakesleeanus, Pichia anomala, Plasmodium cynomolgi, Plasmodium falciparum, Plasmodium knowlesi, Plasmodium ovale, Plasmodium vivax, Plesiomonas shigelloides, Pluralibacter gergoviae, Pneumocystis carinii, Pneumocystis jirovecii, Pneumocystis murina,* Porcine circovirus 1, Porcine circovirus 2, *Porphyromonas asaccharolytica, Porphyromonas gingivalis, Prevotella bivia, Prevotella buccae, Prevotella buccalis, Prevotella corporis, Prevotella denticola, Prevotella disiens, Prevotella intermedia, Prevotella loescheii, Prevotella melaninogenica, Prevotella oralis,* Primate bocaparvovirus 1, *Propionibacterium acidifaciens, Propionibacterium granulosum, Propionibacterium propionicum, Proteus mirabilis, Proteus vulgaris, Providencia alcalifaciens, Providencia rettgeri, Providencia stuartii,* Pseudocowpox virus, *Pseudomonas aeruginosa, Pseudomonas alcaligenes, Pseudomonas fluorescens, Pseudomonas fulva, Pseudomonas luteola, Pseudomonas mendocina, Pseudomonas mosselii, Pseudomonas oryzihabitans, Pseudomonas pseudoalcaligenes, Pseudomonas putida, Pseudoramibacter alactolyticus, Pseudozyma hubeiensis, Purpureocillium lilacinum, Pyrenochaeta lycopersici, Pyrenochaeta mackinnonii, Rahnella aquatilis, Ralstonia insidiosa, Ralstonia mannitolilytica, Ralstonia pickettii, Ramichloridium mackenziei, Rasamsonia emersonii, Rhizoctonia solani, Rhizomucor miehei, Rhizomucor variabilis, Rhizopus delemar, Rhizopus microsporus, Rhizopus oryzae, Rhizopus stolonifer, Rhodococcus equi, Rhodococcus erythropolis, Rhodococcus fascians, Rhodococcus rhodochrous, Rhodotorula graminis, Rhodotorula mucilaginosa, Rhodotorula toruloides, Rhytidhysteron rufulum, Rickettsia akari, Rickettsia amblyommii, Rickettsia australis, Rickettsia canadensis, Rickettsia conorii, Rickettsia felis, Rickettsia helvetica, Rickettsia honei, Rickettsia japonica, Rickettsia massiliae, Rickettsia monacensis, Rickettsia parkeri, Rickettsia prowazekii, Rickettsia raoultii, Rickettsia rickettsii, Rickettsia sibirica, Rickettsia slovaca, Rickettsia typhi, Riemerella anatipestifer, Roseomonas cervicalis, Roseomonas fauriae, Roseomonas gilardii, Roseomonas mucosa, Rothia aeria, Rothia dentocariosa, Rothia mucilaginosa, Saccharomyces cerevisiae, Saksenaea oblongispora, Saksenaea vasiformis, Salmonella bongori, Salmonella enterica, Scedosporium apiospermum, Scedosporium aurantiacum, Schistosoma haematobium, Schistosoma japonicum, Schistosoma mansoni, Schizophyllum commune, Serratia ficaria, Serratia fonticola, Serratia liquefaciens, Serratia marcescens, Serratia plymuthica, Serratia rubidaea, Shewanella algae, Shewanella putrefaciens, Shigella boydii, Shigella dysenteriae, Shigella flexneri, Shigella sonnei, Slackia exigua, Solobacterium moorei, Sphingobacterium spiritivorum, Sporopachydermia quercuum, Sporothrix brasiliensis, Sporothrix globosa, Sporothrix insectorum, Sporothrix pallida, Sporothrix schenckii, Stachybotrys chartarum, Stachybotrys chlorohalonata, Staphylococcus agnetis, Staphylococcus arlettae, Staphylococcus aureus, Staphylococcus auricularis, Staphylococcus capitis, Staphylococcus caprae, Staphylococcus carnosus, Staphylococcus caseolyticus, Staphylococcus chromogenes, Staphylococcus cohnii, Staphylococcus condimenti, Staphylococcus epidermidis, Staphylococcus equorum, Staphylococcus gallinarum, Staphylococcus haemolyticus, Staphylococcus hominis, Staphylococcus hyicus, Staphylococcus lentus, Staphylococcus lugdunensis, Staphylococcus pasteuri, Staphylococcus pettenkoferi, Staphylococcus pseudintermedius, Staphylococcus saprophyticus, Staphylococcus schleiferi, Staphylo-* coccus sciuri, Staphylococcus simiae, Staphylococcus simulans, Staphylococcus succinus, Staphylococcus vitulinus, Staphylococcus warneri, Staphylococcus xylosus, Stemphylium lycopersici, STL polyomavirus, Streptobacillus moniliformis, Streptococcus agalactiae, Streptococcus anginosus, Streptococcus canis, Streptococcus constellatus, Streptococcus cricetus, Streptococcus cristatus, Streptococcus dysgalactiae, Streptococcus equi, Streptococcus equinus, Streptococcus ferus, Streptococcus gallolyticus, Streptococcus gordonii, Streptococcus hyovaginalis, Streptococcus infantarius, Streptococcus infantis, Streptococcus iniae, Streptococcus intermedius, Streptococcus lutetiensis, Streptococcus macacae, Streptococcus massiliensis, Streptococcus mitis, Streptococcus mutans, Streptococcus oralis, Streptococcus parasanguinis, Streptococcus pasteurianus, Streptococcus peroris, Streptococcus pneumoniae, Streptococcus porcinus, Streptococcus pseudopneumoniae, Streptococcus pyogenes, Streptococcus ratti, Streptococcus salivarius, Streptococcus sanguinis, Streptococcus sobrinus, Streptococcus suis, Streptococcus thermophilus, Streptococcus uberis, Streptococcus vestibularis, Streptomyces somaliensis, Strongyloides stercoralis, Sutterella wadsworthensis, Syncephalastrum monosporum, Syncephalastrum racemosum, Taenia asiatica, Talaromyces cellulolyticus, Talaromyces leycettanus, Talaromyces stipitatus, Tanapox virus, Tatumella ptyseos, Thermoascus crustaceus, Thermomyces lanuginosus, Thielavia terrestris, Torque teno virus, Torque teno virus 1, Torque teno virus 2, Torque teno virus 3, Torque teno virus 4, Torque teno virus 6, Torque teno virus 7, Torque teno virus 8, Torque teno virus 10, Torque teno virus 12, Torque teno virus 14, Torque teno virus 15, Torque teno virus 16, Torque teno virus 19, Torque teno virus 25, Torque teno virus 26, Torque teno virus 27, Torque teno virus 28, Torulaspora delbrueckii, Toxocara canis, Toxoplasma gondii, Trachipleistophora hominis, Treponema pallidum, Trichinella nelsoni, Trichinella pseudospiralis, Trichinella spiralis, Trichoderma asperellum, Trichoderma atroviride, Trichoderma gamsii, Trichoderma hamatum, Trichoderma harzianum, Trichoderma longibrachiatum, Trichoderma parareesei, Trichoderma reesei, Trichoderma virens, Trichodysplasia spinulosa-associated polyomavirus, Trichomonas vaginalis, Trichophyton benhamiae, Trichophyton interdigitale, Trichophyton rubrum, Trichophyton verrucosum, Trichosporon asahii, Trichosporon cutaneum, Trichosporon guehoae, Trichosporon oleaginosus, Trichosporon porosum, Trichuris trichiura, Tropheryma whipplei, Trypanosoma brucei, Trypanosoma cruzi, Tsukamurella paurometabola, Turicella otitidis, Ureaplasma parvum, Ureaplasma urealyticum, Ustilago cynodontis, Ustilago esculenta, Ustilago hordei, Ustilago maydis, Ustilago trichophora, Vaccinia virus, Valsa mali, Varicella-zoster virus (VZV), Variola virus, Veillonella dispar, Veillonella montpellierensis, Veillonella parvula, Verticillium alfalfae, Verticillium dahliae, Verticillium longisporum, Verticillium tricorpus, Vibrio alginolyticus, Vibrio cholerae, Vibrio fluvialis, Vibrio furnissii, Vibrio harveyi, Vibrio metschnikovii, Vibrio mimicus, Vibrio parahaemolyticus, Vibrio vulnificus, Vittaforma corneae, Volvariella volvacea, Wallemia ichthyophaga, Wallemia mellicola, Weeksella virosa, Weissella confusa, Weissella paramesenteroides, Wickerhamomyces ciferrii, Wolbachia pipientis, WU Polyomavirus, Wuchereria bancrofti, Xanthomonas axonopodis, Yaba monkey tumor virus, Yarrowia deformans, Yarrowia keelungensis, Yarrowia lipolytica, Yersinia enterocolitica, Yersinia frederiksenii, Yersinia intermedia, Yersinia kristensenii, Yersinia pestis, Yersinia pseudotuberculosis, Yersinia ruckeri, Yokenella regensburgei. In some emboiments, the pathogens are cell-free. In some emboiments, the pathogen are intact, in exosomes, or associated with an exosome.

XII. Kits

The methods and composition of the disclosure can also be supplied in form of a kit. In general, a kit comprises a set of instructions for carrying out one or more methods of present disclosure.

In general, a kit provides concurrent detection of different nucleic acid forms in a sample. For example, in some embodiments, a kit can provide for the concurrent analysis of 2, 3, 4, 5, 6, 7, 8, 9, 10 or more nucleic acid forms in a sample. In another embodiment, a kit provides for the detection and processing of only one nucleic acid form in a sample.

In some embodiments, the kit can be tailored for a specific application such as diagnosis, prognosis, prediction of a disease, drug response, infection, fetal health information, or analysis of various genetic mutations related to a specific condition or disease. In some embodiments, the kit can be tailored with additional reagents or consumables for use with specific sample types, such as, blood, body fluids, tissues, particular cell types, or isolated nucleic acids.

The kit can be tailored for different detection methods (e.g., microarray, qPCR, ddPCR, or sequencing as provided herein). Depending on detection method used the kit can comprise the particular hardware, software, or reagents required for detection.

The kit can also comprise instructions. In some embodiments, the instructions of the kit outline steps for the detection and processing of highly degraded DNA or RNA or cell-free samples. In some embodiments, the instructions of the kit outline steps for the detection and processing of sample having or at risk of having disease or infection.

EXAMPLES

Example 1: Concurrent Analysis of Nucleic Acids Using the Primer Extension Method The study was conducted to test the primer extension method for the concurrent detection of different nucleic acids forms in a sample using polymerases that have different preferences for DNA and RNA templates.

A 10 µL sample was obtained that contained a mixture of RNA and DNA.

Uracil Excision and DNA Cleavage at Abasic Sites.

In an initial optional step, abasic sites were removed using Endonuclease VIII. In addition, deoxyuracils may optionally be removed from the nucleic acids in order to improve sequence accuracy. For each sample, a reaction mixture was prepared with a total volume of 42 µL in 0.5 mL tubes. The reaction mixture includes water (to 42 µL), 10× CircLigase buffer II (8 µL), MnCl$_2$ (4 µL, 50 mM), DNA extract (max. 29 µL), Endonuclease VIII (0.5 µL, 10 U µL$^{-1}$), and optionally Afu UDG (0.5 µL, 2 U µL$^{-1}$). The tubes were mixed and spun in a microcentrifuge. The reactions were incubated in a thermal cycler with a heated lid for 1 hr at 37° C.

Dephosphorylation and Heat Denaturation.

Before denaturation, phosphatase was added to the sample in order to remove residual phosphate groups from the 5' and 3' ends of the DNA strands in order to minimize self-circularization and prevent the phosphate groups from interfering with adapter ligation. FastAP (1 µL, 1 U) was added to each reaction mixture. Tubes were mixed and spun briefly in a microcentrifuge. The total reaction volume was 43 µL. The reactions were incubated in a thermal cycler with a heated lid for 10 min at 37° C., and then at 95° C. for 2 min. While the thermal cycler was still at 95° C., the tubes were quickly transferred into an ice-water bath. The reaction mix was cooled down for at least 1 min. The tubes were spun briefly in a microcentrifuge and placed in a tube rack at room temperature.

Ligation of the first adapter. PEG-4000 (32 µL, 50%), single-stranded adapter oligo CL78 (1 µL, 10 µM, 5'-[Phosphate]AGATCGGAAG[C3Spacer]$_{10}$[TEG-biotin]-3', (TEG=triethylene glycol spacer) (SEQ ID NO: 4)), and CircLigase II (4 µL, 100 U µL$^{-1}$) were added to the reaction mixtures to obtain a final reaction volume of 80 µL. The contents of the tubes were mixed before adding CircLigase II. The tubes were spun briefly in a microcentrifuge. The reaction mixtures were incubated in a thermal cycler with a heated lid for 1 hr at 60° C. Stop solution (2 µL) (98 µL of 0.5 M EDTA (pH 8.0) and 2 µL of Tween 20 were combined to make 100 µL of stop solution) was added to each reaction mixture. The contents were mixed, and the tubes were spun in a microcentrifuge.

Immobilization of Ligation Products on Beads.

The ligation products containing the biotinylated adapters may be immobilized on streptavidin beads. Such immobilization may be useful for wash steps. The stock of Dynabeads MyOne streptavidin C1 beads (Life Technologies) were resuspended by vortexing. For each sample, the bead suspension (20 µL) was transferred into a 1.5-mL tube. The beads were pelleted using a magnetic rack. The supernatant was discarded, and the beads were washed twice with bead-binding buffer (500 µL). 7.63 mL of water (HPLC-grade), 2 mL of 5 M NaCl, 100 µL of 1 M Tris-HCl (pH 8.0), 20 µL of 0.5 M EDTA (pH 8.0), 5 µL of Tween 20, and 250 µL of 20% (wt/vol) SDS were combined to make 10 mL of bead-binding buffer. SDS was added immediately before use. The beads were resuspended in a volume of bead-binding buffer corresponding to the number of samples times 250 µL (e.g., 1 mL for four samples). Per sample, an aliquot of 250 µL of bead suspension was transferred to a 1.5-mL tube. The ligation reactions were incubated for 1 min at 95° C. in a thermal cycler with a heated lid. While the thermal cycler was still at 95° C., the tubes were quickly transferred into an ice-water bath. The reaction mixture was cooled down for at least 1 min. The tubes were spun briefly in a microcentrifuge. The ligation reactions were added to the bead suspensions. The tubes were rotated for 20 min at room temperature. The tubes were spun briefly in a microcentrifuge. The beads were pelleted using a magnetic rack, and the supernatant was discarded. The beads were washed once with 200 µL of wash buffer A and once with 200 µL of wash buffer B. 47.125 mL of water, 1 mL of 5 M NaCl, 500 µL of 1 M Tris-HCl (pH 8.0), 100 µL of 0.5 M EDTA (pH 8.0), 25 µL of Tween 20, and 1.25 mL of 20% (wt/vol) SDS were combined to make 50 mL of wash buffer A, 48.375 mL of water, 1 mL of 5 M NaCl, 500 µL of 1 M Tris-HCl (pH 8.0), 100 µL of 0.5 M EDTA (pH 8.0), and 25 µL of Tween 20 were combined to make 50 mL of wash buffer B.

Primer Annealing and Extension.

For this step, a primer complementary to the adapter was used to copy the template strand. A master mix was prepared for the required number of reactions, according to the manufacturer's instructions (47 µL per reaction).

Bst 2.0 Polymerase.

For the master mix comprising, Bst 2.0 polymerase, 40.5 µL water, 5 µL 10× isothermal amplification buffer (New England Biolabs), 0.5 µL dNTP mix (25 mM each), and 1 µL extension primer CL9 (5'-GTGACTGGAGTTCAGACGT-GTGCTCTTCCGATCT-3' (SEQ ID NO: 1), 100 µM) were combined to make 47 µL master mix. The beads were pelleted using a magnetic rack, and the wash buffer was discarded. The 47-µL reaction mixture was added to the pelleted beads, and the beads were resuspended by vortexing. The tubes were incubated in a thermal shaker for 2 min at 65° C. The tubes were placed in an ice-water bath for 1 min and then were immediately transferred to a thermal cycler precooled to 15° C. While the tubes were placed on the thermal cycler, a polymerase (e.g., Bst 2.0 polymerase (3 µL, 24 U, New England Biolabs), DNA polymerase, or reverse transcriptase) was added to each reaction mixture. The tubes were mixed briefly by vortexing and returned to the thermal cycler. The reaction mixtures were incubated by increasing the temperature by 1° C. per minute, ramping the temperature up from 15° C. to 37° C. The reaction mixtures were incubated for 5 min at 37° C. The tubes were spun briefly in a microcentrifuge. The beads were pelleted using a magnetic rack, and the supernatant was discarded.

The beads were washed once with 200 µl of wash buffer A. The beads were resuspended in 100 µL of stringency wash buffer (49.5 ml of water, 250 µl of 20% (wt/vol) SDS, and 250 µL of 20×SSC buffer were combined to make 50 mL of stringency wash buffer), and the bead suspensions were incubated for 3 min at 45° C. in a thermal shaker. The beads were pelleted using a magnetic rack, and the supernatant was discarded. The beads were washed once with 200 µL of wash buffer B.

SMARTer RT.

Clonetech SMARTer RT can be used in place of Bst 2.0 polymerase, according to the manufacturer's instructions with the following modifications: 1) in-house extension primer CL9 (5'-GTGACTGGAGTTCAGACGTGT-GCTCTTCCGATCT-3' (SEQ ID NO:1)) was used for the primer extension in step 4 of the protocol in place of the manufacturer's 3' SMART CDS Primer II A, and 2) SMART-Seq v4 oligonucleotide was not used in the Step 6 of the manufacturer's protocol. The beads were pelleted on the magnet and reverse transcription products were collected in the supernatant, purified, amplified by PCR, and sequenced. Results were quantified also using TapeStation (Agilent).

If the sample was processed with Bst 2.0 polymerse in the primer extension step then the beads were washed once with 200 µl of wash buffer A. The beads were resuspended in 100 µL of stringency wash buffer (49.5 ml of water, 250 µl of 20% (wt/vol) SDS, and 250 µL of 20×SSC buffer were combined to make 50 mL of stringency wash buffer), and the bead suspensions were incubated for 3 min at 45° C. in a thermal shaker. The beads were pelleted using a magnetic rack, and the supernatant was discarded. The beads were washed once with 200 µL of wash buffer B.

Blunt-End Repair.

A blunt-end repair step may be used, particularly when blunt-end double-stranded second adapters were appended to the nucleic acid, which generally occurs at the end opposite to the end of the nucleic acid to which the first adapter was appended. A master mix was prepared for the required number of reactions (99 µL per reaction). 86.1 µL water, 10 µL 10× Buffer Tango (Thermo Scientific), 2.5 µL Tween 20 (1%), and 0.4 µL dNTP (25 mM each) were combined to make 99 µL master mix. The beads were pelleted using a magnetic rack, and the wash buffer was discarded. The reaction mixture (99 µL) was added to the pelleted beads, and the beads were resuspended by vortexing. T4 DNA polymerase (1 µL, 5 U, Thermo Scientific) was added. The tubes were mixed briefly by vortexing. The reaction mixtures were incubated for 15 min at 25° C. in a thermal shaker. The beads were kept suspended during incubation. EDTA (10 µL, 0.5 M) was added to each reaction mixture and mixed by vortexing. The beads were pelleted using a magnetic rack, and the supernatant was discarded. The beads were washed once with 200 µl of wash buffer A. The beads were resuspended in 100 µL of stringency wash buffer, and the bead suspensions were incubated for 3 min at 45° C. in a thermal shaker. The beads were pelleted using a magnetic rack, and the supernatant was discarded. The beads were washed once with 200 µL of wash buffer B.

Ligation of Second Adapter and Library Elution.

A master mix was prepared for the required number of reactions (98 µL per reaction). 73.5 µL water, 10 µL 10×T4 DNA ligase buffer, 10 µL PEG-4000 (50%), 2.5 µL Tween 20 (1%), and 2 µL double-stranded adapter (100 µM) were combined to make 98 µL master mix. To make the double-stranded adapter stock solution, 9.5 µL of TE buffer, 0.5 µL of 5 M NaCl, 20 µL of 500 µM oligonucleotide CL53 (5'-CGACGCTCTTC-ddC (SEQ ID NO: 2)) (ddC=dideoxycytidine), and 20 µL of 500 µM oligonucleotide CL73 (5'-[Phosphate] GGAAGAGCGTCGTGTAGGGAAAGAG*T*G*T*A-3' (SEQ ID NO: 3)) (*=phosphothioate linkage) were combined in a PCR tube, the reaction mixture was incubated in a thermal cycler for 10 s at 95° C., the temperature was slowly decreased at the rate of 0.1° C. per second until reaching 14° C., and 50 µL of TE buffer was added to the hybridized adapter to obtain a concentration of 100 µM in a total volume of 100 µL. 49.4 mL of water, 500 µL of 1 M Tris-HCl (pH 8.0), and 100 µL of 0.5 M EDTA (pH 8.0) were combined to make 50 mL of TE buffer. The beads were pelleted using a magnetic rack, and the wash buffer was discarded. The reaction mixture (98 µL) was added to the pelleted beads, and the beads were resuspended by vortexing. T4 DNA ligase (2 µL, 10 U, Thermo Scientific) was added. The contents were mixed briefly by vortexing. The reaction mixtures were incubated for 1 hr at room temperature. The beads were kept suspended during incubation. The beads were pelleted using a magnetic rack, and the supernatant was discarded. The beads were washed once with 200 µl of wash buffer A. The beads were resuspended in 100 µL of stringency wash buffer, and the bead suspensions were incubated for 3 min at 45° C. in a thermal shaker. The beads were pelleted using a magnetic rack, and the supernatant was discarded. The beads were washed once with 200 µL of wash buffer B. The beads were pelleted using a magnetic rack, and the supernatant was discarded. TET buffer (25 µL) (49.375 mL of water, 500 µL of 1 M Tris-HCl, 100 µL of 0.5 M EDTA, and 25 µL of Tween 20 were combined to make 50 mL of TET buffer) was added to the pelleted beads, and the beads were resuspended by vortexing. The bead suspension was transfer to 0.2-mL PCR strip tubes. The tubes were spun briefly in a microcentrifuge. The bead suspensions were incubated for 1 min at 95° C. in a thermal cycler with a heated lid. The PCR strip tubes were immediately transferred to a 96-well magnetic rack. The supernatant was transferred, which contains the library molecules, to a fresh 0.5-mL tube.

Library Amplification and Indexing.

A PCR mix was prepared using a unique combination of indexing primers for each sample. The PCR mix can be prepared with 57 µL water (to 100 µL), 10 µL 10× AccuPrime Pfx reaction mix (Life Technologies), 4 µL P7 indexing primer (10 µM), 4 µL P5 indexing primer or IS4 (10 µM), 24 µL library, and 1 µL AccuPrime Pfx polymerase (2.5 U µl$^{-1}$) (Life Technologies). The reactions were incubated in a thermal cycler with an initial denaturation at 95° C. for 2 min, followed by a selected number of PCR cycles, involving denaturation for 15 s at 95° C., annealing for 30 s at 60° C. and primer extension for 1 min at 68° C. The amplified libraries were purified using the MinElute PCR purification kit (Qiagen) or AMPure XP SPRI beads (Beckman Coulter) according to the manufacturer's instructions. The DNA was eluted in 20 µL of TE buffer. The fragment size distributions and concentrations of the DNA libraries were determined by running the Agilent Bioanalyzer 2100 with a DNA 1000 chip.

Sequencing.

For sequencing, the protocols and instructions for multiplex sequencing provided by Illumina were followed. The sequencing primer of the first read was replaced by the custom primer CL72 (5'-ACACTCTTTCCCTACAC-GACGCTCTTCC-3' (SEQ ID NO: 16)). A ready-to-use dilution of CL72 was freshly prepared before sequencing by mixing 10 µL from the 100 µM stock solution with 1,990 µL of hybridization buffer (provided with the sequencing reagents).

FIG. 11 shows bar graphs comparing the DNA and RNA input of the starting sample with the final DNA and RNA output detected after sequencing. Both polymerases showed the ability to carry out the primer extension against both DNA and RNA substrates, FIG. 11. The Bst 2.0 DNA polymerase showed primer extension for both templates, but preferentially worked on a DNA substrate, even in the presence of relatively high quantities of RNA substrate (FIG. 11B). However, the SMARTer reverse transcriptase provided primer extension against both DNA and RNA templates (FIG. 11A).

Example 2: Efficiency of Ligases in a Single Reaction Mixture

The study was conducted to determine if ligases can perform in a single reaction mixture provided by the disclosure.

Different ligases were tested for their ligation efficiency toward RNA fragments in the presence of DNA. Three different ligases were tested, CircLigase II, Thermostable AppDNA/RNA ligase, and T4 RNA ligase 1, in two sample mixtures that each included 4.5 pM of a 100 bp DNA oligonucleotide and either 10 nM (high) or 0.1 nM (low) of a 50 nucleotide RNA oligonucleotide. Following the ligation, the reaction mixtures were subjected to the protocol shown in FIG. 1 starting at the primer extension reaction 130.

Preparation of RNA/DNA Master Mixes:

Master mixes with either "high" or "low" concentration of a RNA oligonucleotides were made. The "high" concentration master mix contained RNA oligonucleotides at 10 nM, and the "low" concentration master mix contained RNA oligonucleotides at 100 pM. Both master mixes contained DNA oligonucleotides at 4.5 pM.

Enzymes were used according to the manufacturer's instructions. Prior to ligation, RNA oligonucleotides were treated with FastAP enzyme. DNA oligonucleotides were added after the FastAP treatment with the respective ligase.

The Adapter Used in the CircLigase II and T4 RNA Ligase 1 Ligation:

The adapter used was /5Phos/AGATCGGAAG/iSpC3/iSpC3/iSpC3/iSpC3/iSpC3/iSpC3/iSpC3/iSpC3/iSpC3/iSpC3/3 BioTEG/(SEQ ID NO: 4) and contains 5'-phosphylation, 3'-biotinylation, and non-nucleotide polymer extension. The Thermostable App ligase requires an App modification (e.g., pre-adenylation) at the 5'-end.

Ligation of the Adapter by CircLigase II:

RNA/DNA master mix (10 µL), deionized water (20 µL), CircLigase II Buffer (8 µL), MnCl$_2$ (4 µL, 50 mM), and FastAP (1 µL) were mixed to phosphorylate the 5'-end and dephosphorylate the 3'-ends in RNA and DNA oligonucleotides with the FastAP kinase. Each reaction mix was incubated at 37° C. for 10 min, followed by thermal deactivation at 95° C. for 2 min, and immediately placed on ice before proceeding to the ligation step. 50 w/v % PEG4000 (32 adapter oligo (1 and CircLigase II (4 µL) were added to the reaction from the kinase step to obtain a reaction mixture with 1× CircLigase Buffer II and 2.5 mM MnCl$_2$. The mixture was incubated at 60° C. for 1 h, followed by the addition of Stop Solution (0.5 M EDTA pH 8.0, 2 v/v % Tween-20) (2 µL) and inactivation at 95° C. for 1 min. After, the mixture was placed on ice and purified using a Zymo RNA purification column.

Ligation of the Adapter by Themostable AppDNA/RNA Ligase (NEB):

RNA/DNA master mix (10 deionized water (2.5 NEB Buffer #1 (2.0 MnCl$_2$ (2 µL, 50 mM), and FastAP (1 µL) were mixed to phosphorylate the 5'-end and dephosphorylate the 3'-ends in RNA and DNA oligonucleotides with the FastAP kinase. Each reaction mix was incubated at 37° C. for 10 min, followed by thermal deactivation at 95° C. for 2 min, and immediately put on ice before proceeding to the ligation step. Thermostable AppDNA/RNA ligase (2.0 µL) and adapter oligo (0.5 µL) were added to the reaction from the kinase step to obtain a reaction mixture with 1× NEB Buffer #1 and 5 mM MnCl$_2$. The mixture was incubated at 65° C. for 1 h and inactivated at 90° C. for 3 min. The mixture was placed on ice and purified with a Zymo RNA purification column.

Ligation of the Adapter by T4 RNA Ligase 1 (NEB):

RNA/DNA master mix (10 µL), deionized water (27 µL), 10× T4 RNA Ligase Buffer (6 µL), and FastAP (1 µL) were mixed to phosphorylate the 5'-end and dephosphorylate the 3'-ends in RNA and DNA oligonucleotides with the FastAP kinase. Each reaction mix was incubated at 37° C. for 10 min, followed by thermal deactivation at 95° C. for 2 min, and immediately put on ice before proceeding to the ligation step. ATP (6 µL, 10 mM), T4 RNA ligase 1 (1 µL), and adapter oligo (3 µL) were added to the reaction from the kinase step to obtain a reaction mixture with 1× T4 RNA Ligase Reaction Buffer and 1 mM ATP. The mixture was incubated at 37° C. for 1 h, placed on ice, and purified with a Zymo RNA purification column.

Post-Ligation Reverse Transcription was Performed with Clonetech SMARTer RT:

The reverse transcription reaction was carried out according to the manufacturer's instructions with the following modifications: 1) in-house extension primer CL9 (5'-GTGACTGGAGTTCAGACGTGTGCTCTTCCGATCT-3' (SEQ ID NO: 1)) was used for the primer extension reaction in step 4 of the protocol in place of the manufacturer's 3' SMART CDS Primer II A, and 2) SMART-Seq v4 oligonucleotide was not used in the step 6 of the manufacturer's protocol. Reverse transcription products were amplified by PCR. The amplified products were quantified using TapeStation (Agilent).

Figure 10:
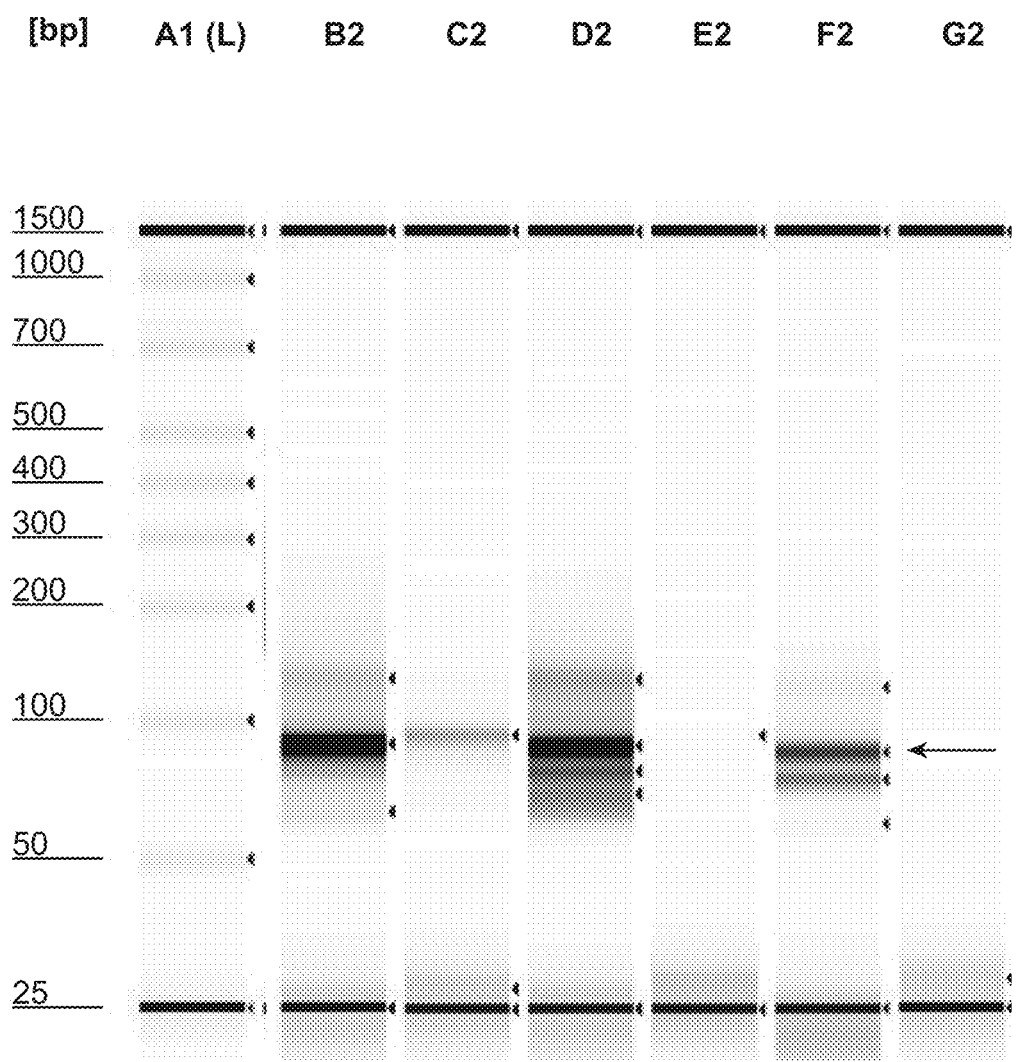
FIG. 10 shows an electrophoric gel illustrating the efficiency of different DNA and RNA ligases in a single reaction mixture provided by the disclosure. Lane A1 of the gel shows the molecular ladder (L); Lanes B2 and C2 is the product produced using a CircLigase II. Lanes D2 and E2 is the product produced using a thermostable App-DNA/RNA ligase. Lanes F2 and G2 is the product produced using a T4 RNA ligase 1.

FIG. 10 shows the detected and amplified products using gel electrophoresis. The three tested ligases showed varying degrees of efficacy in the presence of DNA. The arrow in FIG. 10 indicates the expected 84 nt product (50 nt sequence and 34 nt adapter). The CircLigase II showed the greatest efficiency for both high and low RNA concentration mixtures (lanes B2 (high) and C2 (low)), with decreasing efficiency ligation for the thermostable App-DNA/RNA ligase (lanes D2 (high) and E2 (low)), and for T4 RNA ligase 1 (lanes F2 (high) and G2 (low)).

The CircLigase in lane B2 yielded 243 nM solution of reverse-transcribed RNA oligonucleotide after 11 cycles of PCR following the SMARTer RT step, which is about 14.2% of the expected recovery.

Example 3: Efficiency of DNA and RNA Polymerases in a Single Reaction Mixture

The study was conducted to determine if polymerase enzymes can perform in the single reaction mixtures provided by the disclosure.

The ligation method was carried out on both DNA and RNA samples to the end of the primer extension step of FIG. 1, 130. Two different polymerases, Bst-polymerase and SMARTer reverse transcriptase were tested on the ligation products. Both polymerases were added at similar levels to different single reaction mixtures comprising eight DNA fragments of different lengths, a single sample index spike-in DNA fragment, and 10 nM of RNA oligonucleotides.

Figure 12:
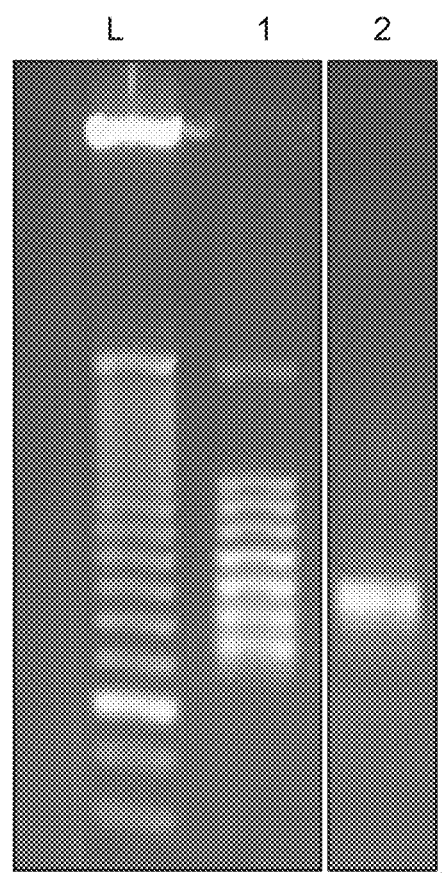
FIG. 12 shows an electrophoric gel illustrating nucleic acid products detected using the methods of the disclosure.

FIG. 12 shows the detected and amplified products of the ligation method using gel electrophoresis. In FIG. 12, "L" indicates the molecular ladder (25 bp Step Ladder). Lane, "1" shows the DNA detected in the sample using ligation and a Bst 2.0 polymerase. Lane "2" shows the RNA detected in the sample using ligation and a SMARTer Reverse Transcriptase.

Example 4: Efficiency of Reverse Transcriptases in a Single Reaction Mixture

The study was conducted to determine if reverse transcriptase enzymes can perform in the single reaction mixtures provided by the disclosure.

Different reverse transcriptase enzymes were tested for their discrimination between DNA and RNA templates during the first replication reaction. Four different reverse transcriptases, Superscript IV RT (Invitrogen), M-MLV Rnase H(−) (Promega), SMARTer reverse transcriptase (Clutch), and Revert Aid RnaseH(−) RT (Thermo Scientific), were added at similar activity levels to different reaction mixtures that each included 8 different length DNA fragments, a single sample index spike in DNA fragment, and 10 nM of RNA oligonucleotides. The reactions were then carried through the entire single-stranded protocol shown in FIG. 1, but using these specific polymerases for the primer extension reaction step, 130.

The protocol outlined in Example 1 was followed, except that steps in the primer annealing and extension section of Example 1 were modified with the specific protocol for each RT enzyme as described herein.

For Superscript IV samples, Solution A was prepared by mixing the extension primer CL9 (1.38 µL, 100 µM), dNTP mix (1.6 µL, 25 mM), and deionized water (49.04 µL). Solution B was prepared by mixing 5× Superscript IV Buffer (16 µL), DTT (4 µL, 100 mM), Rnase OUT inhibitor (4 µL), and Superscript IV RT (4 µL). Next, Solution A (26 µL) was added to the sample. Samples were incubated at 65° C. for 2 min and immediately placed on ice for 1 min. Next, Solution B (14 µL) was added to the sample, and samples were incubated at 42° C. for 1 h.

For M-MLV RT (Rnase H(−)) samples, Solution A was prepared by mixing extension primer CL9 (1.38 µL, 100

μM) and deionized water (54.64 μL). Solution B was prepared by mixing 5× M-MLV RT Buffer (20 μL), dNTP mix (2 μL, 25 mM), M-MLV RT (Rnase H(–)) (4 μL), and deionized water (17.98 μL). Solution A (28 μL) was added to the sample, and then samples were incubated at 65° C. for 2 min and placed on ice for 1 min. Next, Solution B (22 μL) was added to the sample, and the samples were incubated at 42° C. for 1 h.

For SMARTEer RT samples, 10× Reaction Buffer was prepared by mixing 10× Lysis Buffer (19 μL) and Rnase inhibitor (1 μL). Solution A was prepared by mixing 10× Reaction Buffer (1 μL) and deionized water (9.5 μL). Solution B was prepared by mixing 5× Ultra low 1st Strand Buffer (16 μL), SMARTer Seq v4 oligo (4 μL, 48 μM), and Rnase OUT inhibitor (2 μL). Beads were resuspended in Solution A (21 μL). Extension primer CL9 (4 μL, 12 μM) was added. Samples were incubated at 65° C. for 2 min and placed on ice. SMARTer RT (4.4 μL) was added to Solution B, and the mixture (15.0 μL) was added to the sample. Samples were incubated at 42° C. for 90 min.

For RevertAid RT samples, Solution A was prepared by mixing 4 μL 100 μM extension primer CL9, 46 μL deionized water. Solution B was prepared by mixing 16 μL 5× Thermo Reaction Buffer, 2 μL Rnase inhibitor, 3.2 μL 25 mM dNTP mix, 4 μL RevertAid RT. Solution A (25 μL) was added to the sample, and samples were incubated at 65° C. for 2 min and placed on ice. Solution B (15 μL) was added to the sample, and samples were incubated at 42° C. for 1 h.

Figure 13:
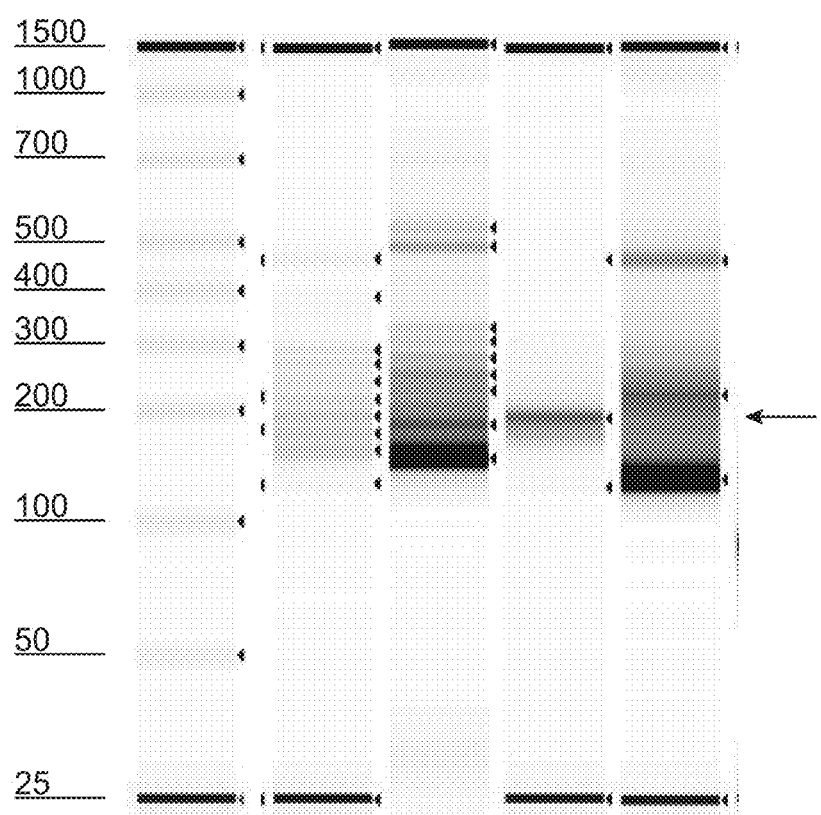
FIG. 13 depicts a primer extension reaction using various reverse transcriptase enzymes.

FIG. 13 provides a gel showing the products generated by the ligation method of Example 1 using different polymerases. Lane "F1" shows the product generated by Superscript IV RT. Lane "G1" shows the product generated by M-MLV Rnase H(–). Lane "H1" shows the product generated by SMARTer reverse transcriptase. Lane "A2" shows the product generated by RevertAid RnaseH(–).

The reverse transcriptases showed varying abilities to discriminate against DNA and RNA substrates the reaction mixture, FIG. 13. Lane H1 shows that the SMARTer reverse transcriptase has specific activity for RNA, while the other reverse transcriptases act on both DNA and RNA.

Example 5: Concurrent Detection of Pathogens from a Low-Quality Sample

Figure 6:
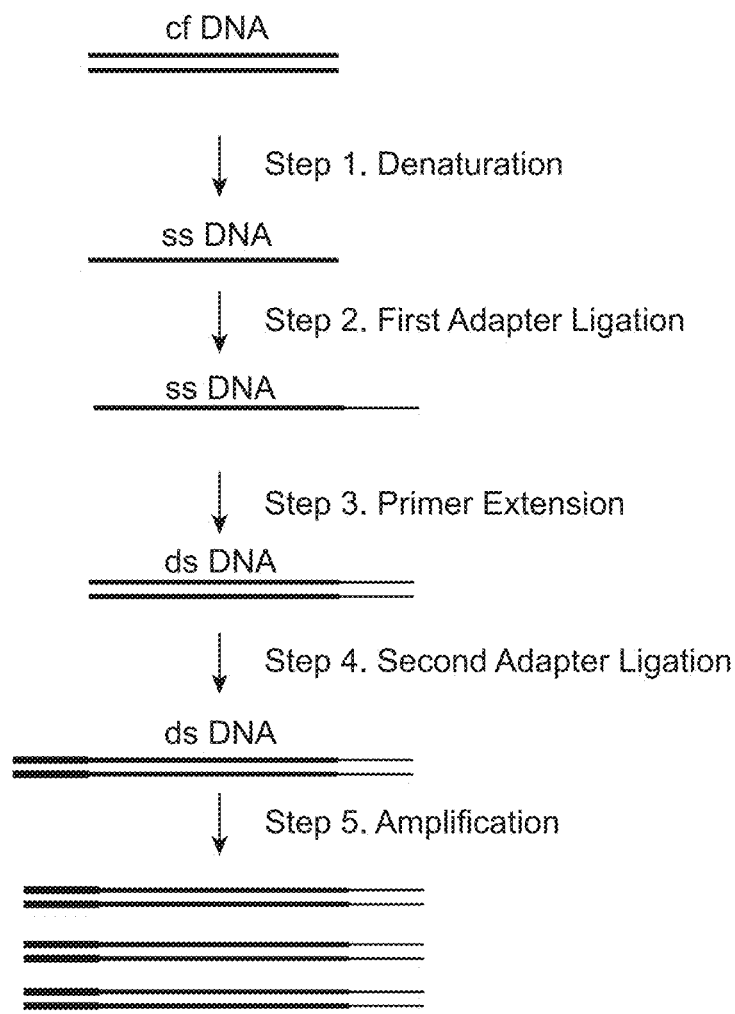
FIG. 6 depicts a approaches for detecting cell-free nucleic acids, or other low-quality forms, in a sample.

This study was carried out to test the performance of the low-quality method, using cfDNA shown in FIG. 6 compared to the NuGEN Ovation® Ultralow System V2 Reagents library protocol, using double-stranded DNA.

Figure 16:
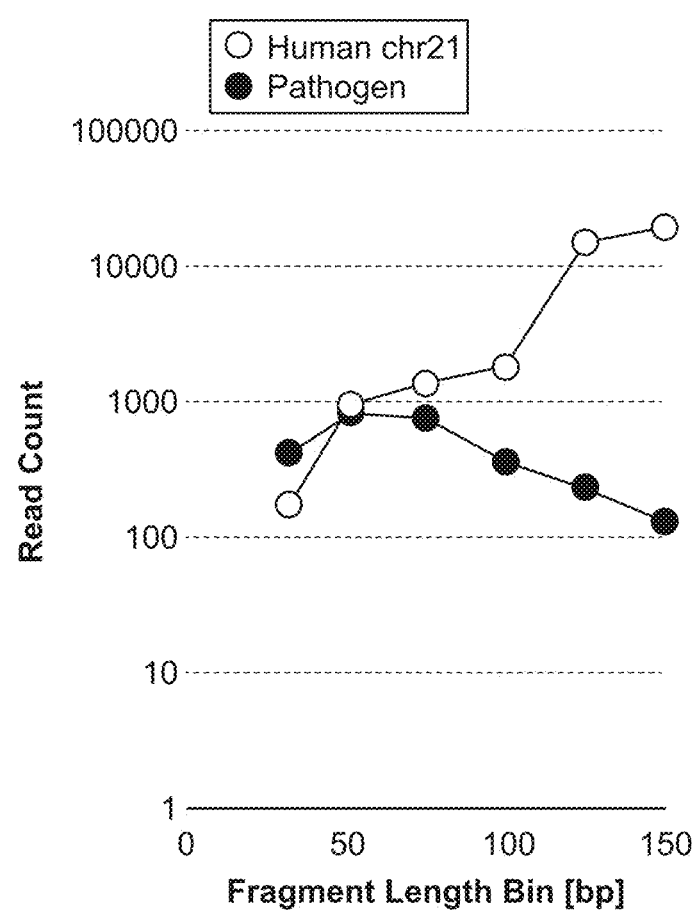
FIG. 16 depicts a plot of the quantity versus fragment length for both human chr21 and pathogen cell-free DNA detected using the methods provided herein.

Cell-free pathogen DNA from plasma represents a low-quality sample. That is, cell-free pathogen DNA is generally shorter and at much lower concentration than human DNA, FIG. 16. FIG. 16 shows a plot comparing the quantity and length of cell-free DNA (measured as a function of the number of sequence reads) to human DNA from chr21 using high-throughput sequencing.

Briefly, blood samples were obtained from volunteers. Blood culture tests were performed in parallel on the clinical samples to confirm that the blood samples used contained the selected pathogens being compared in the low-quality method and the NuGEN method.

Subsequently, high-throughput sequencing was conducted for selected pathogens. Normalized unique reads in size-selected libraries were determined for the selected pathogens and the results are shown in FIG. 14 and FIG. 15.

Figure 14:
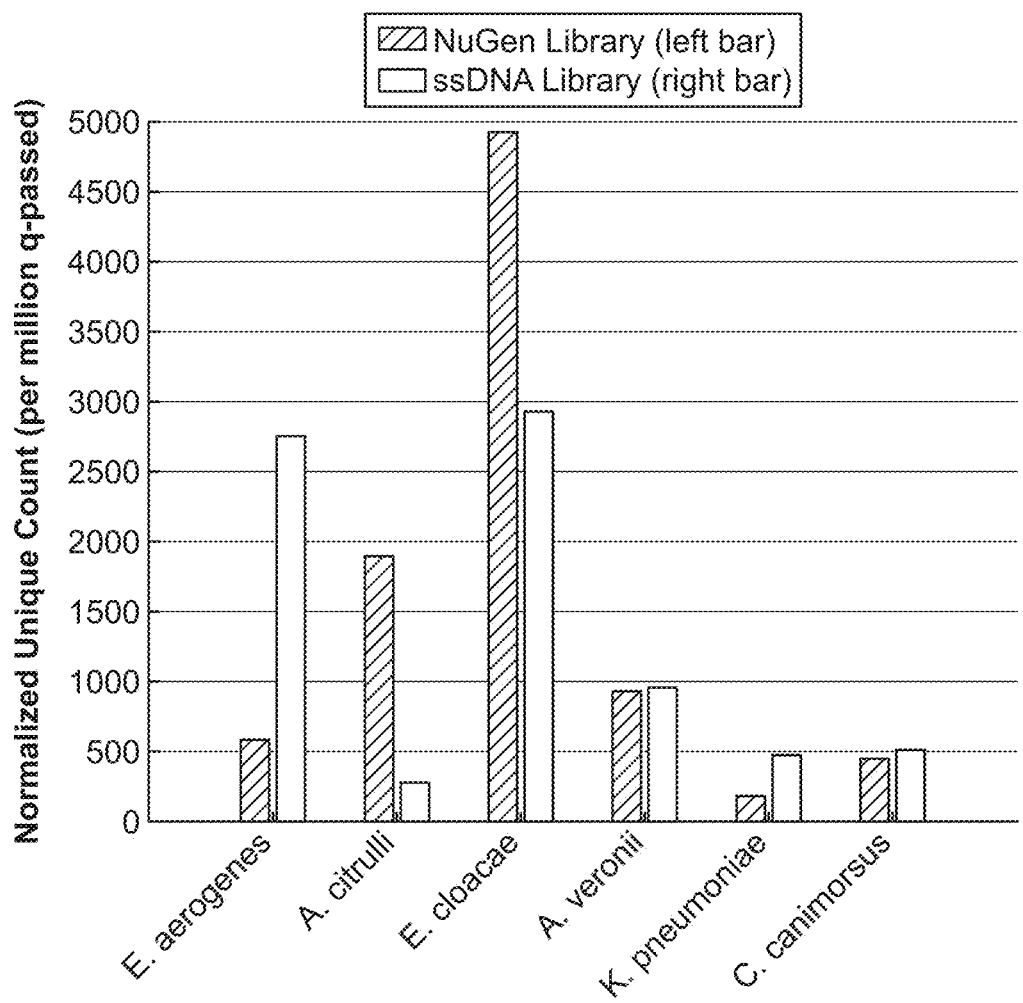
FIG. 14 depicts a bar graph comparing the performance of an embodiment of the ligation method with a commercial kit by NuGEN. The white bars indicate the number of nucleic acid products detected by the ligation method. The hatched bars indicate the number of nucleic acid products detected NuGEN method. The x-axis shows the name of the selected pathogens for the study.
Figure 15:
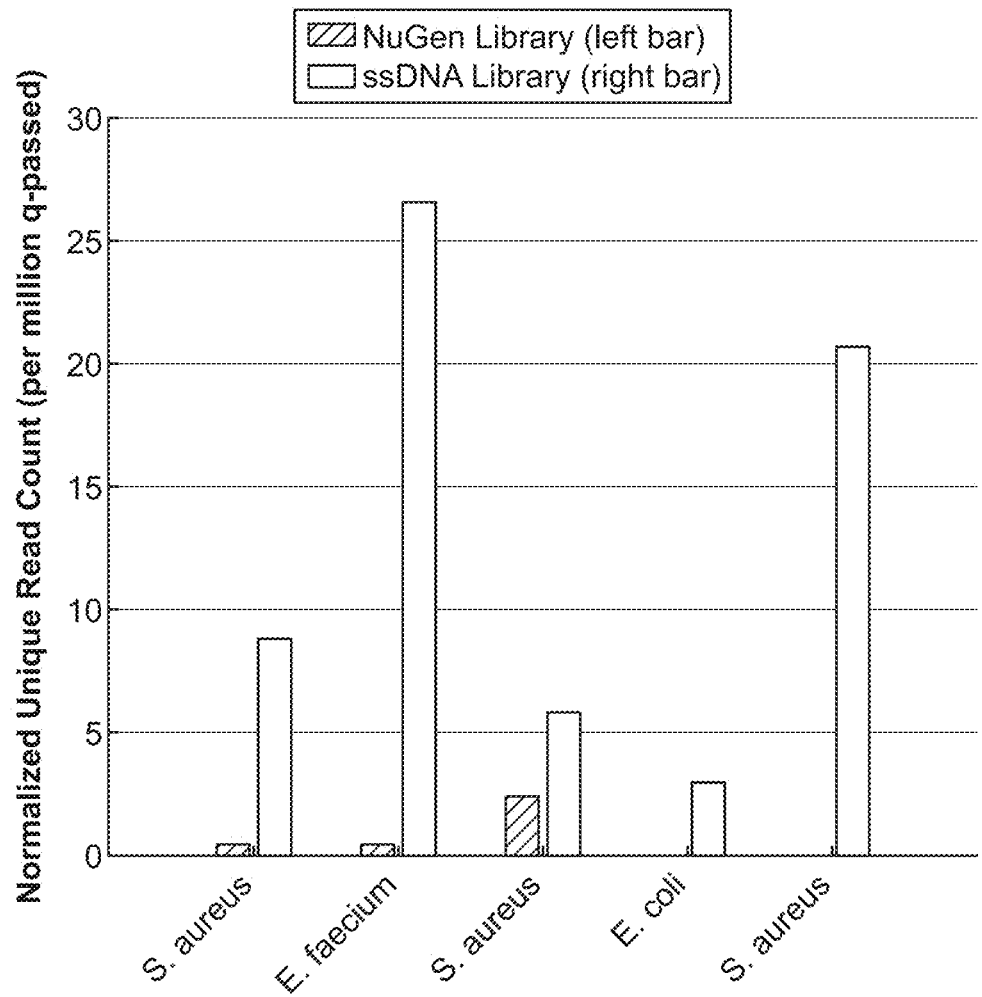
FIG. 15 depicts a bar graph comparing the performance of an embodiment of the ligation method with a commercial kit by NuGEN. The white bars indicate the number of nucleic acid products detected by the ligation method. The hatched bars indicate the number of nucleic acid products detected NuGEN method. The x-axis shows the name of the selected pathogens for the study.

FIG. 14 shows that the ligation method detected a higher number of reads for three of the six selected pathogens, *E. aerogenes, K pneumoniae,* and *C. canimorsus.* FIG. 15 shows that all of the selected pathogens were detected a higher number of reads when compared with the NuGEN method, *S. aureus, E. faecium,* and *E. coli.* Furthermore, the NuGEN method failed to detect, *E. coli* and *S. aureus* in two of the infected plasma samples, FIG. 15.

Example 6: Primer Extension-Non-Templated Method Using Successive Mode (Prophetic)

A primer extension-non-templated method using a successive mode can be used to detect different nucleic acid forms in a sample, FIG. 7.

Samples can be prepared and analyzed as in Example 1 with the following modifications. The blunt-end repair steps in Example 1 are skipped to avoid blunting the templates. After the primer annealing and extension steps in Example 1, a reverse transcription step (e.g., using M-MLV reverse transcriptase or SMARTer reverse transcriptase) is introduced.

A sample having both single-stranded and double-stranded nucleic acids is obtained and denatured to make single-stranded nucleic acids. Next, a first adapter is ligated to the single-stranded nucleic acids. After ligation is completed, a primer extension reaction is carried out with a DNA-dependent polymerase that has non-templated activity (e.g., Bst 2.0 polymerase or the like). Following the DNA polymerase reaction, an RT polymerase reaction is conducted that has non-templated activity (e.g., using M-MLV reverse transcriptase, SMARTer reverse transcriptase, or the like). Following the two primer extension reactions, a double-stranded adapter that has ends complementary to the primer-extended products is ligated.

Depending on the amount of material needed in the downstream detection assay, the products generated from the method can be amplified by PCR.

Example 7: Primer Extension-Non-Templated Method Using Concurrent Mode (Prophetic)

A primer extension-non-templated method using a concurrent mode can be used to detect different nucleic acid forms in a sample, FIG. 8.

Samples are prepared and analyzed as in Example 1 except the blunt-end repair step is omitted.

A sample having both single-stranded and double-stranded nucleic acids is obtained and denatured to make single-stranded nucleic acids. Next, a first adapter is ligated to the single-stranded nucleic acids. After ligation is completed, a primer extension reaction is carried out concurrently with a DNA-dependent polymerase that has non-templated activity (e.g., Bst 2.0 polymerase or the like) and a RNA-specific DNA polymerase that has non-templated activity. After, a second double-stranded adapter complementary to the primer-extended product is ligated.

Depending on the amount of material needed in the downstream detection assay, the products generated from the method can be amplified by PCR.

Example 8: Distinguishing Structural Forms of Nucleic Acids in a Sample (Prophetic)

A method for distinguishing between single-stranded and double-stranded nucleic acid forms can be used to detect these different forms in a sample.

This method generally, uses a dsRNA ligase and a dsDNA ligase with adapters having different identifying sequences (e.g. codes) for DNA and RNA.

Samples are prepared and analyzed as in Example 1 with the following modifications. Prior to the heat denaturation, a ligation step is added using a ligase specific for double-stranded nucleic acids (e.g., DNA or RNA). Then, end repair can be performed to generate blunt ends (FIG. 9, step 1). Next, one can use either the concurrent ligation mode or successive ligation mode to attach an identifying sequence to the double-stranded nucleic acids in the sample (e.g. dsDNA, and dsRNA), FIG. 9, step 2. To differentiate between dsDNA and dsRNA one can use two different identifying sequences in the adapters, FIG. 9, step 2. That is, a dsRNA ligase that attaches the adapters to double-stranded RNA can be designed with an RNA-identifying code, and a dsRNA ligase that attaches the adapters to dsRNA can be designed with a DNA-identifying code.

Next, one may proceed with the sample preparation process as provided herein, FIG. 9, step 3. Finally, the detection of the identifying codes added to the dsDNA and dsRNA can be used to distinguish between the double-stranded DNA and RNA in the starting sample from the single-stranded nucleic acids.

In other embodiments, ligation of dsDNA and dsRNA can be performed in succession or concurrently using ligases specific for DNA and/or RNA, such as T4 DNA Ligase. Short sequences can be deactivated to prevent their concatemerization.

Example 9: Splint Ligase Method for Concurrent Detection of Nucleic Acids in a Sample (Prophetic)

A splint ligase method can be used to detect different nucleic acid forms in a sample, FIG. 20.

Briefly, a sample can be obtained comprising both DNA and RNA nucleic acid forms. The nucleic acids in the sample are extracted and denatured. Next, a first adapter is ligated to the 3' end of RNA and DNA and the 5' ends are phosphorylated. Next, the nucleic acids are incubated with a hybrid splint molecule, composed of for example, SEQ ID NO:14 and SEQ ID NO:15, or the like, resulting in the hybridization of the splint molecule to the 5' of the DNA and the 5' end of the RNA.

Next, a ligation reaction is carried out using a SplintR Ligase enzyme or the like. After the ligation reaction is completed, the sample is treated at a high temperature to release the unligated splint molecules from the 5' end of the RNA molecules. Next, one can proceed with FIG. 1, step 130. Depending on the amount of material needed in the downstream detection assay, the products can be amplified by PCR.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually and separately indicated to be incorporated by reference for all purposes.

What is claimed is:

1. A method for performing a primer extension reaction on RNA and DNA, comprising:
   a) providing a sample comprising a mixture of single-stranded DNA and single-stranded RNA;
   b) attaching a first adapter to said single-stranded DNA;
   c) attaching a second adapter to said single-stranded RNA;
   d) annealing a first primer to said first adapter and annealing a second primer to said second adapter;
   e) extending said annealed first primer on said single-stranded DNA to form double-stranded DNA; and
   f) extending said annealed second primer on said single-stranded RNA to form a double-stranded DNA-RNA hybrid.

2. The method of claim 1, wherein said attaching said first adapter comprises ligating said first adapter to a 3' end of said single-stranded DNA.

3. The method of claim 2, wherein said ligating said first adapter is performed by a ligase selected from the group consisting of CircLigase II, Thermostable App-DNA/RNA ligase, T4 RNA ligase 1, T4 RNA Ligase 2 truncated, and any combination thereof.

4. The method of claim 1, wherein said attaching said second adapter comprises ligating said second adapter to a 3' end of said single-stranded RNA.

5. The method of claim 4, wherein said ligating said second adapter is performed using an RNA ligase.

6. The method of claim 4, wherein said ligating said second adapter is performed using T4 RNA ligase 2 or T4 DNA ligase.

7. The method of claim 1, wherein said single-stranded DNA is cell-free DNA.

8. The method of claim 1, wherein said sample is selected from the group consisting of blood, plasma, serum, cerebrospinal fluid, synovial fluid, bronchio-alveolar lavage, urine, stool, saliva, nasal swab, and any combination thereof.

9. The method of claim 1, wherein said extending said annealed first primer on said single-stranded DNA is performed by a DNA polymerase.

10. The method of claim 1, wherein said extending said annealed first primer on said single-stranded DNA is performed by Bst 2.0 DNA polymerase.

11. The method of claim 1, wherein said extending said annealed second primer on said single-stranded RNA is performed by a reverse transcriptase.

12. The method of claim 1, further comprising adding at least one non-templated nucleotide to a first primer extension strand.

13. The method of claim 12, wherein said at least one non-templated nucleotide is a deoxycytidine.

14. The method of claim 12, wherein said at least one non-templated nucleotide is added to a 3' end.

15. The method of claim 12, wherein said at least one non-templated nucleotide is up to eight nucleotides.

16. The method of claim 12, wherein said at least one non-templated nucleotide is three, four, or five non-templated nucleotides.

17. The method of claim 12, wherein said at least one non-templated nucleotide is one non-templated nucleotide.

18. The method of claim 12, wherein said at least one non-templated nucleotide forms a first overhang.

19. The method of claim 18, further comprising adding at least one second non-templated nucleotide to a second primer extension strand forming a second overhang.

20. The method of claim 19, further comprising hybridizing a third adapter to said first overhang and a fourth adapter to said second overhang.

21. The method of claim 20, further comprising sequencing said third adapter and said fourth adapter and sequences attached to said third adapter and said fourth adapter.

22. The method of claim 20, further comprising (i) identifying sequences associated with said third adapter as originating from said DNA in said mixture of single-stranded DNA and single-stranded RNA and (ii) identifying sequences associated with said fourth adapter as originating from said RNA in said mixture of single-stranded DNA and single-stranded RNA.

\* \* \* \* \*

SEQUENCE LISTING

```
<160> NUMBER OF SEQ ID NOS: 16

<210> SEQ ID NO 1
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gtgactggag ttcagacgtg tgctcttccg atct                               34

<210> SEQ ID NO 2
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
cgacgctctt cc                                                       12

<210> SEQ ID NO 3
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
```
ggaagagcgt cgtgtaggga aagagtgta                                    29

<210> SEQ ID NO 4
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
agatcggaag                                                         10

<210> SEQ ID NO 5
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gtgactggag ttcagacgtg tgctcttccg atct                              34

<210> SEQ ID NO 6
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
aatgatacgg cgaccaccga gatctacacc ctgcgaacac tctttcccta cacgacgctc  60
tt                                                                 62

<210> SEQ ID NO 7

<400> SEQUENCE: 7

000

<210> SEQ ID NO 8

<400> SEQUENCE: 8

000

<210> SEQ ID NO 9

<400> SEQUENCE: 9

000

<210> SEQ ID NO 10
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
caagcagaag acggcatacg agatatcttg cgtgactgga gttcagacgt gt          52

<210> SEQ ID NO 11

```
<400> SEQUENCE: 11

000

<210> SEQ ID NO 12

<400> SEQUENCE: 12

000

<210> SEQ ID NO 13

<400> SEQUENCE: 13

000

<210> SEQ ID NO 14
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(16)
<223> OTHER INFORMATION: a, c, t, g, unknown or other

<400> SEQUENCE: 14
cttccgatct nnnnnn                                                      16

<210> SEQ ID NO 15

<400> SEQUENCE: 15

000

<210> SEQ ID NO 16
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
acactctttc cctacacgac gctcttcc                                          28
```